(12) United States Patent
Bergmann

(10) Patent No.: US 10,421,746 B2
(45) Date of Patent: Sep. 24, 2019

(54) ORGANIC MOLECULES, ESPECIALLY FOR USE IN ORGANIC OPTOELECTRONIC DEVICES

(71) Applicant: CYNORA GMBH, Bruchsal (DE)

(72) Inventor: Larissa Bergmann, Karlsruhe (DE)

(73) Assignee: CYNORA GMBH, Bruchsal (DE)

( * ) Notice: Subject to any disclaimer, the term of this patent is extended or adjusted under 35 U.S.C. 154(b) by 0 days.

(21) Appl. No.: 15/801,238

(22) Filed: Nov. 1, 2017

(65) Prior Publication Data

US 2018/0134686 A1 May 17, 2018

(30) Foreign Application Priority Data

Nov. 1, 2016 (DE) .......................... 10 2016 120 802
Feb. 6, 2017 (DE) .......................... 10 2017 102 267
Mar. 16, 2017 (DE) .......................... 10 2017 105 693

(51) Int. Cl.
*H01L 51/54* (2006.01)
*C09K 11/06* (2006.01)
(Continued)

(52) U.S. Cl.
CPC ......... *C07D 403/10* (2013.01); *C07D 403/14* (2013.01); *C09K 11/06* (2013.01);
(Continued)

(58) Field of Classification Search
CPC .. C07D 209/86; C07D 209/88; C07D 401/00; C07D 401/10; C07D 401/14; C07D 403/00; C07D 403/10; C07D 403/14; C07D 405/00; C07D 405/10; C07D 405/14; C07D 487/00; C07D 487/02; C07D 487/04; C07D 493/00; C07D 493/0204; C07D 519/00; C09K 11/06; C09K 2211/00; C09K 2211/10; C09K 2211/1007; C09K 2211/1014; C09K 2211/1029; C09K 2211/1018; C09K 2211/1044; C09K 2211/1059; H01L 51/0032; H01L 51/0003; H01L 51/001; H01L 51/005; H01L 51/006; H01L 51/0067; H01L 51/0071; H01L 51/0072; H01L 51/0073; H01L 51/0074; H01L 51/0096; H01L 51/50; H01L 51/5012; H01L 51/5016; H01L 51/5056;
(Continued)

(56) References Cited

U.S. PATENT DOCUMENTS

2009/0072727 A1* 3/2009 Takeda .................. C09K 11/06
313/504
2015/0159084 A1* 6/2015 Cho ..................... C07D 401/14
252/519.21
2015/0243903 A1 8/2015 Zeng et al.
2016/0197286 A1* 7/2016 Kawamura ............ C09K 11/06
257/40

FOREIGN PATENT DOCUMENTS

WO WO-2014092083 A1 * 6/2014 ............. C09K 11/06
WO 2016/159479 A1 10/2016

OTHER PUBLICATIONS

Cha et al. Dyes and Pigments 2016, 134, 562-568. (Year: 2016).*
Uoyama et al. Nature 2012, 492, 234-240. (Year: 2012).*
Lee et al. Appl. Phys.Lett. 2012, 101, 093306. (Year: 2012).*

* cited by examiner

*Primary Examiner* — Andrew K Bohaty
(74) *Attorney, Agent, or Firm* — Maschoff Brennan

(57) ABSTRACT

The invention relates to an organic molecule, especially for use in optoelectronic components. According to the invention, the organic molecule contains
a first chemical unit having a structure of formula I

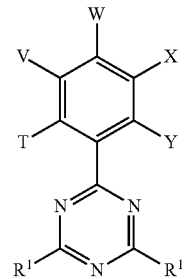

Formula I and
a second chemical unit having a structure of formula II

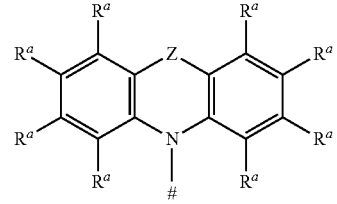

Formula II where the first chemical unit is joined to the second chemical unit via a single bond;
where the following definitions apply:
V is an attachment point of the single bond between the first chemical unit of formula I and the chemical unit or selected from the group consisting of $R^2$, CN;
V is H or an attachment point of the single bond between the first chemical unit of formula I and the chemical unit;
T and W are each an attachment point of the single bond between the first chemical unit and the second chemical unit or selected from the group consisting of $R^2$, CN;
X and Y are each selected from the group consisting of $R^2$ and CN.

14 Claims, 9 Drawing Sheets

(51) Int. Cl.
*C07D 403/10* (2006.01)
*H01L 51/50* (2006.01)
*C07D 403/14* (2006.01)
*H01L 27/32* (2006.01)
*H01L 51/00* (2006.01)
*H01L 51/52* (2006.01)

(52) U.S. Cl.
CPC ...... *H01L 27/3209* (2013.01); *H01L 51/0072* (2013.01); *H01L 51/50* (2013.01); *C09K 2211/1029* (2013.01); *C09K 2211/1059* (2013.01); *H01L 51/5056* (2013.01); *H01L 51/5206* (2013.01); *H01L 51/5221* (2013.01); *Y02E 10/549* (2013.01)

(58) Field of Classification Search
CPC ............. H01L 51/5071; H01L 51/5088; H01L 51/5096; H01L 51/5206; H01L 51/5221; H01L 2251/5376; H01L 27/3209
USPC ....... 428/690, 691, 917, 411.4, 336; 427/58, 427/66; 313/500–512; 257/40, 88–104, 257/E51.001–E51.052; 252/301.16–301.35
See application file for complete search history.

ORGANIC MOLECULES, ESPECIALLY FOR USE IN ORGANIC OPTOELECTRONIC DEVICES

FIELD OF INVENTION

The invention relates to purely organic molecules and to the use thereof in organic light-emitting diodes (OLEDs) and in other organic optoelectronic devices.

SUMMARY

The problem addressed by the present invention was that of providing molecules suitable for use in optoelectronic devices.

This problem is solved by the new class of organic molecules described here.

The organic molecules according to the invention are purely organic molecules, i.e. do not have any metal ions, and are thus delimited from the metal complexes known for use in organic optoelectronic devices.

The organic molecules according to the invention are notable for emissions in the blue, sky blue or green spectral region. The photoluminescence quantum yields of the organic molecules according to the invention are especially 20% or more. The molecules according to the invention especially exhibit thermally activated delayed fluorescence (TADF). The use of the molecules according to the invention in an optoelectronic device, for example an organic light-emitting diode (OLED), leads to higher efficiencies of the device. Corresponding OLEDs have higher stability than OLEDs with known emitter materials and a comparable colour.

The blue spectral region is understood here to mean the visible range from 420 to 470 nm. The sky blue spectral region is understood here to mean the range from 470 nm to 499 nm. The green spectral region is understood here to mean the range from 500 nm to 599 nm. The emission maximum here is within the respective range.

The organic molecules contain a first chemical unit comprising or consisting of a structure of formula I:

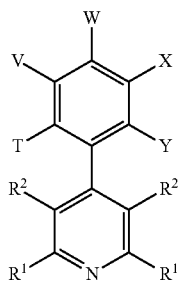

Formula I and
a second chemical unit D having or consisting of a structure of formula II

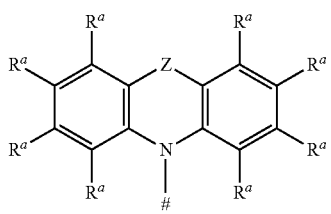

Formula II

In these molecules, the first chemical unit is joined to the second chemical unit D via a single bond.

T is an attachment point of the single bond between the first chemical unit and the second chemical unit D or selected from the group consisting of $R^2$ and CN.

V is H or an attachment point of the single bond between the first chemical unit and the second chemical unit D.

W is an attachment point of the single bond between the first chemical unit and the second chemical unit D or selected from the group consisting of $R^2$ and CN.

X is selected from the group consisting of $R^2$ and CN.

Y is selected from the group consisting of $R^2$ and CN.

# is an attachment point of the single bond between the second chemical unit D and the first chemical unit.

Z is the same or different at each instance and is a direct bond or selected from the group consisting of $CR^3R^4$, $C=CR^3R^4$, $C=O$, $C=NR^3$, $NR^3$, O, $SiR^3R^4$, S, $S(O)$ and $S(O)_2$.

$R^1$ is the same or different at each instance and is H, deuterium, a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium, or an aromatic or heteroaromatic ring system which has 5 to 15 aromatic ring atoms and may be substituted in each case by one or more $R^6$ radicals.

$R^2$ is the same or different at each instance and is H, deuterium, a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium, or an aromatic or heteroaromatic ring system which has 5 to 15 aromatic ring atoms and may be substituted in each case by one or more $R^6$ radicals.

$R^a$, $R^3$ and $R^4$ is the same or different at each instance and is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)$ $(R^5)$, SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals.

$R^5$ is the same or different at each instance and is H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^6$ radicals, where one or more nonadjacent $CH_2$ groups may be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)$ $(R^6)$, SO, $SO_2$, $NR^6$, O, S or $CONR^6$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^6$ radicals, or an aryloxy or heteroaryloxy group which has 5 to 60 aromatic ring atoms and may be substituted in each case by one or more $R^6$ radicals, or a diarylamino group, diheteroarylamino group or arylheteroarylamino group which has 10 to 40 aromatic ring atoms and may be substituted in each case by one or more $R^6$ radicals.

$R^6$ is the same or different at each instance and is H, deuterium, OH, $CF_3$, CN, F, a linear alkyl, alkoxy or thioalkoxy group having 1 to 5 carbon atoms or a linear alkenyl or alkynyl group having 2 to 5 carbon atoms or a branched or cyclic alkyl, alkenyl, alkynyl, alkoxy or thioalkoxy group having 3 to 5 carbon atoms, where one or more hydrogen atoms may be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

Each of the $R^a$, $R^3$, $R^4$ or $R^5$ radicals together with one or more further $R^a$, $R^3$, $R^4$ or $R^5$ radicals may form a mono- or polycyclic, aliphatic, aromatic and/or benzofused ring system.

Exactly one radical selected from the group consisting of T, W, X and Y is CN and exactly one radical selected from the group consisting of T, V and W in the attachment point of the single bond between the first chemical unit of formula I and the second chemical unit D.

According to the invention, W is H when T is CN and V is the attachment point of the single bond between the first chemical unit and the second chemical unit D.

The organic molecules according to the invention are notable for features including good thermal stability and sublimability, and more particularly are stable on vapour deposition within the context of production of an optoelectronic device (for example of an OLED).

In one embodiment, $R^1$ is the same or different at each instance and is methyl or phenyl.

In one embodiment, $R^2$ is the same or different at each instance and is H, methyl or phenyl.

In one embodiment, $R^2$ is H at each instance.

In one embodiment, W is CN.

In one embodiment, X is CN.

In one embodiment, X is CN and T is the attachment point of the single bond between the first chemical unit and the second chemical unit D.

In a further embodiment of the organic molecules, the second chemical group D comprises a structure of the formula IIa or consists of a structure of the formula IIa:

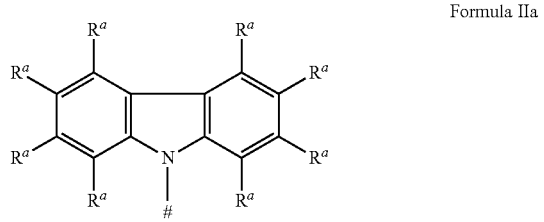

Formula IIa where the definitions for formula I and II are applicable to # and $R^a$.

In a further embodiment of the organic molecules according to the invention, the second chemical unit D comprises or consists of a structure of the formula IIb, of the formula IIb-2, of the formula IIb-3 or of the formula IIb-4:

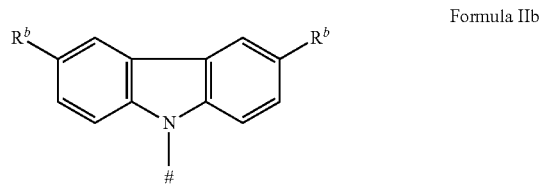

Formula IIb

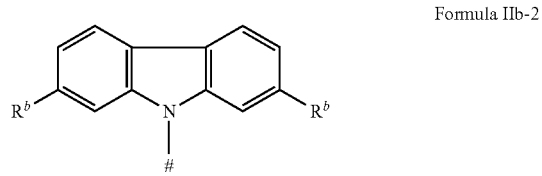

Formula IIb-2

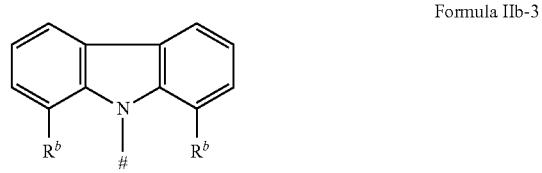

Formula IIb-3

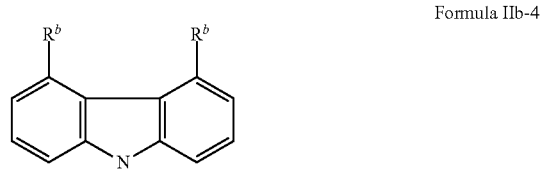

Formula IIb-4 where $R^b$ is the same or different at each instance and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, C≡C, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals. For the rest, the definitions given above are applicable.

In a further embodiment of the organic molecules according to the invention, the second chemical unit D comprises or consists of a structure of the formula IIc, of the formula IIc-2, of the formula IIc-3 or of the formula IIc-4:

Formula IIc

Formula IIc-2

Formula IIc-3

Formula IIc-4 where the definitions given above are applicable.

In a further embodiment of the organic molecules according to the invention, $R^b$ independently at each instance is selected from the group consisting of Me, $^i$Pr, $^t$Bu, CN, CF$_3$, Ph which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, carbazolyl which may be substituted in each case by one or more radicals selected from Me, $^i$Pr, $^t$Bu, CN, CF$_3$ and Ph, triazinyl which may be substituted in each case by one or more radicals selected from Me, $^i$Pr, $^t$Bu, CN, CF$_3$ and Ph, and N(Ph)$_2$.

In a further embodiment of the organic molecules according to the invention, $R^b$ at each instance is independently selected from the group consisting of Me, $^i$Pr, $^t$Bu, CN, CF$_3$, Ph, which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, and triazinyl which may be substituted in each case by one or more radicals selected from Me, $^i$Pr, $^t$Bu, CN, CF$_3$ and Ph.

In a further embodiment, $R^b$ at each instance is independently selected from the group consisting of Me, $^t$Bu, CN, CF$_3$ and Ph, which may be substituted in each case by one or more radicals selected from the group consisting of Me, $^i$Pr, $^t$Bu, CN, CF$_3$ and Ph.

The following are examples of the second chemical group D:

-continued
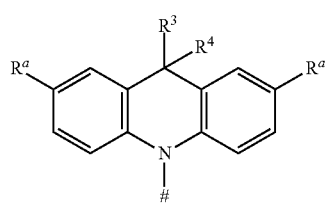
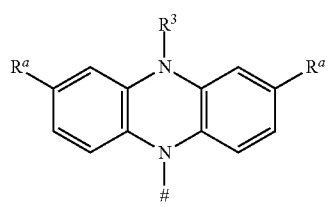
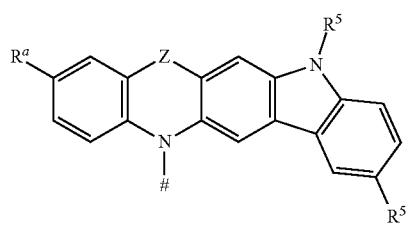
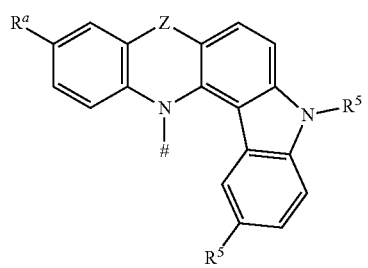
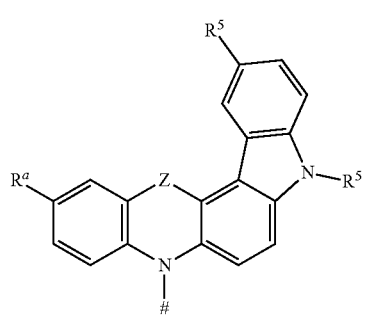
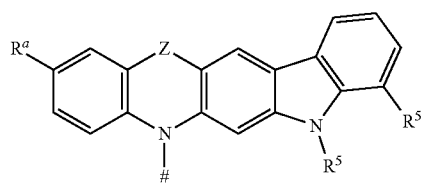
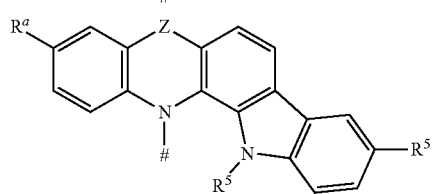
-continued
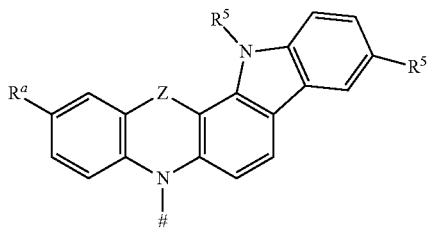
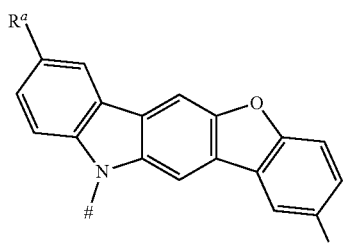
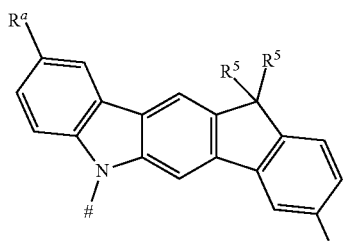
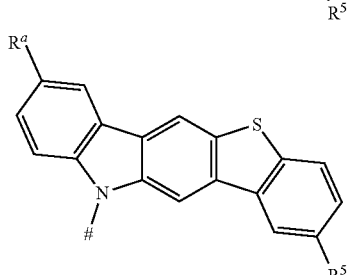
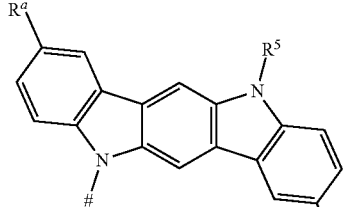
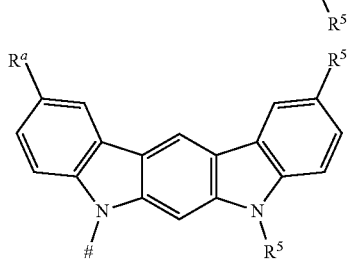
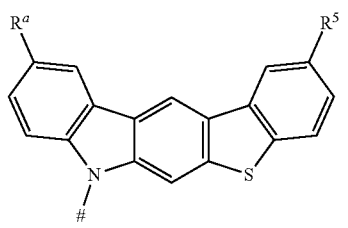

-continued
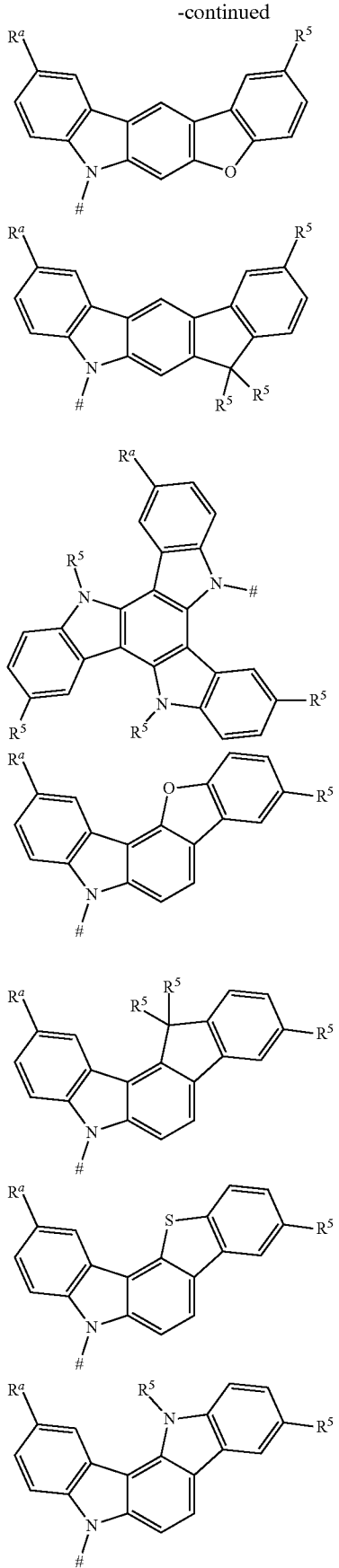
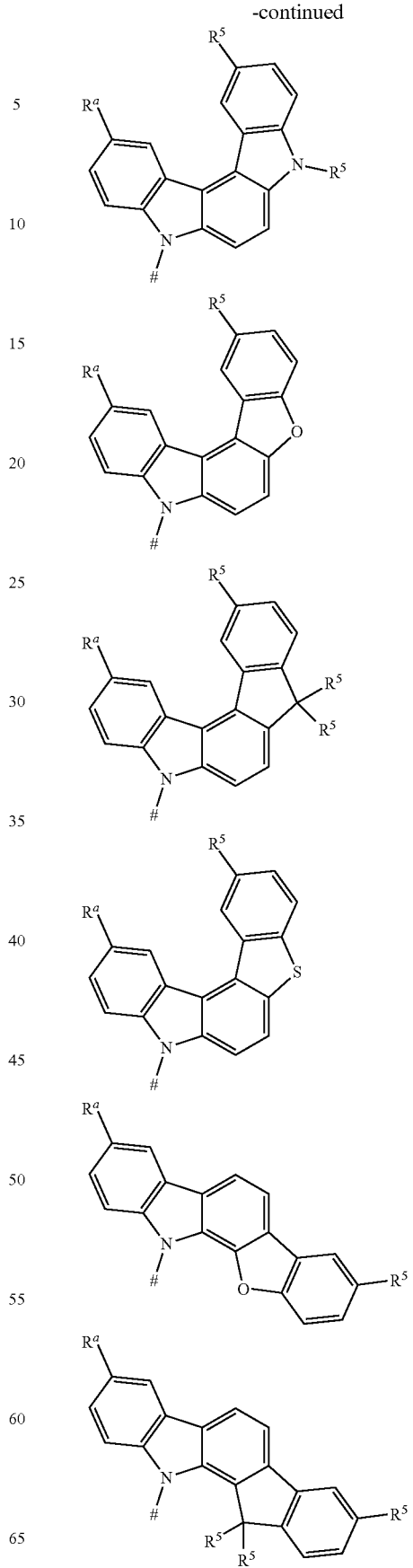

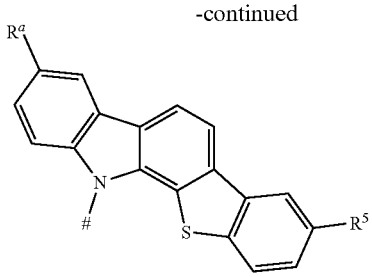

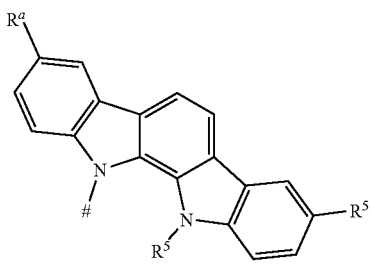

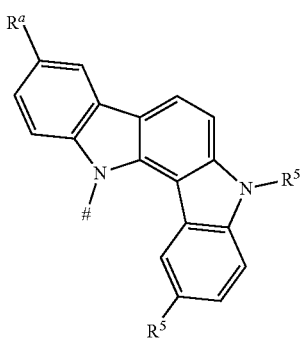

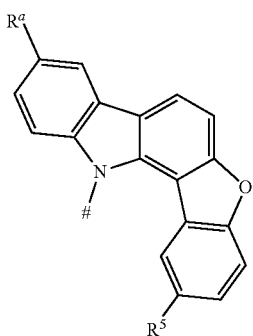

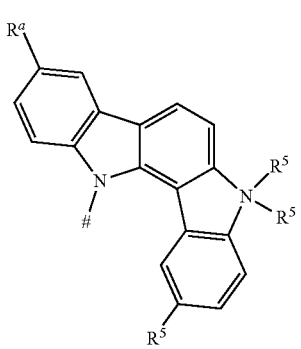

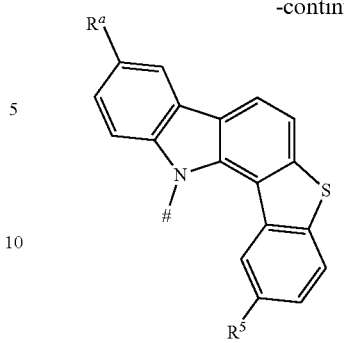

where the definitions given above are applicable to #, Z, $R^a$, $R^3$, $R^4$ and $R^5$. In one embodiment, the $R^5$ radical is the same or different at each instance and is selected from the group consisting of H, methyl, ethyl, phenyl and mesityl.

In one embodiment, $R^a$ is the same or different at each instance and is selected from the group consisting of H, methyl (Me), i-propyl ($CH(CH_3)_2$) ($^{i}Pr$), t-butyl ($^{t}Bu$), phenyl (Ph), CN, $CF_3$ and diphenylamine ($NPh_2$).

In one embodiment, the organic molecules according to the invention comprise or consist of a structure of the formula III:

Formula III

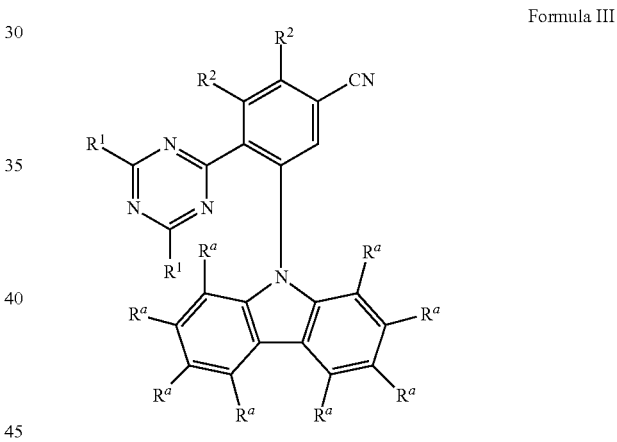

where the definitions given above are applicable.

In a further embodiment, the organic molecules according to the invention comprise or consist of a structure of the formula IIIa:

Formula IIIa

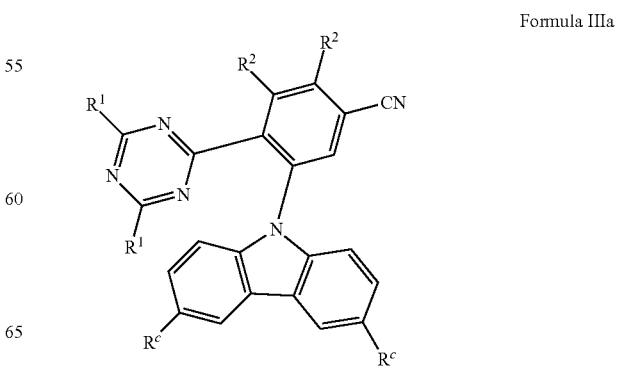

where R$^c$ independently at each instance is selected from the group consisting of Me, $^i$Pr, $^t$Bu, CN, CF$_3$, Ph which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, carbazolyl which may be substituted in each case by one or more radicals selected from Me, $^i$Pr, $^t$Bu, CN, CF$_3$ and Ph, triazinyl which may be substituted in each case by one or more radicals selected from Me, $^i$Pr, $^t$Bu, CN, CF$_3$ and Ph, and N(Ph)$_2$ and otherwise the definitions given above are applicable.

In a further embodiment, the organic molecules according to the invention comprise or consist of a structure of the formula IIIb:

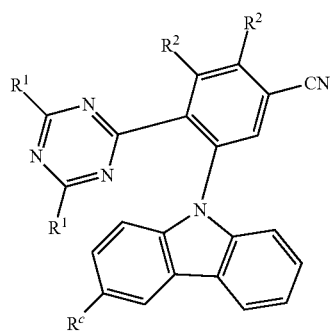

Formula IIIb where the definitions given above are applicable.

In a further embodiment, the organic molecules according to the invention comprise or consist of a structure of the formula IIIc:

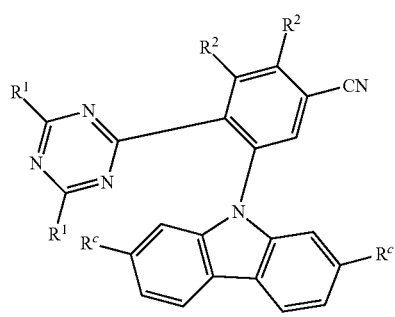

Formula IIIc where the definitions given above are applicable.

In a further embodiment, the organic molecules according to the invention comprise or consist of a structure of the formula IIId:

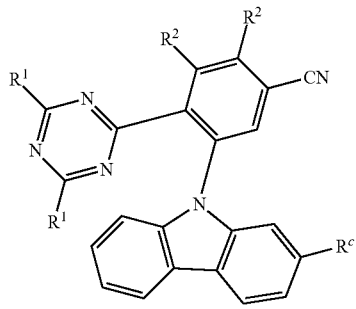

Formula IIId where the definitions given above are applicable.

In a further embodiment, the organic molecules according to the invention comprise or consist of a structure of the formula IIIe:

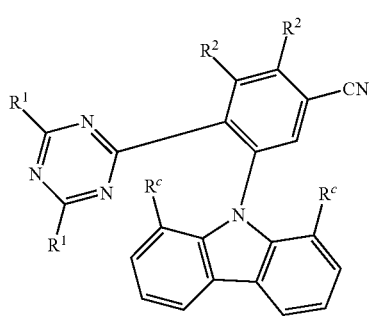

Formula IIIe where the definitions given above are applicable.

In a further embodiment, the organic molecules according to the invention comprise a structure of the formula IIIf or consist of this structure:

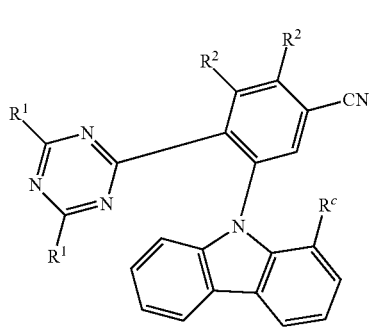

Formula IIIf where the definitions given above are applicable.

In a further embodiment, the organic molecules according to the invention comprise or consist of a structure of the formula IIIg:

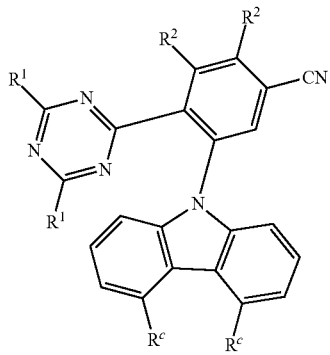

Formula IIIg where the definitions given above are applicable.

In a further embodiment, the organic molecules according to the invention comprise a structure of the formula IIIh or consist of this structure:

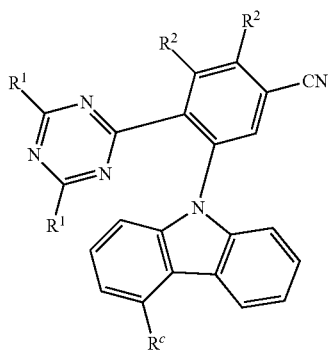

Formula IIIh where the definitions given above are applicable.

In one embodiment, the organic molecules according to the invention comprise or consist of a structure of the formula IV:

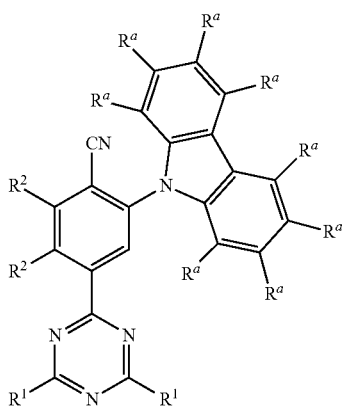

Formula IV where the definitions given above are applicable.

In a further embodiment, the organic molecules according to the invention comprise a structure of the formula IVa:

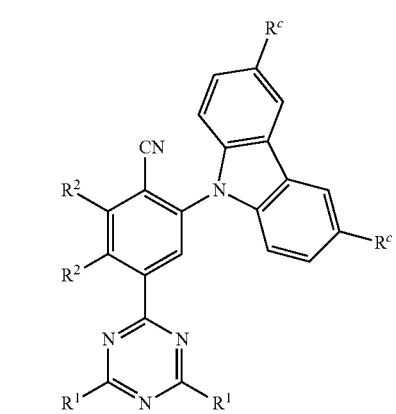

Formula IVa where the definitions given above are applicable.

In a further embodiment, the organic molecules according to the invention comprise or consist of a structure of the formula IVb:

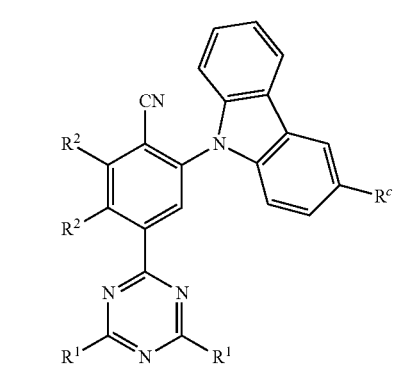

Formula IVb where the definitions given above are applicable.

In a further embodiment, the organic molecules according to the invention comprise or consist of a structure of the formula IVc:

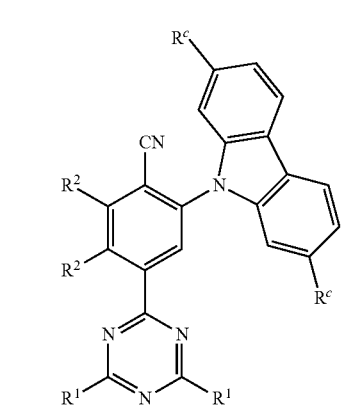

Formula IVc where the definitions given above are applicable.

In a further embodiment, the organic molecules according to the invention comprise or consist of a structure of the formula IVd:

Formula IVd

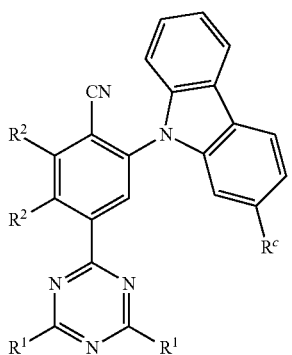

where the definitions given above are applicable.

In a further embodiment, the organic molecules according to the invention comprise or consist of a structure of the formula IVe:

Formula IVe

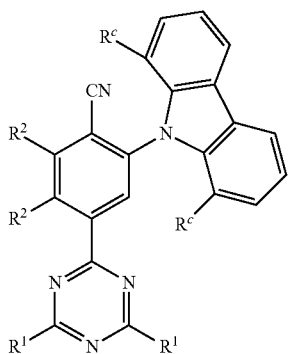

where the definitions given above are applicable.

In a further embodiment, the organic molecules according to the invention comprise or consist of a structure of the formula IVf:

Formula IVf

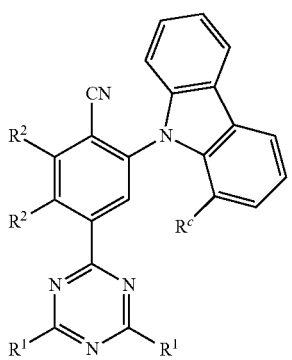

where the definitions given above are applicable.

In a further embodiment, the organic molecules according to the invention comprise or consist of a structure of the formula IVg:

Formula IVg

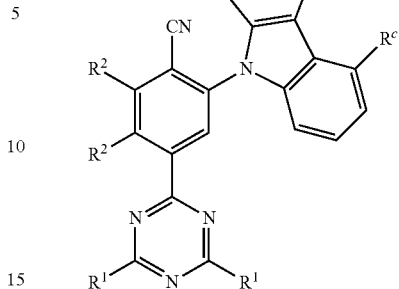

where the definitions given above are applicable.

In a further embodiment, the organic molecules according to the invention comprise or consist of a structure of the formula IVh:

Formula IVh

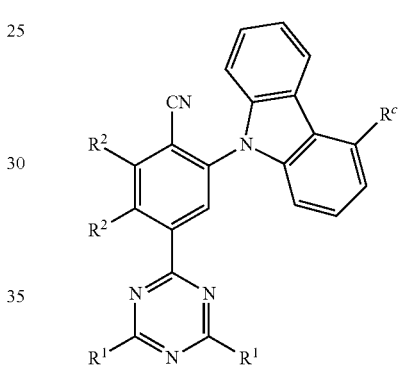

where the definitions given above are applicable.

In one embodiment, the organic molecules according to the invention comprise or consist of a structure of the formula V:

Formula V

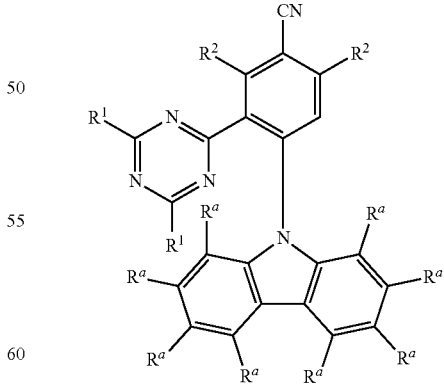

where the definitions given above are applicable.

In a further embodiment, the organic molecules according to the invention comprise or consist of a structure of the formula Va:

Formula Va

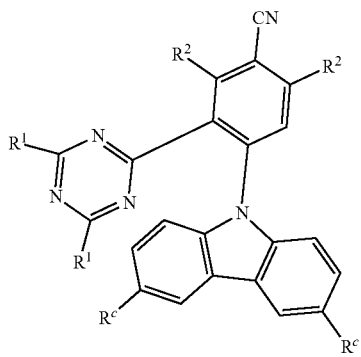

where the definitions given above are applicable.

In a further embodiment, the organic molecules according to the invention comprise or consist of a structure of the formula Vb:

Formula Vb

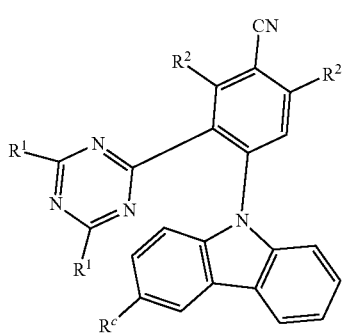

where the definitions given above are applicable.

In a further embodiment, the organic molecules according to the invention comprise or consist of a structure of the formula Vc:

Formula Vc

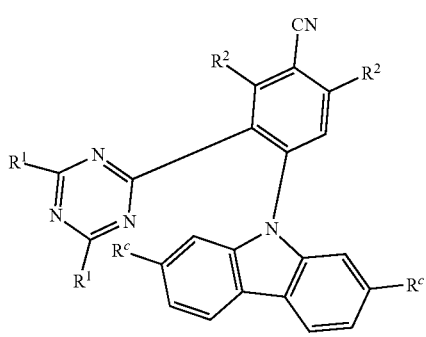

where the definitions given above are applicable.

In a further embodiment, the organic molecules according to the invention comprise or consist of a structure of the formula Vd:

Formula Vd

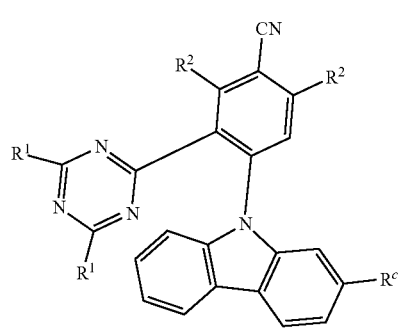

where the definitions given above are applicable.

In a further embodiment, the organic molecules according to the invention comprise or consist of a structure of the formula Ve:

Formula Ve

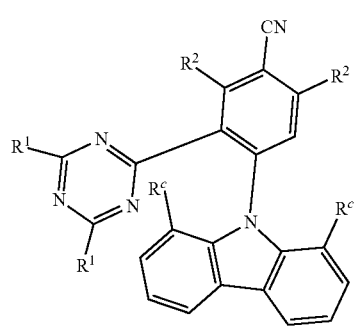

where the definitions given above are applicable.

In a further embodiment, the organic molecules according to the invention comprise a structure of the formula Vf or consist of this structure:

Formula Vf

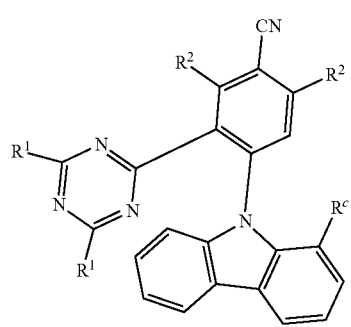

where the definitions given above are applicable.

In a further embodiment, the organic molecules according to the invention comprise or consist of a structure of the formula Vg:

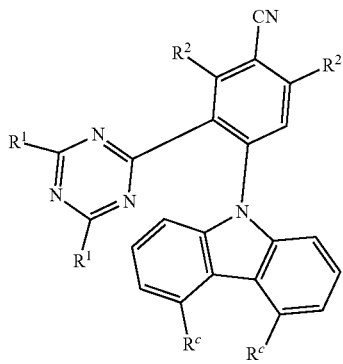

Formula Vg where the definitions given above are applicable.

In a further embodiment, the organic molecules according to the invention comprise a structure of the formula Vh or consist of this structure:

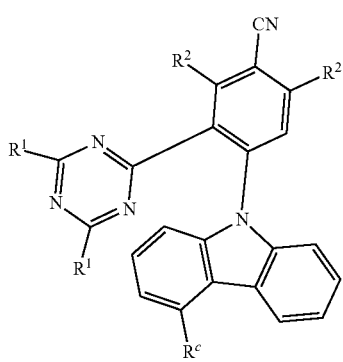

Formula Vh where the definitions given above are applicable.

In one embodiment, the organic molecules according to the invention comprise or consist of a structure of the formula VI:

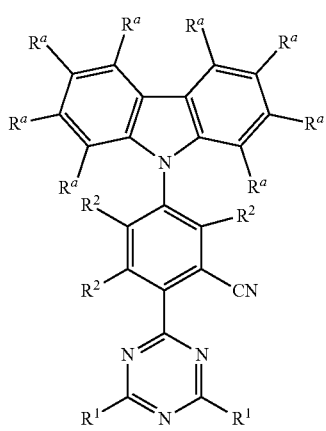

Formula VI where the definitions given above are applicable.

In a further embodiment, the organic molecules according to the invention comprise or consist of a structure of the formula VIa:

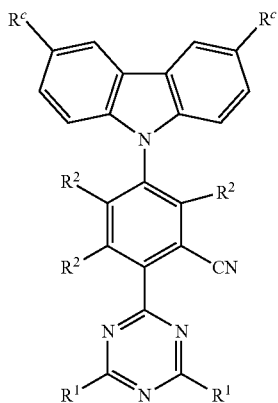

Formula VIa where the definitions given above are applicable.

In a further embodiment, the organic molecules according to the invention comprise or consist of a structure of the formula VIb:

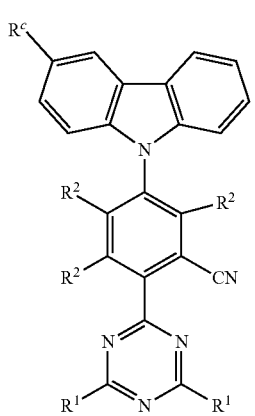

Formula VIb where the definitions given above are applicable.

In a further embodiment, the organic molecules according to the invention comprise or consist of a structure of the formula VIc:

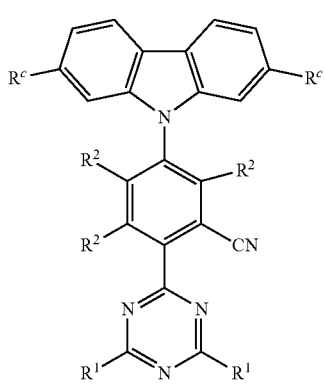

Formula VIc where the definitions given above are applicable.

In a further embodiment, the organic molecules according to the invention comprise or consist of a structure of the formula VId:

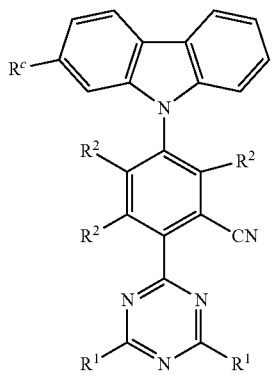

Formula VId where the definitions given above are applicable.

In a further embodiment, the organic molecules according to the invention comprise a structure of the formula VIe or consist of this structure:

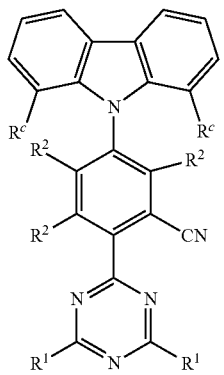

Formula VIe where the definitions given above are applicable.

In a further embodiment, the organic molecules according to the invention comprise or consist of a structure of the formula VIf:

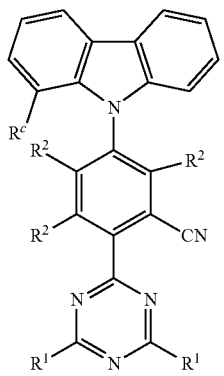

Formula VIf where the definitions given above are applicable.

In a further embodiment, the organic molecules according to the invention comprise or consist of a structure of the formula VIg:

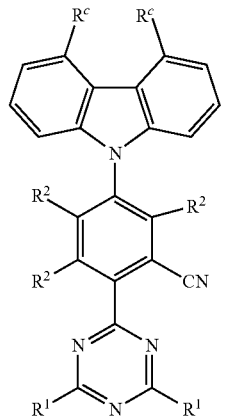

Formula VIg where the definitions given above are applicable.

In a further embodiment, the organic molecules according to the invention comprise or consist of a structure of the formula VIh:

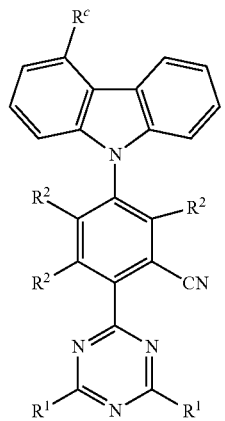

Formula VIh where the definitions given above are applicable.

In one embodiment, the organic molecules according to the invention comprise or consist of a structure of the formula VII:

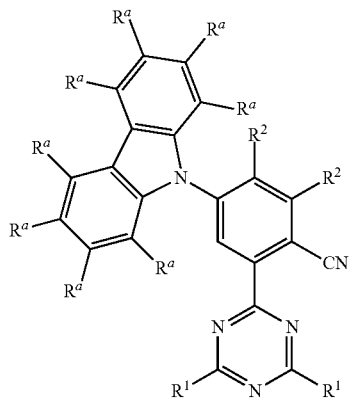

Formula VII where the definitions given above are applicable.

In a further embodiment, the organic molecules according to the invention comprise or consist of a structure of the formula VIIa:

Formula VIIa

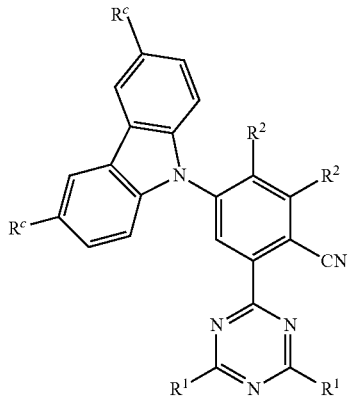

where the definitions given above are applicable.

In a further embodiment, the organic molecules according to the invention comprise or consist of a structure of the formula VIIb:

Formula VIIb

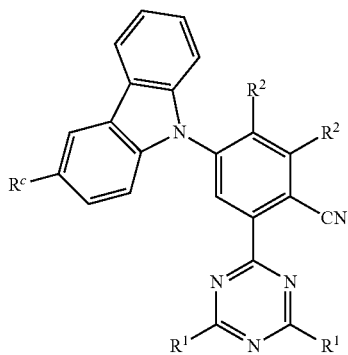

where the definitions given above are applicable.

In a further embodiment, the organic molecules according to the invention comprise or consist of a structure of the formula VIIc:

Formula VIIc

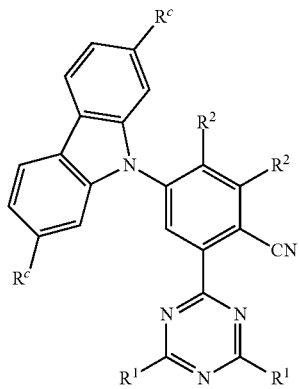

where the definitions given above are applicable.

In a further embodiment, the organic molecules according to the invention comprise or consist of a structure of the formula VIId:

Formula VIId

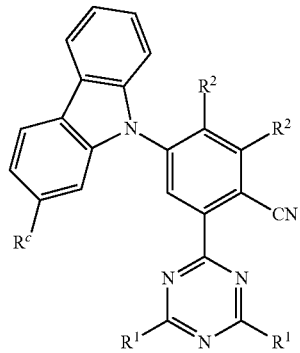

where the definitions given above are applicable.

In a further embodiment, the organic molecules according to the invention comprise a structure of the formula VIIe or consist of this structure:

Formula VIIe

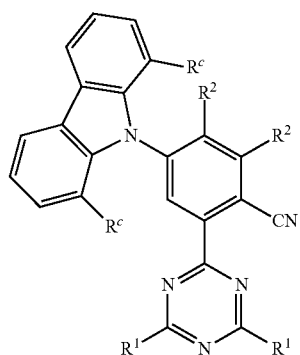

where the definitions given above are applicable.

In a further embodiment, the organic molecules according to the invention comprise or consist of a structure of the formula VIIf:

Formula VIIf

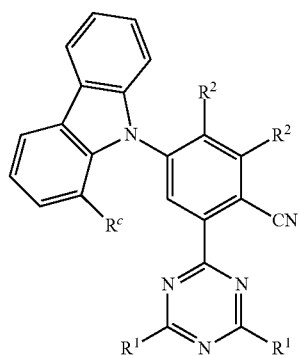

where the definitions given above are applicable.

In a further embodiment, the organic molecules according to the invention comprise or consist of a structure of the formula VIIg:

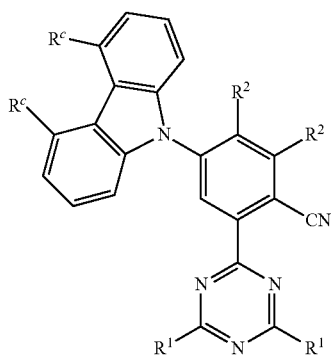

Formula VIIg where the definitions given above are applicable.

In a further embodiment, the organic molecules according to the invention comprise or consist of a structure of the formula VIIh:

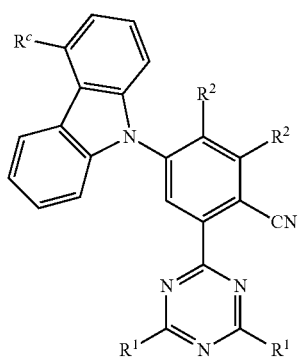

Formula VIIh where the definitions given above are applicable.

In one embodiment, the organic molecules according to the invention comprise or consist of a structure of the formula VIII:

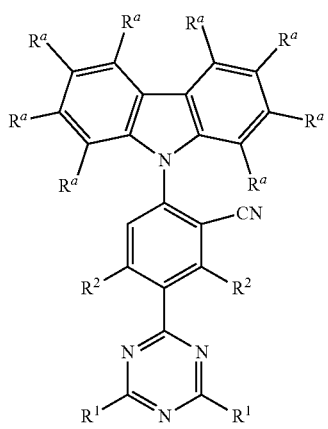

Formula VIII where the definitions given above are applicable.

In a further embodiment, the organic molecules according to the invention comprise or consist of a structure of the formula VIIIa:

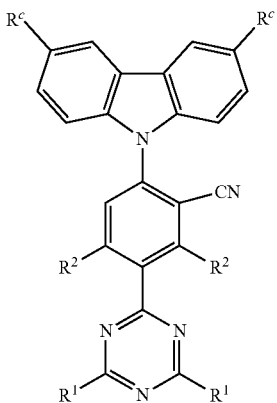

Formula VIIIa where the definitions given above are applicable.

In a further embodiment, the organic molecules according to the invention comprise or consist of a structure of the formula VIIIb:

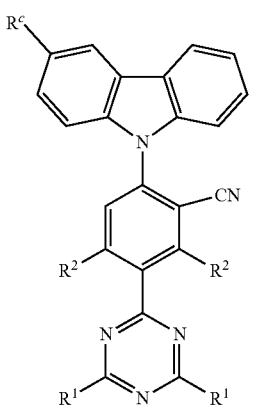

Formula VIIIb where the definitions given above are applicable.

In a further embodiment, the organic molecules according to the invention comprise or consist of a structure of the formula VIIIc:

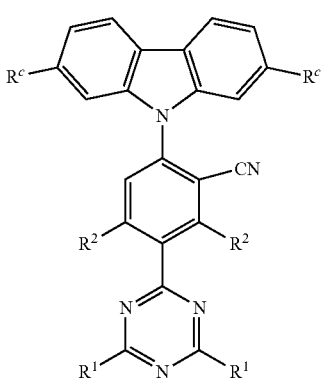

Formula VIIIc where the definitions given above are applicable.

In a further embodiment, the organic molecules according to the invention comprise or consist of a structure of the formula VIIId:

Formula VIIId

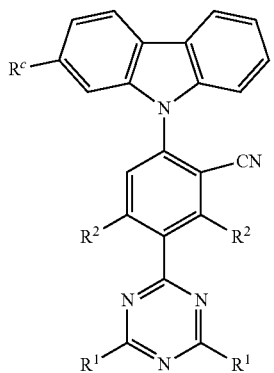

where the definitions given above are applicable.

In a further embodiment, the organic molecules according to the invention comprise a structure of the formula VIIIe or consist of this structure:

Formula VIIIe

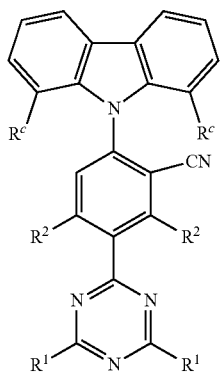

where the definitions given above are applicable.

In a further embodiment, the organic molecules according to the invention comprise or consist of a structure of the formula VIIIf:

Formula VIIIf

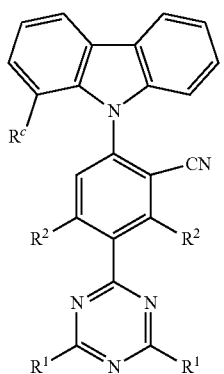

where the definitions given above are applicable.

In a further embodiment, the organic molecules according to the invention comprise or consist of a structure of the formula VIIIg:

Formula VIIIg

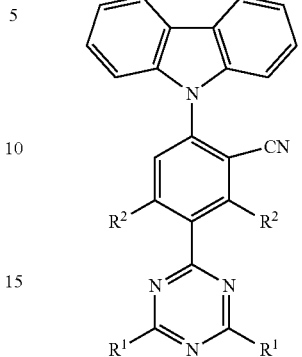

where the definitions given above are applicable.

In a further embodiment, the organic molecules according to the invention comprise or consist of a structure of the formula VIIIh:

Formula VIIIh

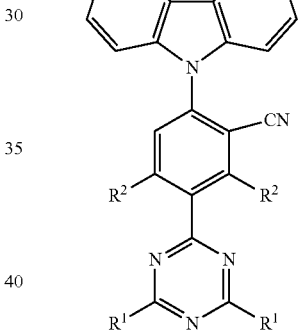

where the definitions given above are applicable.

In one embodiment, the organic molecules according to the invention comprise or consist of a structure of the formula IX:

Formula IX

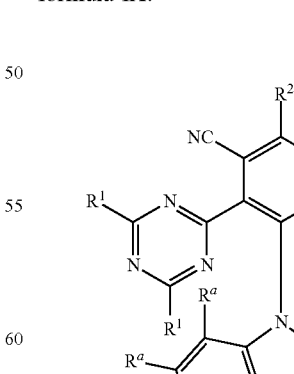

where the definitions given above are applicable.

In a further embodiment, the organic molecules according to the invention comprise or consist of a structure of the formula IXa:

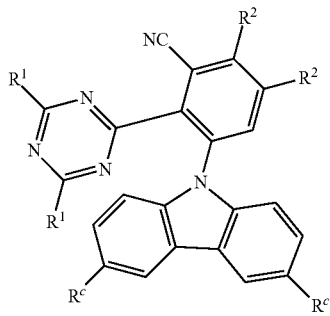

Formula IXa where the definitions given above are applicable.

In a further embodiment, the organic molecules according to the invention comprise or consist of a structure of the formula IXb:

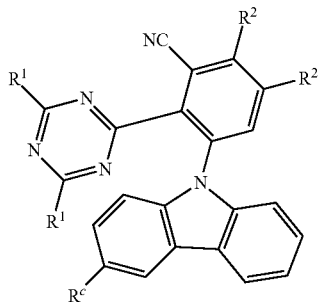

Formula IXb where the definitions given above are applicable.

In a further embodiment, the organic molecules according to the invention comprise or consist of a structure of the formula IXc:

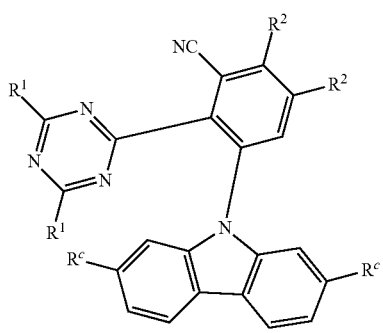

Formula IXc where the definitions given above are applicable.

In a further embodiment, the organic molecules according to the invention comprise or consist of a structure of the formula IXd:

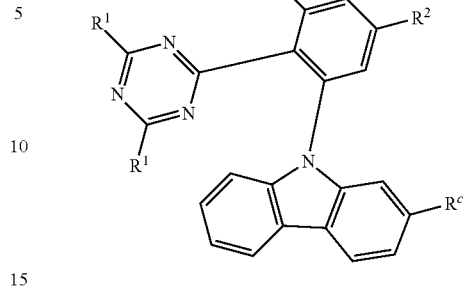

Formula IXd where the definitions given above are applicable.

In a further embodiment, the organic molecules according to the invention comprise or consist of a structure of the formula IXe:

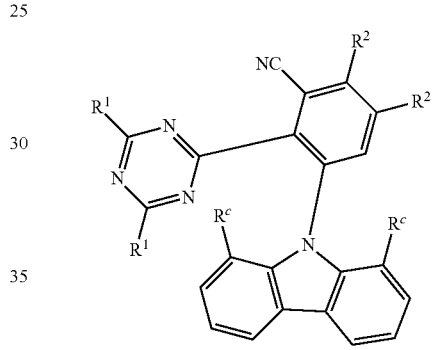

Formula IXe where the definitions given above are applicable.

In a further embodiment, the organic molecules according to the invention comprise a structure of the formula IXf or consist of this structure:

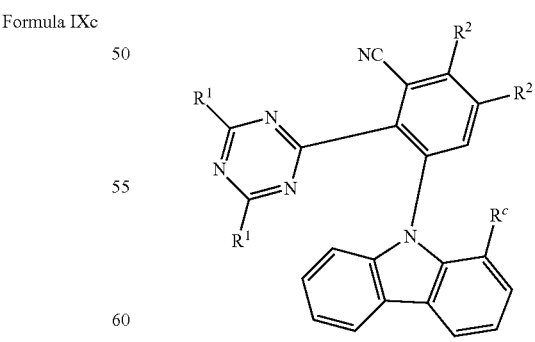

Formula IXf where the definitions given above are applicable.

In a further embodiment, the organic molecules according to the invention comprise or consist of a structure of the formula IXg:

Formula IXg

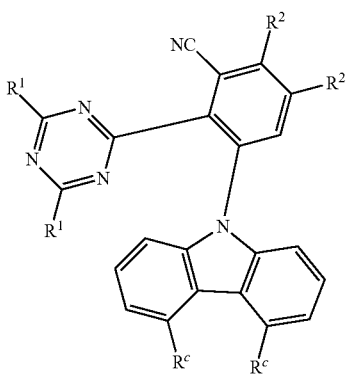

where the definitions given above are applicable.

In a further embodiment, the organic molecules according to the invention comprise a structure of the formula IXh or consist of this structure:

Formula IXh

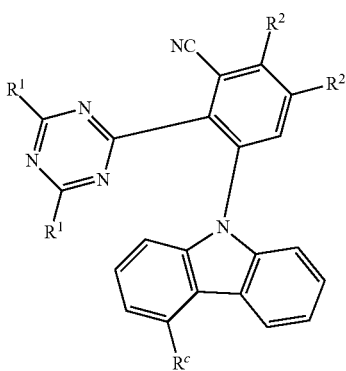

where the definitions given above are applicable.

In a further embodiment of the organic molecules according to the invention, $R^c$ independently at each instance is selected from the group consisting of Me, $^i$Pr, $^t$Bu, CN, CF$_3$, Ph, which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, and triazinyl which may be substituted in each case by one or more radicals selected from Me, $^i$Pr, $^t$Bu, CN, CF$_3$ and Ph.

In a further embodiment, $R^c$ at each instance is independently selected from the group consisting of Me, $^t$Bu, CN, CF$_3$, Ph, which may be substituted in each case by one or more radicals selected from Me, $^i$Pr, $^t$Bu, CN, CF$_3$ and Ph, and triazinyl which may be substituted in each case by one or more radicals selected from Me, $^i$Pr, $^t$Bu, CN, CF$_3$ and Ph.

In a further embodiment, $R^c$ at each instance is independently selected from the group consisting of Me, $^t$Bu, CN, CF$_3$ and Ph, which may be substituted in each case by one or more radicals selected from Me, $^i$Pr, $^t$Bu, CN, CF$_3$ and Ph.

In the context of this invention, an aryl group contains 6 to 60 aromatic ring atoms; a heteroaryl group contains 5 to 60 aromatic ring atoms, of which at least one is a heteroatom. The heteroatoms are especially N, O and/or S. If, in the description of particular embodiments of the invention, other definitions departing from the definition mentioned are given, for example with regard to the number of aromatic ring atoms or of heteroatoms present, these are applicable.

An aryl group or heteroaryl group is understood to mean a simple aromatic cycle, i.e. benzene, or a simple heteroaromatic cycle, for example pyridine, pyrimidine or thiophene, or a heteroaromatic polycycle, for example phenanthrene, quinoline or carbazole. A fused (annelated) aromatic or heteroaromatic polycycle in the context of the present application consists of two or more mutually condensed simple aromatic or heteroaromatic cycles.

An aryl or heteroaryl group which may be substituted in each case by the abovementioned radicals and which may be joined via any desired positions to the aromatic or heteroaromatic system is especially understood to mean groups derived from benzene, naphthalene, anthracene, phenanthrene, pyrene, dihydropyrene, chrysene, perylene, fluoranthene, benzanthracene, benzphenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, 1,3,5-triazine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the groups mentioned.

A cyclic alkyl, alkoxy or thioalkoxy group is understood here to mean a monocyclic, bicyclic or polycyclic group.

In the context of the present invention, a $C_1$- to $C_{40}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]-octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

One embodiment of the invention relates to organic molecules having a $\Delta E(S_1-T_1)$ value between the lowermost excited singlet state ($S_1$) and the triplet state ($T_1$) below it of not higher than 5000 cm$^{-1}$, especially not higher than 3000 cm$^{-1}$, or not higher than 1500 cm$^{-1}$ or 1000 cm$^{-1}$, and/or an emission lifetime of not more than 150 µs, especially of not more than 100 µs, of not more than 50 µs, or of not more than 10 µs, and/or a main emission band having a half-height width of less than 0.55 eV, especially less than 0.50 eV, less than 0.48 eV, or less than 0.45 eV.

In particular, the organic molecules have an emission maximum between 420 and 500 nm, between 430 and 480 nm, or between 450 and 470 nm.

In particular, the molecules have a blue material index (BMI), the quotient of the PLQY (in %) and its CIE$_y$ colour coordinates of the light emitted by the molecule according to the invention, of greater than 150, especially of greater than 200, of greater than 250 or of greater than 300.

In a further aspect, the invention relates to a process for preparing an organic molecule according to the invention of the type described here (with an optional further conversion), wherein a 4- and 6-R$^1$-substituted 2-halo-1,3,5-triazine is used as reactant. 2-Halo-1,3,5-triazines according to the invention are 2-chloro-1,3,5-triazine, 2-bromo-1,3,5-triazine and 2-iodo-1,3,5-triazine.

In one embodiment, 2-chloro-4,6-diphenyl-1,3,5-triazine, 2-bromo-4,6-diphenyl-1,3,5-triazine, 2-iodo-4,6-diphenyl-1,3,5-triazine, 2-chloro-4,6-dimethyl-1,3,5-triazine, 2-bromo-4,6-dimethyl-1,3,5-triazine or 2-iodo-4,6-dimethyl-1,3,5-triazine is used as reactant.

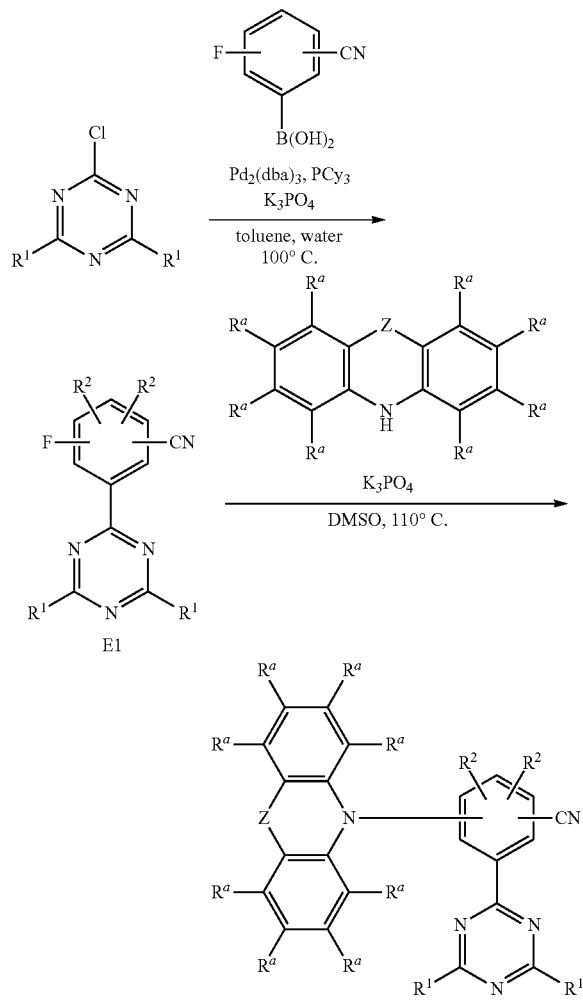

In one embodiment, 4- and 6-R$^1$-substituted 2-halo-1,3,5-triazine as reactant is reacted with a fluorocyanophenylboronic acid or a corresponding fluorocyanophenylboronic ester in a palladium-catalysed cross-coupling reaction. It is possible here in accordance with the invention to use, by way of example, 2-fluoro-4-cyanophenylboronic acid, 2-fluoro-5-cyanophenylboronic acid, 2-fluoro-6-cyanophenylboronic acid, 3-fluoro-4-cyano-phenylboronic acid, 3-fluoro-5-cyanophenylboronic acid, 3-fluoro-6-cyanophenylboronic acid, 4-fluoro-3-cyanophenylboronic acid and 4-fluoro-2-cyanophenylboronic acid. The product is obtained by deprotonation of the corresponding amine, followed by nucleophilic substitution of the fluorine group. In this case, one nitrogen heterocycle is reacted with a reactant E1 in the manner of a nucleophilic aromatic substitution. Typical conditions include the use of a base, for example tribasic potassium phosphate or sodium hydride, in an aprotic polar solvent, for example dimethyl sulphoxide (DMSO) or N,N-dimethylformamide (DMF).

In a further aspect, the invention relates to the use of the organic molecules as luminescent emitters or as host material in an organic optoelectronic device, especially where the organic optoelectronic device is selected from the group consisting of:

organic light-emitting diodes (OLEDs),
light-emitting electrochemical cells,
OLED sensors, especially in gas and vapour sensors not hermetically shielded from the outside,
organic diodes,
organic solar cells,
organic transistors,
organic field-effect transistors,
organic lasers and
down-conversion elements.

In a further aspect, the invention relates to a composition comprising or consisting of:

(a) at least one organic molecule according to the invention, especially as emitter and/or host, and (b) at least one, i.e. one or more, emitter and/or host material(s) other than the organic molecule according to the invention, and (c) optionally one or more dyes and/or one or more organic solvents.

In one embodiment, the composition according to the invention consists of an organic molecule according to the invention and one or more host materials. The host material(s) especially has/have triplet ($T_1$) and singlet ($S_1$) energy levels at higher energy than the triplet ($T_1$) and singlet ($S_1$) energy levels of the organic molecule according to the invention. In one embodiment, the composition, as well as the organic molecule according to the invention, includes an electron-dominant and a hole-dominant host material. The highest occupied orbital (HOMO) and the lowest unoccupied orbital (LUMO) of the hole-dominant host material are especially at higher energy than those of the electron-dominant host material. The HOMO of the hole-dominant host material is at lower energy than the HOMO of the organic molecule according to the invention, while the LUMO of the electron-dominant host material is at higher energy than the LUMO of the organic molecule according to the invention. In order to avoid exciplex formation between emitter and host material(s), the materials should be chosen such that the energy gaps between the respective orbitals are small. The gap between the LUMO of the electron-dominant host material and the LUMO of the organic molecule according to the invention is especially less than 0.5 eV, preferably less than 0.3 eV, even more preferably less than 0.2 eV. The gap between the HOMO of the hole-dominant host material and the HOMO of the organic molecule according to the invention is especially less than 0.5 eV, preferably less than 0.3 eV, even more preferably less than 0.2 eV.

In a further aspect, the invention relates to an organic optoelectronic device including an organic molecule according to the invention or a composition according to the invention. The organic optoelectronic device especially takes the form of a device selected from the group consisting of organic light-emitting diode (OLED); light-emitting electrochemical cell; OLED sensor, especially gas and vapour sensors that are not hermetically shielded from the outside; organic diode; organic solar cell; organic transistor; organic field effect transistor; organic laser and down-conversion element.

An organic optoelectronic device comprising:
a substrate,
an anode and
a cathode, where the anode or cathode has been applied to the substrate, and
at least one light-emitting layer which is arranged between anode and cathode and comprises an organic molecule according to the invention is a further embodiment of the invention.

In one embodiment, the optoelectronic device is an OLED. A typical OLED has, for example, the following layer structure:
1. Substrate (carrier material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

Individual layers here are present merely in an optional manner. In addition, two or more of these layers may be combined. And it is possible for individual layers to be present more than once in the component.

In one embodiment, at least one electrode of the organic component is translucent. "Translucent" refers here to a layer which is transparent to visible light. The translucent layer here may be clear and see-through, i.e. transparent, or at least partly light-absorbing and/or partly light-scattering, such that the translucent layer, for example, may also have a diffuse or milky appearance. More particularly, a layer referred to here as translucent is very substantially transparent, such that, in particular, the absorption of light is as low as possible.

In a further embodiment, the organic component, especially an OLED, has an inverted structure. It is a feature of the inverted structure that the cathode is on the substrate and the other layers are applied in a correspondingly inverted manner.
1. Substrate (carrier material)
2. Cathode
3. Electron injection layer (EIL)
4. Electron transport layer (ETL)
5. Hole blocking layer (HBL)
6. Emission layer/emitting layer (EML)
7. Electron blocking layer (EBL)
8. Hole transport layer (HTL)
9. Hole injection layer (HIL)
10. Anode Individual layers here are present merely in an optional manner. In addition, two or more of these layers may be combined. And it is possible for individual layers to be present more than once in the component.

In one embodiment, in the inverted OLED, the anode layer of the typical structure, for example an ITO (indium tin oxide) layer, is connected as the cathode.

In a further embodiment, the organic component, especially an OLED, has a stacked structure. The individual OLEDs here are arranged one on top of another and not one alongside another as usual. A stacked structure can enable the generation of mixed light. For example, this structure can be used in the generation of white light, which is produced by forming the entire visible spectrum, typically by the combination of the emitted light from blue, green and red emitters. In addition, with practically the same efficiency and identical luminance, it is possible to achieve significantly longer lifetimes compared to standard OLEDs. For the stacked structure, it is optionally possible to use what is called a charge generation layer (CGL) between two OLEDs. This consists of an n-doped layer and a p-doped layer, the n-doped layer typically being applied closer to the anode.

In one embodiment—called a tandem OLED—two or more emission layers occur between the anode and cathode. In one embodiment, three emission layers are arranged one on top of another, where one emission layer emits red light, one emission layer emits green light and one emission layer emits blue light, and there are optionally further charge generation, blocker or transport layers applied between the individual emission layers. In a further embodiment, the respective emission layers are applied in a directly adjacent manner. In a further embodiment, there is one charge generation layer in each case between the emission layers. In addition, in an OLED, it is possible to combine directly adjacent emission layers and emission layers separated by charge generation layers.

It is also possible to arrange an encapsulation on top of the electrodes and the organic layers. The encapsulation may take the form, for example, of a glass lid or the form of a thin-film encapsulation.

The carrier material used in the optoelectronic device may, for example, be glass, quartz, plastic, metal, a silicon wafer or any other suitable solid or flexible, optionally transparent material. The carrier material may include, for example, one or more materials in the form of a layer, a film, a sheet or a laminate.

Anodes used in the optoelectronic device may, for example, be transparent conductive metal oxides, for example ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides.

HIL materials used may, for example, be PEDOT:PSS (poly-3,4-ethylenedioxythiophene:polystyrenesulphonic acid), PEDOT (poly-3,4-ethylenedioxythiophene), m-MTDATA (4,4',4''-tris[phenyl(m-tolyl)amino]triphenylamine), spiro-TAD (2,2',7,7'-tetrakis(N,N-diphenylamino)-9,9-spirobifluorene), DNTPD (4,4'-bis[N-[4-{N,N-bis(3-methylphenyl)amino}phenyl]-N-phenylamino]biphenyl), NPB (N,N'-bis-(1-naphthalenyl)-N, N'-bisphenyl-(1,1'-biphenyl)-4,4'-diamine), NPNPB (N,N'-diphenyl-N,N'-di-[4-(N, N-diphenylamino)phenyl]benzene), MeO-TPD (N, N, N',N'-tetrakis(4-methoxyphenyl)benzene), HAT-CN (1,4,5,8,9,11-hexaazatriphenylenehexacarbonitrile) or spiro-NPD (N,N'-diphenyl-N,N'-bis(1-naphthyl)-9,9'-spirobifluorene-2,7- diamine). By way of example, the layer thickness is 10-80 nm. In addition, it is possible to use small molecules (e.g. copper phthalocyanine (CuPc, e.g. thickness 10 nm)) or metal oxides, for instance $MoO_3$, $V_2O_5$.

HTL materials used may be tertiary amines, carbazole derivatives, polystyrenesulphonic acid-doped polyethylenedioxythiophene, camphorsulphonic acid-doped polyaniline, poly-TPD (poly(4-butylphenyldiphenylamine), [alpha]-NPD (poly(4-butylphenyldiphenylamine)), TAPC (4,4'-cyclohexylidenebis[N,N-bis(4-methylphenyl)benzeneamine]), TCTA (tris(4-carbazoyl-9-ylphenyl)amine), 2-TNATA (4,4', 4"-tris[2-naphthyl(phenyl)amino]triphenylamine), spiro-TAD, DNTPD, NPB, NPNPB, MeO-TPD, HAT-CN or TrisPcz (9,9'-diphenyl-6-(9-phenyl-9H-carbazol-3-yl)-9H, 9'H-3,3'-bicarbazole). By way of example, the layer thickness is 10 nm to 100 nm.

The HTL may have a p-doped layer having an inorganic or organic dopant in an organic hole-conducting matrix. Inorganic dopants used may, for example, be transition metal oxides, for instance vanadium oxide, molybdenum oxide or tungsten oxide. Organic dopants used may, for example, be tetrafluorotetracyanoquinodimethane (F4-TCNQ), copper pentafluorobenzoate (Cu(I)pFBz) or transition metal complexes. By way of example, the layer thickness is 10 nm to 100 nm.

Electron blocker layer materials used may, for example, be mCP (1,3-bis(carbazol-9-yl)benzene), TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene). By way of example, the layer thickness is 10 nm to 50 nm.

The emitter layer EML or emission layer consists of or comprises emitter material or a mixture including at least two emitter materials and optionally one or more host materials. Suitable host materials are, for example, mCP, TCTA, 2-TNATA, mCBP, CBP (4,4'-bis(N-carbazolyl) biphenyl), Sif87 (dibenzo[b, d]thiophen-2-yltriphenylsilane), Sif88 (dibenzo[b,d]thiophen-2-yl)diphenylsilane), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl) phenyl]-9H-carbazole, 9-[3,5-bis(2-dibenzothio-phenyl) phenyl]-9H-carbazole, T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluoren-2-yl)-1,3,5-triazine) and/or DPEPO (bis[2-((oxo)diphenylphosphino)phenyl] ether). In one embodiment, the EML contains 50%-80% by weight, preferably 60%-75% by weight, of a host material selected from the group consisting of CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl) phenyl]-9H-carbazole and 9-[3,5-bis(2-dibenzothiophenyl) phenyl]-9H-carbazole; 5%-45% by weight, preferably 10%-30% by weight, of T2T and 5%-40% by weight, preferably 10%-30% by weight, of an organic molecule according to the invention as emitter. For emitter material which emits in the green or in the red or a mixture comprising at least two emitter materials, the standard matrix materials are suitable, such as CBP. For emitter material which emits in the blue or a mixture comprising at least two emitter materials, it is possible to use UHG matrix materials (ultra-high-energy gap materials) (see, for example, M. E. Thompson et al., Chem. Mater. 2004, 16, 4743), or other so-called wide-gap matrix materials. By way of example, the layer thickness is 10 nm to 250 nm.

The hole blocker layer HBL may include, for example, BCP (2,9-dimethyl-4,7-diphenyl-1,10-phenanthroline=bathocuproin), bis(2-methyl-8-hydroxyquinolinato)-(4-phenylphenolato)-aluminium(III) (BAlq), NBphen (2,9-bis(naphthalen-2-yl)-4,7-diphenyl-1,10-phenanthroline), Alq3 (aluminium tris(8-hydroxyquinoline)), T2T, TSPO1 (diphenyl-4-triphenylsilylphenylphosphine oxide) or TCB/TCP (1,3,5-tris(N-carbazolyl)benzene/ 1,3,5-tris(carbazol)-9-yl)benzene). By way of example, the layer thickness is 10 nm to 50 nm.

The electron transport layer ETL may include, for example, materials based on $AlQ_3$, TSPO1, NBPhen, 1,3,5-tri(1-phenyl-1H-benzo[d]imidazol-2-yl)phenyl (TPBi), BPyTP2 (2,7-di(2,2'-bipyridin-5-yl)triphenyl), Sif87, Sif88, BmPyPhB (1,3-bis[3,5-di(pyridin-3-yl)phenyl]benzene) or BTB (4,4'-bis[2-(4,6-diphenyl-1,3,5-triazinyl)]-1,1'-biphenyl). By way of example, the layer thickness is 10 nm to 200 nm.

Materials used in a thin electron injection layer EIL may, for example, be CsF, LiF, 8-hydroxyquinolinolatolithium (Liq), $Li_2O$, $BaF_2$, MgO or NaF.

Materials used in the cathode layer may be metals or alloys, for example Al, Al>AlF, Ag, Pt, Au, Mg, Ag:Mg. Typical layer thicknesses are 100 nm to 200 nm. In particular, one or more metals that are stable under air and/or self-passivating, for example through formation of a thin protective oxide layer, are used.

Suitable materials for encapsulation are, for example, aluminium oxide, vanadium oxide, zinc oxide, zirconium oxide, titanium oxide, hafnium oxide, lanthanum oxide, tantalum oxide.

In one embodiment of the organic optoelectronic device according to the invention, the organic molecule according to the invention is used as emission material in a light-emitting layer EML, where it is used either in the form of a pure layer or in combination with one or more host materials.

One embodiment of the invention relates to organic optoelectronic devices having an external quantum efficiency (EQE) at 1000 $cd/m^2$ of greater than 5%, especially of greater than 8%, especially of greater than 10%, or of greater than 13%, or of greater than 16% and especially of greater than 20%, and/or an emission maximum at a wavelength between 420 nm and 500 nm, especially between 430 nm and 490 nm, or between 440 nm and 480 nm and especially between 450 nm and 470 nm, and/or an LT80 value at 500 $cd/m^2$ of greater than 30 h, especially of greater than 70 h, or of greater than 100 h, or of greater than 150 h and especially of greater than 200 h.

The proportion by mass of the organic molecule according to the invention in the emitter layer EML, in a further embodiment in a light-emitting layer in optical light-emitting devices, especially in OLEDs, is between 1% and 80%. In one embodiment of the organic optoelectronic device according to the invention, the light-emitting layer is applied to a substrate, preferably with application of an anode and a cathode to the substrate and application of the light-emitting layer between the anode and cathode.

The light-emitting layer, in one embodiment, may have exclusively an organic molecule according to the invention in 100% concentration, with the anode and the cathode applied to the substrate, and the light-emitting layer applied between the anode and cathode.

In one embodiment of the organic optoelectronic device according to the invention, a hole- and electron-injecting layer has been applied between the anode and cathode, and a hole- and electron-transporting layer between the hole- and electron-injecting layer, and the light-emitting layer between the hole- and electron-transporting layer.

The organic optoelectronic device, in a further embodiment of the invention, has: a substrate, an anode, a cathode and at least one hole- and one electron-injecting layer, and at least one hole- and one electron-transporting layer, and at least one light-emitting layer including an organic molecule according to the invention and one or more host materials, the triplet ($T_1$) and singlet ($S_1$) energy levels of which are at higher energy than the triplet ($T_1$) and singlet ($S_1$) energy levels of the organic molecule, with the anode and cathode applied to the substrate, and the hole- and electron-injecting layer applied between the anode and cathode, and the hole- and electron-transporting layer applied between the hole- and electron-injecting layer, and the light-emitting layer applied between the hole- and electron-transporting layer.

In a further aspect, the invention relates to a process for producing an optoelectronic component. This is done using an organic molecule according to the invention.

In one embodiment, the production process encompasses the processing of the organic molecule according to the invention by means of a vacuum evaporation method or from a solution.

The invention also includes a process for producing an optoelectronic device according to the invention, in which at least one layer of the optoelectronic device
is coated by a sublimation method,
is coated by an OVPD (organic vapour phase deposition) method,
is coated by a carrier gas sublimation, and/or
is produced from solution or by a printing method.

In the production of the optoelectronic device according to the invention, known methods are used. In general, the layers are applied individually to a suitable substrate in successive deposition process steps. In the gas phase deposition, it is possible to employ the commonly used methods, such as thermal evaporation, chemical gas phase deposition (CVD), physical gas phase deposition (PVD). For active-matrix OLED (AMOLED) displays, deposition is effected on an AMOLED backplane as substrate.

Alternatively, it is possible to apply layers from solutions or dispersions in suitable solvents. Illustrative suitable coating methods are spin-coating, dip-coating and jet printing methods. The individual layers can be produced in accordance with the invention either via the same coating method or via different coating methods in each case.

BRIEF DESCRIPTION OF THE DRAWINGS

The figures show.

DETAILED DESCRIPTION AND EXAMPLES

General Synthesis Scheme I

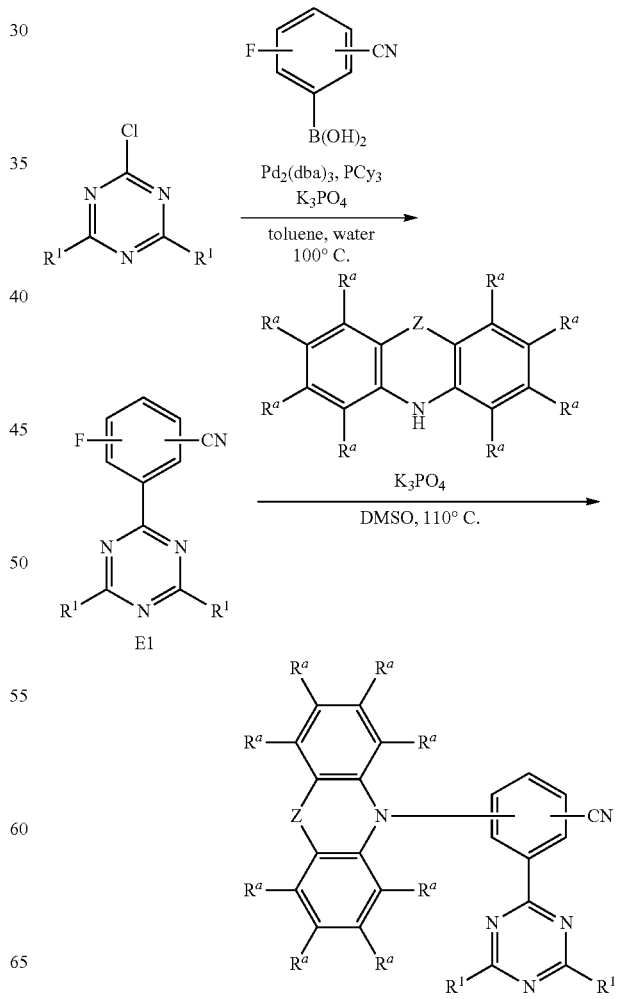

General Synthesis Method GM1

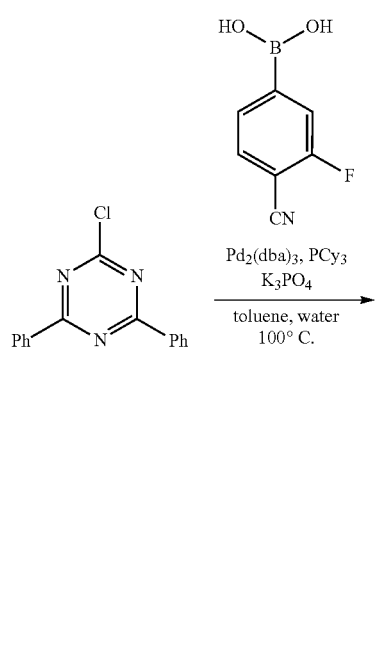

Figure 1:
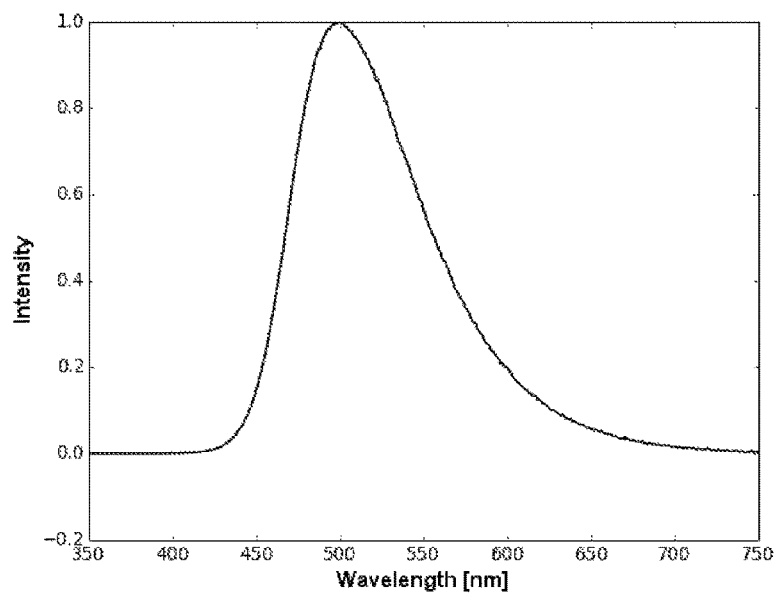
FIG. 1 Emission spectrum of Example 1 (10% in PMMA).

2-Chloro-4,6-diphenyl-1,3,5-triazine (1.00 equivalent), 3-fluoro-4-cyanophenylboronic acid (1.20 equivalents), Pd$_2$(dba)$_3$ (dba=dibenzylideneacetone) (0.03 equivalent), tricyclohexylphosphine (PCy$_3$) (0.07 equivalent) and tribasic potassium phosphate (1.70 equivalent) are stirred under nitrogen in a dioxane/toluene/water mixture (ratio 10:3:2) at 100° C. for 20 h. Subsequently, the reaction mixture is added to 200 ml of saturated sodium chloride solution and extracted with ethyl acetate (2×200 ml). The combined organic phases are washed with saturated sodium chloride solution and dried over MgSO$_4$, and the solvent is removed. The resulting crude product is purified by flash chromatography and the product is obtained in solid form.

It is also possible in accordance with the invention to use a corresponding boronic ester rather than a boronic acid.

General Synthesis Method GM2

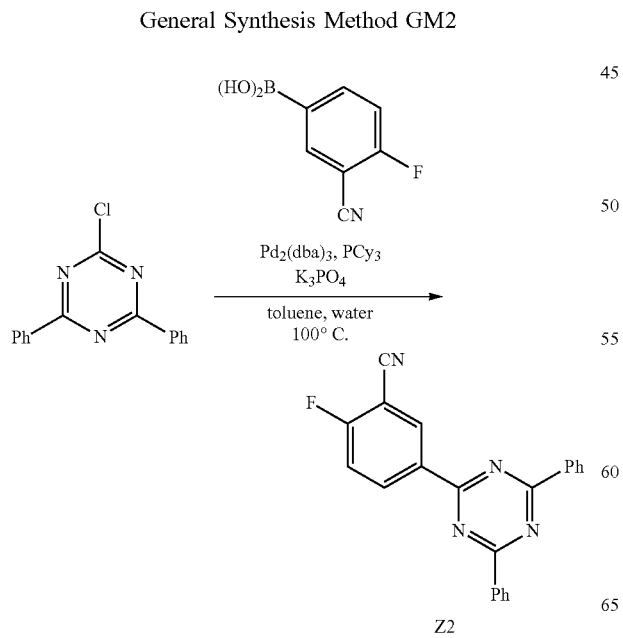

The synthesis of Z2 is performed analogously to GM1, by reaction of 2-chloro-4,6-diphenyl-1,3,5-triazine with 4-fluoro-3-cyanophenylboronic acid.

General Synthesis Method GM3

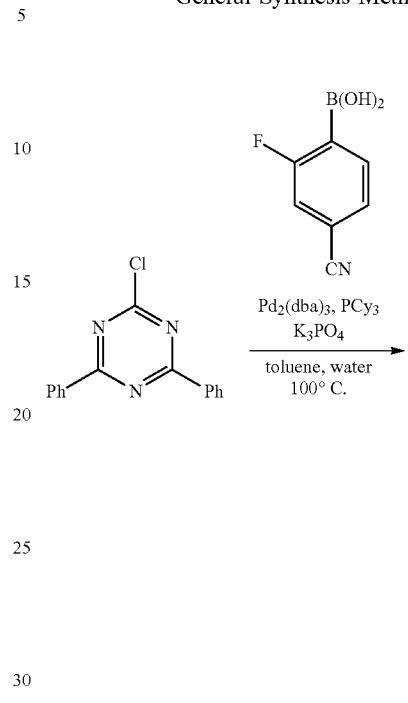

The synthesis of Z3 is performed analogously to GM1, by reaction of 2-chloro-4,6-diphenyl-1,3,5-triazine with 2-fluoro-4-cyanophenylboronic acid.

General Synthesis Method GM4

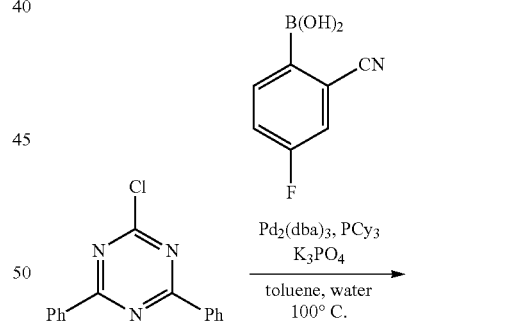

The synthesis of Z4 is performed analogously to GM1, by reaction of 2-chloro-4,6-diphenyl-1,3,5-triazine with 4-fluoro-2-cyanophenylboronic acid.

General Synthesis Method GM5

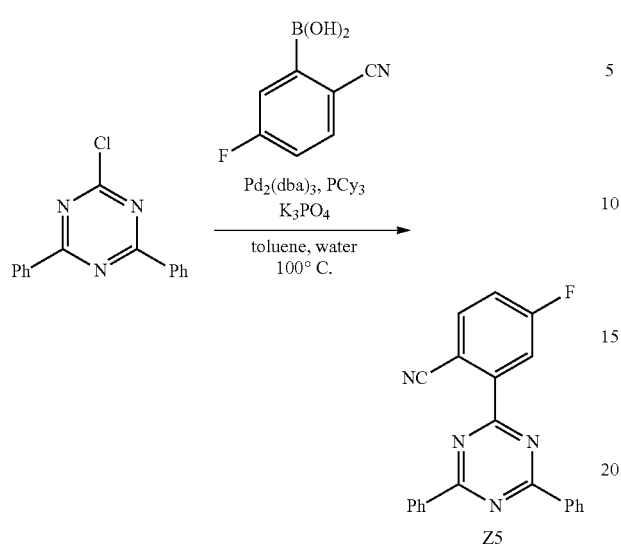

The synthesis of Z5 is performed analogously to GM1, by reaction of 2-chloro-4,6-diphenyl-1,3,5-triazine with 3-fluoro-6-cyanophenylboronic acid.

General Synthesis Method GM6

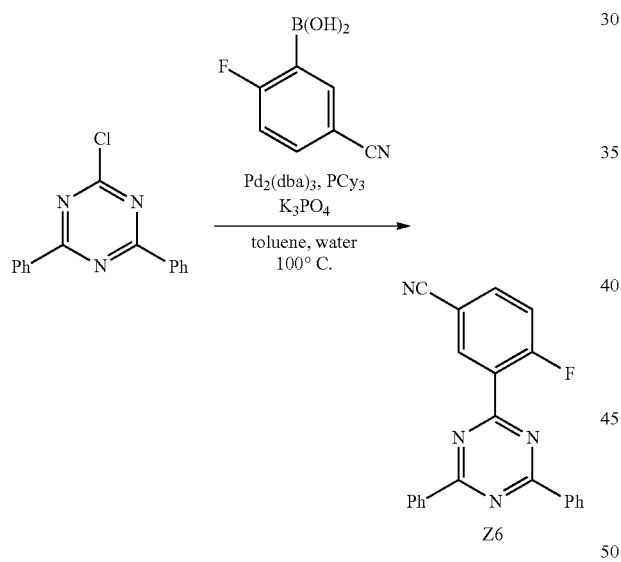

The synthesis of Z6 is performed analogously to GM1, by reaction of 2-chloro-4,6-diphenyl-1,3,5-triazine with 2-fluoro-5-cyanophenylboronic acid.

General Synthesis Method GM7

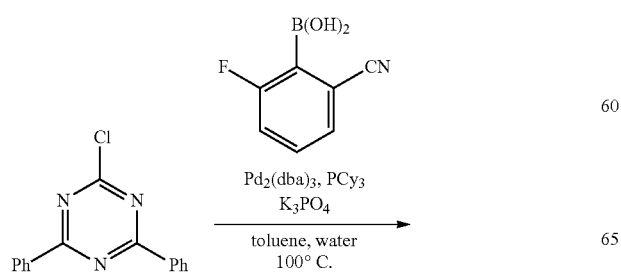

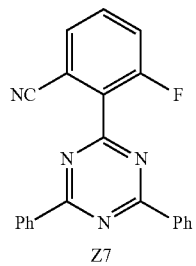

The synthesis of Z7 is performed analogously to GM1, by reaction of 2-chloro-4,6-diphenyl-1,3,5-triazine with 2-fluoro-6-cyanophenylboronic acid.

General Synthesis Method GM8

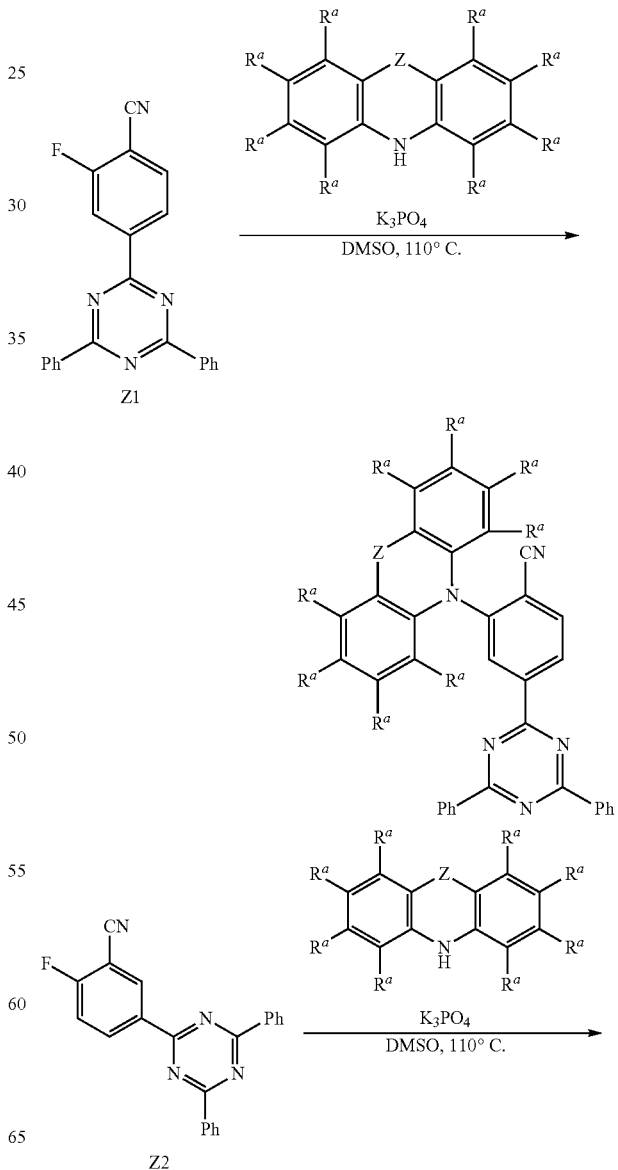

-continued
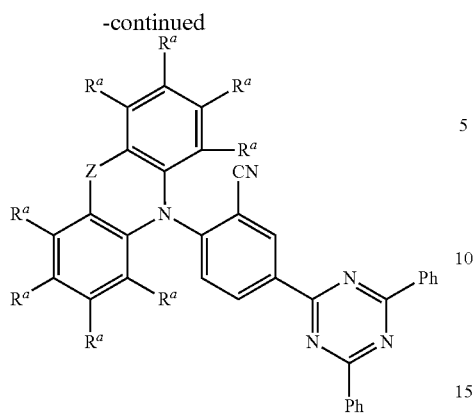
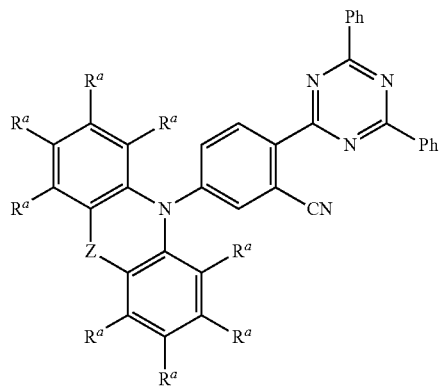
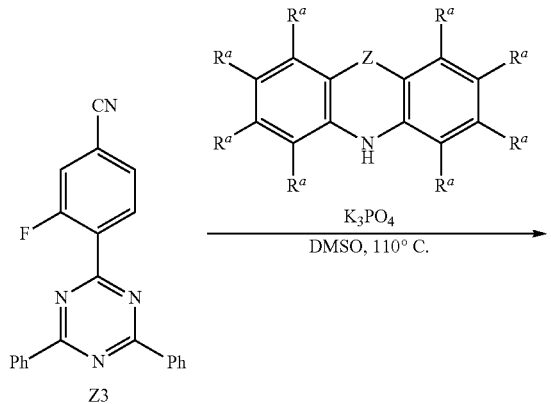
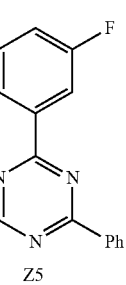
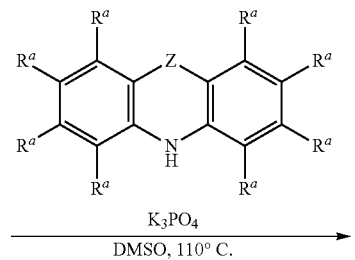
Z3
Z5
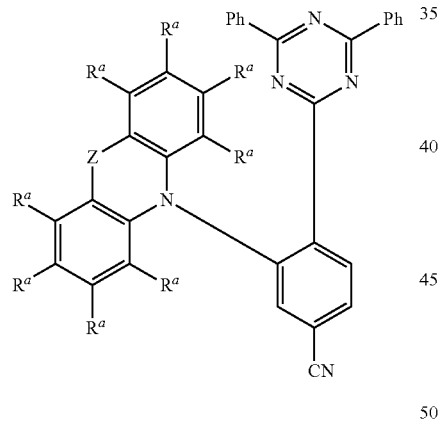
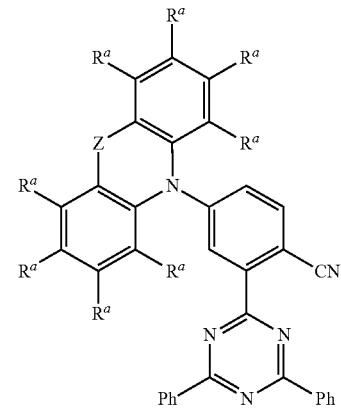
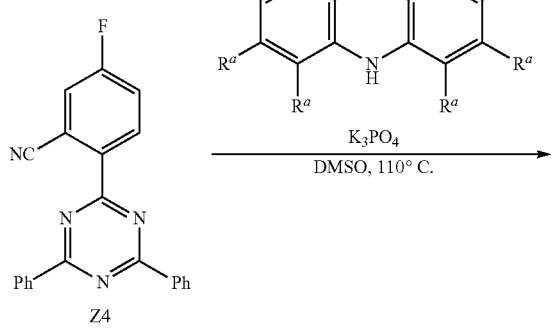
Z4
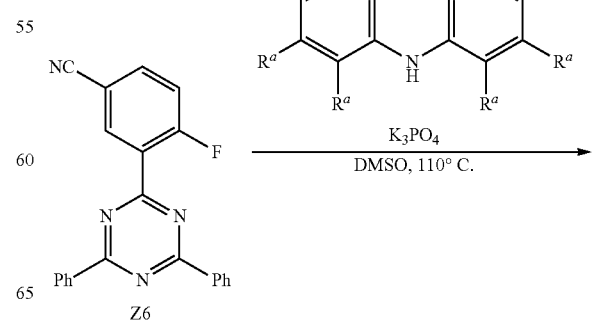
Z6

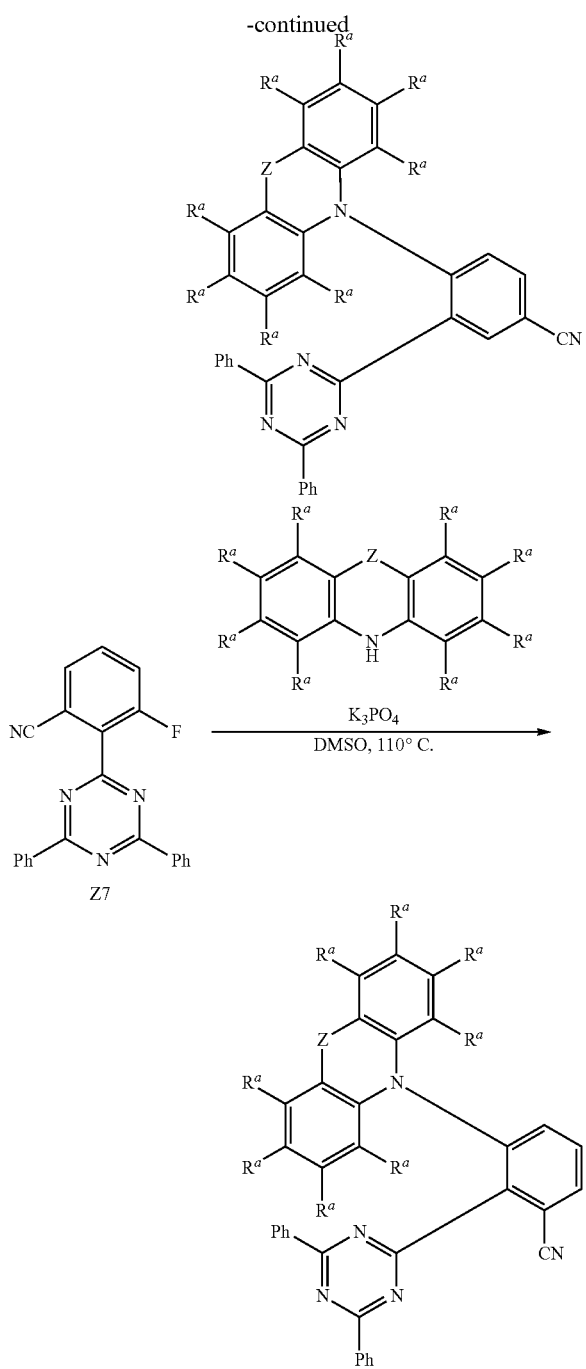

Z1, Z2, Z3, Z4, Z5, Z6 or Z7 (1.00 equivalent of each), the appropriate donor molecule D-H (1.00 equivalent) and tribasic potassium phosphate (2.00 equivalents) are suspended in DMSO under nitrogen and stirred at 110° C. (16 h). Subsequently, the reaction mixture is added to saturated sodium chloride solution and extracted three times with dichloromethane. The combined organic phases are washed twice with saturated sodium chloride solution and dried over magnesium sulphate, and the solvent is then removed. The crude product was finally purified by recrystallization from toluene or by flash chromatography. The product is obtained in solid form.

In order to obtain the corresponding $R^1$-substituted compounds, the corresponding 4- and 6-$R^1$-substituted 2-chloro-1,3,5-triazine, for example 2-chloro-4,6-methyl-1,3,5-triazine, is used instead of 2-chloro-4,6-diphenyl-1,3,5-triazine.

Specifically, D-H corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), a 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole). It is especially possible to use a halocarbazole, especially 3-bromocarbazole or 3,6-dibromocarbazole, as D-H, which is converted in a subsequent reaction, for example, to a corresponding boronic acid, for example (carbazol-3-yl)boronic acid, or to a corresponding boronic ester, for example (carbazol-3-yl)boronic ester, by way of example by reaction with bis(pinacol)boronic ester (CAS No. 73183-34-3). In a subsequent reaction, it is possible to introduce one or more $R^a$ radicals which are used in the form of the halogenated reactant $R^a$—Hal, preferably $R^a$—Cl and $R^a$—Br, in place of the boronic acid group or the boronic ester group via a coupling reaction. Alternatively, one or more $R^a$ radicals can be introduced by reaction of the previously introduced halocarbazole with boronic acids of the $R^a$ radical ($R^a$—$B(OH)_2$) or corresponding boronic esters.

Photophysical Measurements

Pretreatment of Optical Glassware

All glassware (cuvettes and substrates made from quartz glass, diameter: 1 cm) was cleaned after each use: Three rinses each time with dichloromethane, acetone, ethanol, demineralized water, placing in 5% Hellmanex solution for 24 h, thorough rinsing-out with demineralized water. For drying, the optical glassware was blown dry with nitrogen.

Sample Preparation, Film: Spin-Coating

Instrument: Spin150, SPS euro.

Sample concentration corresponded to 10 mg/ml, made up in toluene or chlorobenzene. Programme: 1) 3 s at 400 rpm; 2) 20 s at 1000 rpm at 1000 rpm/s. 3) 10 s at 4000 rpm at 1000 rpm/s. After coating, the films were dried at 70° C. under air on an LHG precision hotplate for 1 min.

Photoluminescence Spectroscopy and TCSPC

Steady-state emission spectroscopy was conducted with a Horiba Scientific fluorescence spectrometer, model: Fluoro-Max-4, equipped with a 150 W xenon arc lamp, excitation and emission monochromators and a Hamamatsu R928 photomultiplier tube, and also a "time-correlated single-photon counting" (TCSPC) option. Emission and excitation spectra were corrected by means of standard correction curves.

The emission decay times were likewise measured with this system using the TCSPC method with the FM-2013 accessories and a TCSPC hub from Horiba Yvon Jobin. Excitation sources: NanoLED 370 (wavelength: 371 nm, pulse duration: 1.1 ns)

NanoLED 290 (wavelength: 294 nm, pulse duration: <1 ns)

SpectraLED 310 (wavelength: 314 nm)

SpectraLED 355 (wavelength: 355 nm).

The evaluation (exponential fitting) was performed with the DataStation software package and the DAS 6 evaluation software. The fit was reported by the chi-squared method $$c^2 = \sum_{k=1}^{i} \frac{(e_i - o_i)^2}{e_i}$$

with $e_i$: parameter predicted by the fit and $o_i$: parameter measured.

Determination of Quantum Efficiency

The photoluminescence quantum yield (PLQY) was measured by means of an Absolute PL Quantum Yield Measurement C9920-03G system from Hamamatsu Photonics. This consists of a 150 W xenon gas discharge lamp, automatically adjustable Czerny-Turner monochromators (250-950 nm) and an Ulbricht sphere with highly reflective Spectralon coating (a Teflon derivative), connected via a glass fibre cable to a PMA-12 multichannel detector with a BT (back-thinned) CCD chip having 1024×122 pixels (size 24×24 μm). The quantum efficiency and the CIE coordinates were evaluated with the aid of the U6039-05 software, version 3.6.0.

The emission maximum is reported in nm, the quantum yield ϕ in %, and the CIE colour coordinates as x,y values.

The photoluminescence quantum yield was determined according to the following protocol:
1) Performance of quality assurance: The reference material used is anthracene in ethanol with known concentration.
2) Determining the excitation wavelength: First of all, the absorption maximum of the organic molecule was determined and it was excited therewith.
3) Performance of sample analysis:

The absolute quantum yield of degassed solutions and films was determined under a nitrogen atmosphere.

The calculation was effected within the system according to the following equation:

$$\Phi_{PL} = \frac{n_{photon}, \text{emitted}}{n_{photon}, \text{absorbed}} = \frac{\int \frac{\lambda}{hc}\left[Int_{emitted}^{sample}(\lambda) - Int_{absorbed}^{sample}(\lambda)\right]d\lambda}{\int \frac{\lambda}{hc}\left[Int_{emitted}^{reference}(\lambda) - Int_{absorbed}^{reference}(\lambda)\right]d\lambda}$$

with the photon count $n_{photon}$ and the intensity Int.

Production and characterization of organic electroluminescent devices from the gas phase With the organic molecules according to the invention, it is possible to create OLED devices by means of vacuum sublimation methodology. If one layer comprises two or more components, the ratio thereof is reported in percent by mass.

These as yet unoptimized OLEDs can be characterized in a standard manner; for this purpose, the electroluminescent spectra, the external quantum efficiency (measured in %) as a function of brightness, calculated from the light detected by the photodiode, and the current are recorded. It is possible to determine the lifetime of the OLEDs from the variation in the electroluminescence spectra with time. The LT50 value corresponds here to the period of time over which the luminance has fallen to 50% of the starting value. Analogously, the LT70 value corresponds to the period of time over which the luminance has fallen to 70% of the starting value.

The values are found from the average of the different pixels of an OLED.

HPLC-MS:

HPLC-MS spectroscopy was measured with an Agilent HPLC system (1100 series) connected to an MS detector (Thermo LTQ XL). For the HPLC, an Eclipse Plus C18 column from Agilent with a particle size of 3.5 μm, a length of 150 mm and an internal diameter of 4.6 mm was used. No pre-column was employed and operation was effected at room temperature with the solvents acetonitrile, water and tetrahydrofuran in these concentrations:

Solvent A: $H_2O$ (90%) MeCN (10%)
Solvent B: $H_2O$ (10%) MeCN (90%)
Solvent C: THF (100%)

An injection volume of 15 μl and a concentration of 10 μg/ml with this gradient was employed:

| Flow rate [ml/min] | Time [min] | A [%] | B [%] | C [%] | Pressure [bar] |
|---|---|---|---|---|---|
| 0.3 | 0 | 80 | 20 | — | 115 |
| 0.3 | 5 | 80 | 20 | — | 115 |
| 0.3 | 14 | 0 | 90 | 10 | 65 |
| 0.3 | 25 | 0 | 90 | 10 | 65 |
| 0.3 | 26 | 80 | 20 | — | 115 |
| 0.3 | 33 | 80 | 20 | — | 115 |

The sample was ionized by APCI (atmospheric pressure chemical ionization).

Example 1

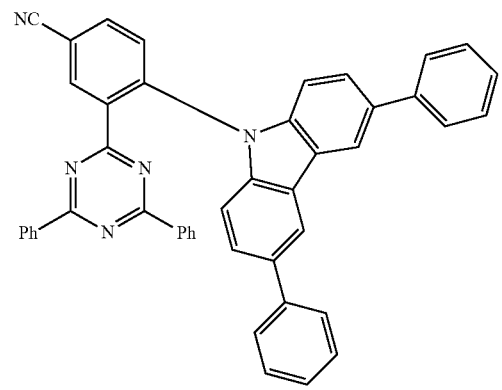 [SMILES: N#Cc1ccc(-n2c3ccc(-c4ccccc4)cc3c3cc(-c4ccccc4)ccc32)c(-c2nc(-c3ccccc3)nc(-c3ccccc3)n2)c1]

Example 1 was prepared according to GM6 (43% yield) and GM8 (58% yield).

$^1$H NMR (500 MHz, $CDCl_3$): δ=8.91 (d, 1H), 8.29 (d, 2H), 8.15 (dd, 1H), 8.06 (d, 4H), 7.95 (d, 1H), 7.68 (d, 4H), 7.61 (dd, 2H), 7.49 (t, 6H), 7.26-7.38 (m, 8H) ppm.

FIG. 1 shows the emission spectrum of Example 1 (10% in PMMA). The emission maximum is at 499 nm. The photoluminescence quantum yield (PLQY) is 78% and the half-height width is 0.43 eV. The emission lifetime is 7 μs.

Example 2

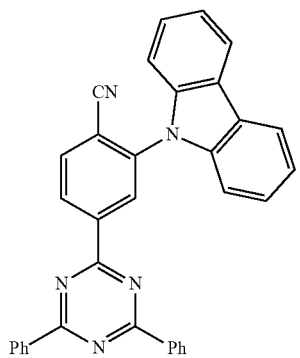 [SMILES: N#Cc1ccc(-c2nc(-c3ccccc3)nc(-c3ccccc3)n2)cc1-n1c2ccccc2c2ccccc21]

Example 2 was prepared according to GM1 (37% yield) and GM8 (74% yield).

$^1$H NMR (500 MHz, CDCl$_3$): δ=9.03-9.06 (m, 2H), 8.75 (d, 4H), 8.23 (d, 2H), 8.18 (d, 1H), 7.64-7.67 (m, 2H), 7.59 (t, 4H), 7.50 (t, 2H), 7.41 (t, 2H), 7.31 (d, 2H) ppm.

Figure 2:
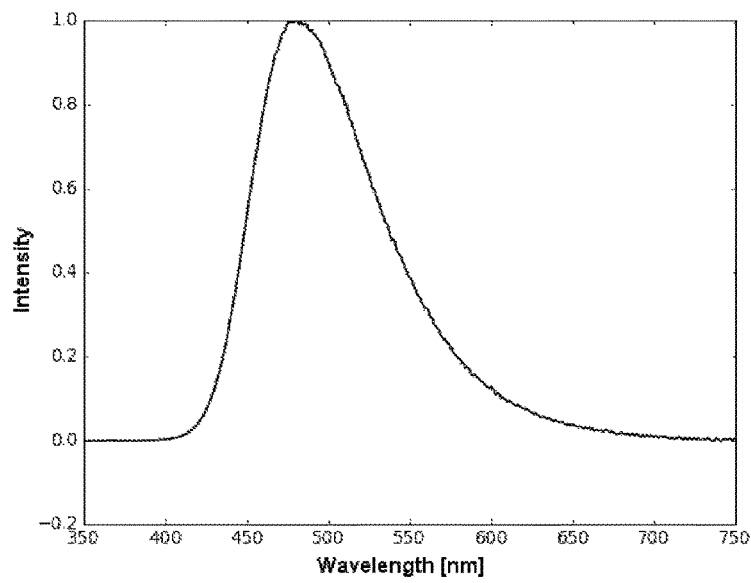
FIG. 2 Emission spectrum of Example 2 (10% in PMMA).

FIG. 2 shows the emission spectrum of Example 2 (10% in PMMA). The emission maximum is at 481 nm. The photoluminescence quantum yield (PLQY) is 74% and the half-height width is 0.46 eV.

Example 3

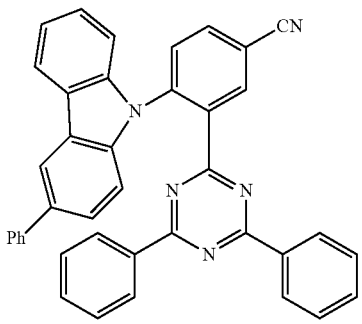 [SMILES: N#Cc1ccc(-n2c3ccccc3c3cc(-c4ccccc4)ccc32)c(-c2nc(-c3ccccc3)nc(-c3ccccc3)n2)c1]

Example 3 was prepared according to GM6 with a boronic ester (80% yield) and GM8 (37% yield).

$^1$H NMR (500 MHz, CDCl$_3$): d=8.89 (m, 1H), 8.25 (d, 1H), 8.14-8.19 (m, 2H), 8.04 (d, 4H), 7.91 (dd, 1H), 7.62-7.70 (m, 3H), 7.48-7.53 (m, 4H), 7.32-7.39 (m, 6H), 7.23-7.26 (m, 2H), 7.17 (d, 1H), 7.12 (t, 1H) ppm.

Figure 3:
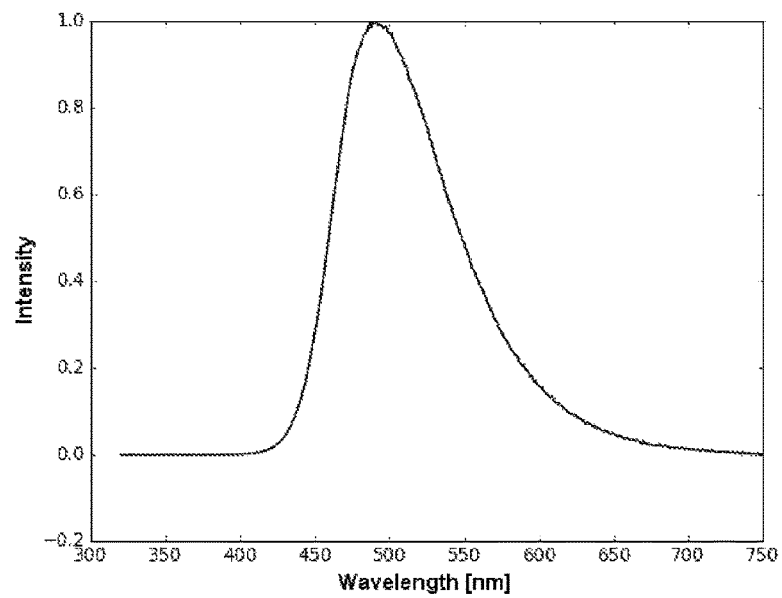
FIG. 3 Emission spectrum of Example 3 (10% in PMMA).

FIG. 3 shows the emission spectrum of Example 3 (10% in PMMA). The emission maximum is at 489 nm. The photoluminescence quantum yield (PLQY) is 72% and the half-height width is 0.44 eV. The emission lifetime is 8 μs.

Example 4

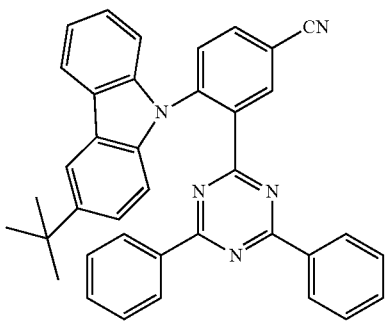 [SMILES: CC(C)(C)c1ccc2c(c1)c1ccccc1n2-c1ccc(C#N)cc1-c1nc(-c2ccccc2)nc(-c2ccccc2)n1]

Example 4 was prepared according to GM6 with a boronic ester (80% yield) and GM8 (35% yield).

$^1$H NMR (500 MHz, CDCl$_3$): d=8.88 (d, 1H), 8.10 (dd, 1H), 8.00-8.07 (m, 6H), 7.89 (d, 1H), 7.52 (t, 2H), 7.42 (dd, 1H), 7.36 (t, 4H), 7.25-7.28 (m, 1H), 7.16-7.21 (m, 2H), 7.12 (d, 1H), 1.43 (s, 9H) ppm.

Figure 4:
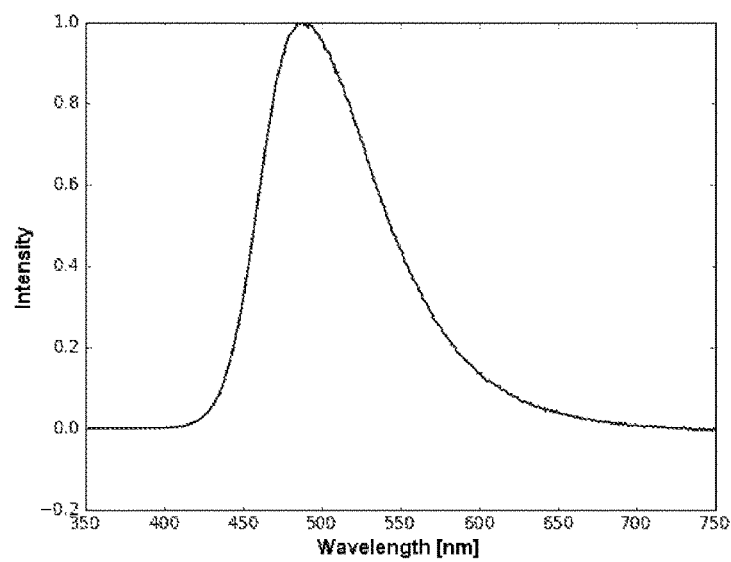
FIG. 4 Emission spectrum of Example 4 (10% in PMMA).

FIG. 4 shows the emission spectrum of Example 4 (10% in PMMA). The emission maximum is at 487 nm. The photoluminescence quantum yield (PLQY) is 73% and the half-height width is 0.43 eV. The emission lifetime is 11 μs.

Example 5

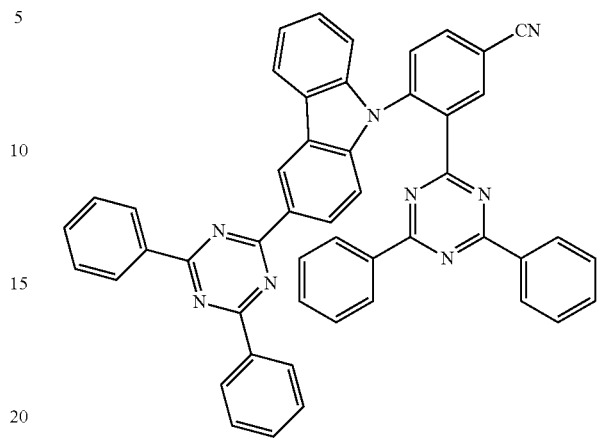

Example 5 was prepared according to GM6 with a boronic ester (80% yield), according to GM8 with 3-bromocarbazole (80% yield), subsequent further reaction with bis(pinacol)boronate and subsequent further reaction with 2-chloro-4,6-diphenyl-1,3,5-triazine.

$^1$H NMR (500 MHz, CDCl3): d=9.49 (s, 1H), 8.95 (d, 1H), 8.81-8.83 (m, 5H), 8.27 (d, 1H), 8.17 (dd, 1H), 8.04 (d, 4H), 7.96 (d, 1H), 7.60-7.67 (m, 6H), 7.30-7.50 (m, 9H), 7.25 (d, 1H) ppm.

Figure 5:
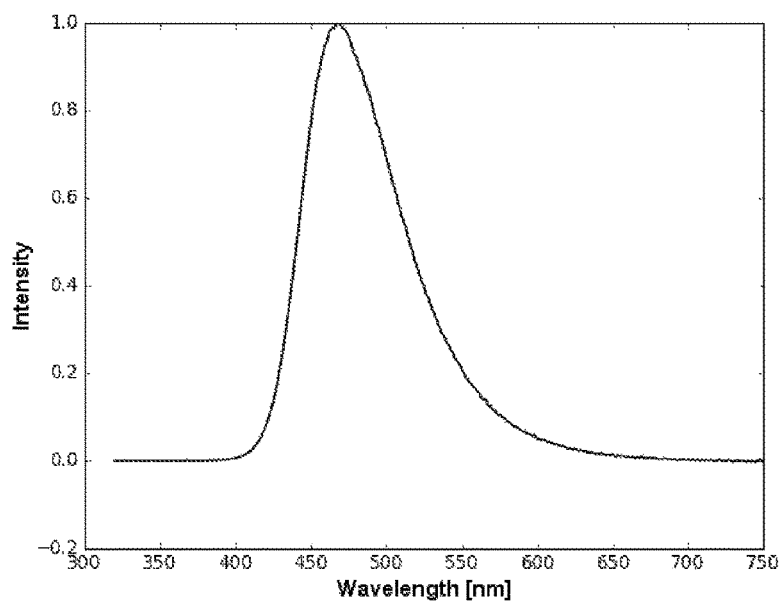
FIG. 5 Emission spectrum of Example 5 (10% in PMMA).

FIG. 5 shows the emission spectrum of Example 5 (10% in PMMA). The emission maximum is at 468 nm. The photoluminescence quantum yield (PLQY) is 80% and the half-height width is 0.41 eV. The emission lifetime is 24 μs.

Example 6

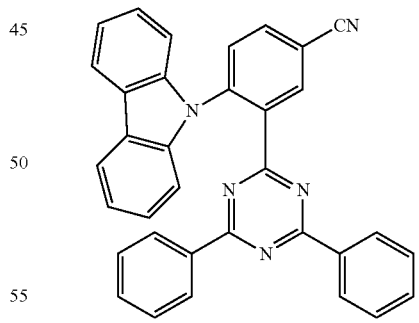

Example 6 was prepared according to GM6 with a boronic ester (80% yield) and GM8 (69% yield).

$^1$H NMR (500 MHz, CDCl3): d=8.89 (d, 1H), 8.11 (dd, 1H), 8.02 (d, 6H), 7.91 (d, 1H), 7.50-7.53 (m, 2H), 7.33-7.37 (m, 6H), 7.27 (t, 2H), 7.19 (d, 2H) ppm.

Figure 6:
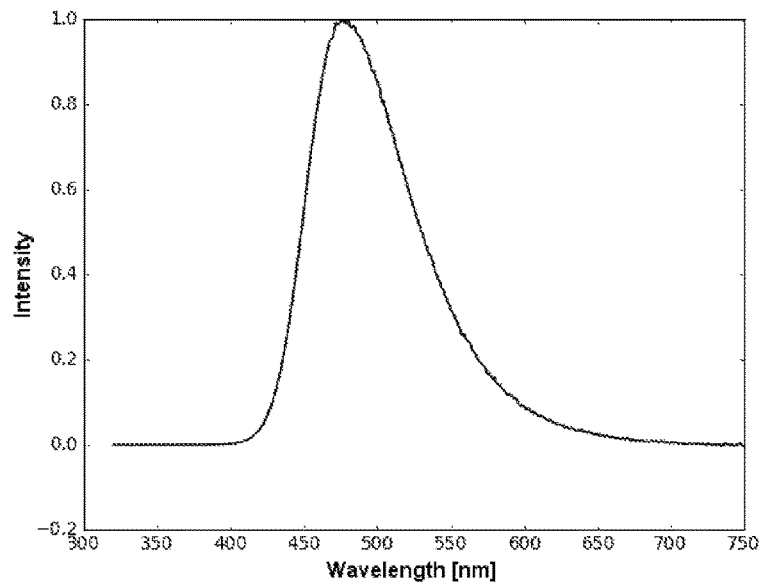
FIG. 6 Emission spectrum of Example 6 (10% in PMMA).

FIG. 6 shows the emission spectrum of Example 6 (10% in PMMA). The emission maximum is at 480 nm. The photoluminescence quantum yield (PLQY) is 83% and the half-height width is 0.43 eV. The emission lifetime is 15 μs.

Example 7

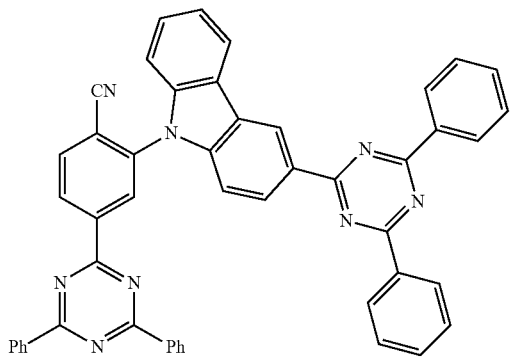 [SMILES: N#Cc1ccc(-c2nc(-c3ccccc3)nc(-c3ccccc3)n2)cc1-n1c2ccccc2c2cc(-c3nc(-c4ccccc4)nc(-c4ccccc4)n3)ccc21]

Example 7 was prepared according to GM1 (37% yield) and GM8 (98% yield), subsequent further reaction with bis(pinacol)boronate and subsequent further reaction with 2-chloro-4,6-diphenyl-1,3,5-triazine.

$^1$H NMR (500 MHz, CDCl$_3$): δ=9.68 (s, 1H), 9.11 (t, 2H), 8.98 (d, 1H), 8.86 (d, 4H), 8.76 (d, 4H), 8.46 (d, 1H), 8.22 (d, 1H), 7.57-7.67 (m, 13H), 7.51 (t, 1H), 7.45 (d, 1H), 7.35 (d, 1H) ppm.

Figure 7:
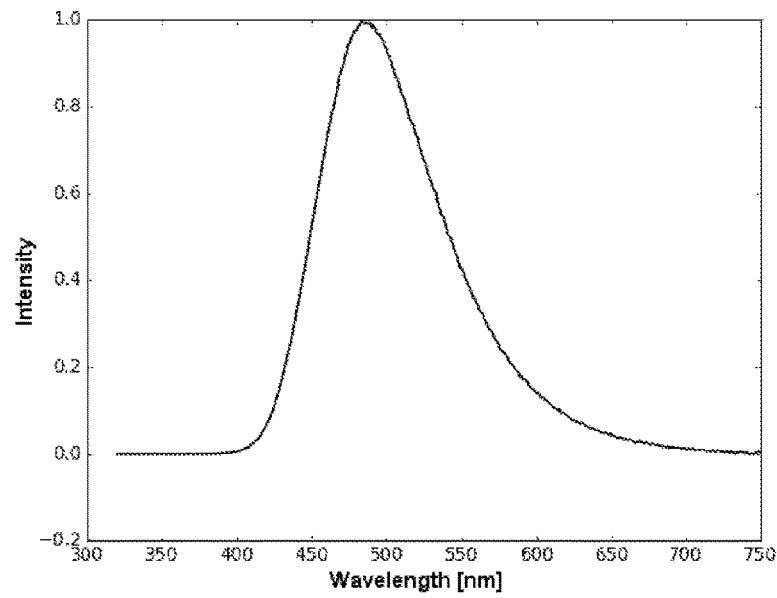
FIG. 7 Emission spectrum of Example 7 (10% in PMMA).

FIG. 7 shows the emission spectrum of Example 7 (10% in PMMA). The emission maximum is at 483 nm. The photoluminescence quantum yield (PLQY) is 68% and the half-height width is 0.48 eV.

Example 8

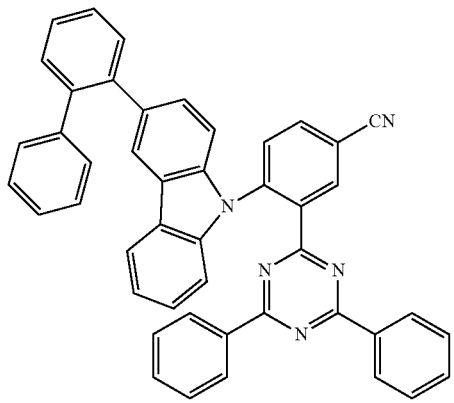 [SMILES: N#Cc1ccc(-n2c3ccccc3c3cc(-c4ccccc4-c4ccccc4)ccc32)c(-c2nc(-c3ccccc3)nc(-c3ccccc3)n2)c1]

Example 8 was prepared according to GM6 with a boronic ester (80% yield), according to GM8 with 3-bromocarbazole (65% yield) and in subsequent further reaction with 2-biphenylboronic acid (93% yield).

$^1$H NMR (500 MHz, CDCl3): d=8.87 (d, 1H), 8.08-8.10 (m, 5H), 7.99 (d, 1H), 7.90-7.92 (m, 2H), 7.52-7.56 (m, 2H), 7.47-7.49 (m, 1H), 7.37-7.42 (9H), 7.30 (s, 1H), 6.94-6.99 (m, 4H), 6.86-6.87 (m, 1H), 6.78 (t, 2H) ppm.

Figure 8:
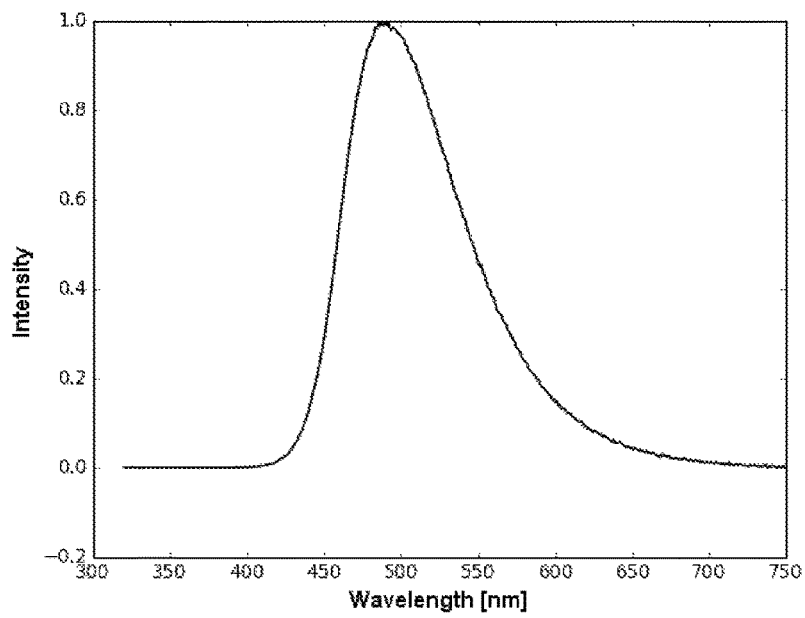
FIG. 8 Emission spectrum of Example 8 (10% in PMMA).

FIG. 8 shows the emission spectrum of Example 8 (10% in PMMA). The emission maximum is at 490 nm. The photoluminescence quantum yield (PLQY) is 64% and the half-height width is 0.44 eV. The emission lifetime is 9 μs.

Example 9

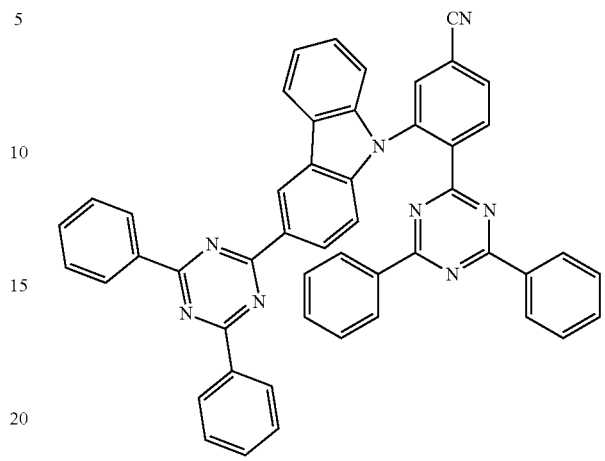

Example 9 was prepared according to GM3 (79% yield), according to GM8 with 3-bromocarbazole (87% yield), subsequent further reaction with bis(pinacol)boronate and subsequent further reaction with 2-chloro-4,6-diphenyl-1,3,5-triazine.

$^1$H NMR (500 MHz, CDCl$_3$): δ=9.48 (s, 1H), 8.81-8.83 (d, 5H), 8.72 (d, 1H), 8.27 (d, 1H), 8.11-8.14 (m, 2H), 8.03 (d, 4H), 7.60-7.65 (m, 6H), 7.30-7.50 (9H), 7.25-7.26 (m, 1H) ppm.

Figure 9:
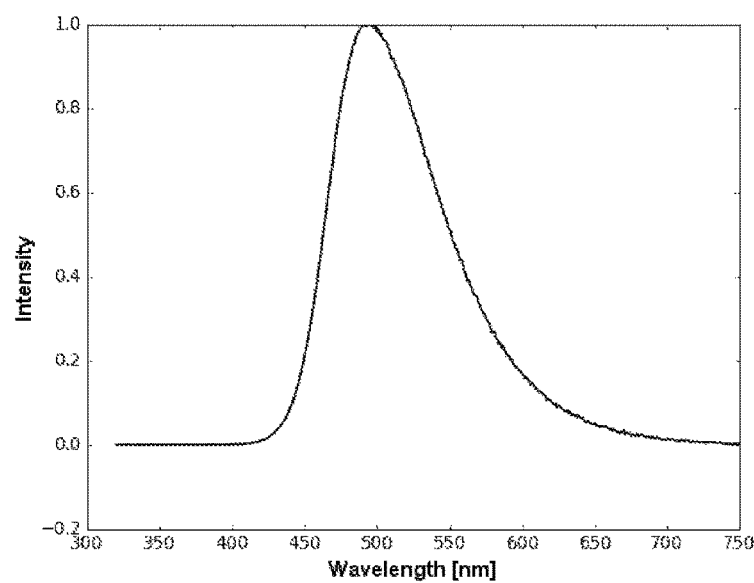
FIG. 9 Emission spectrum of Example 9 (10% in PMMA).

FIG. 9 shows the emission spectrum of Example 9 (10% in PMMA). The emission maximum is at 495 nm. The photoluminescence quantum yield (PLQY) is 71% and the half-height width is 0.43 eV. The emission lifetime is 20 μs.

Example 10

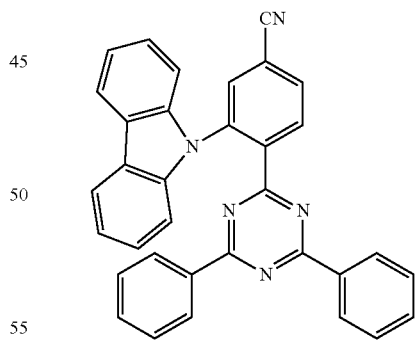

Example 10 was prepared according to GM3 (79% yield) and GM8 (56% yield).

$^1$H NMR (500 MHz, CDCl$_3$): δ=8.65 (d, 1H), 8.00-8.08 (m, 8H), 7.51 (t, 2H), 7.33-7.37 (m, 6H), 7.26 (t, 2H), 7.17 (d, 2H) ppm.

Figure 10:
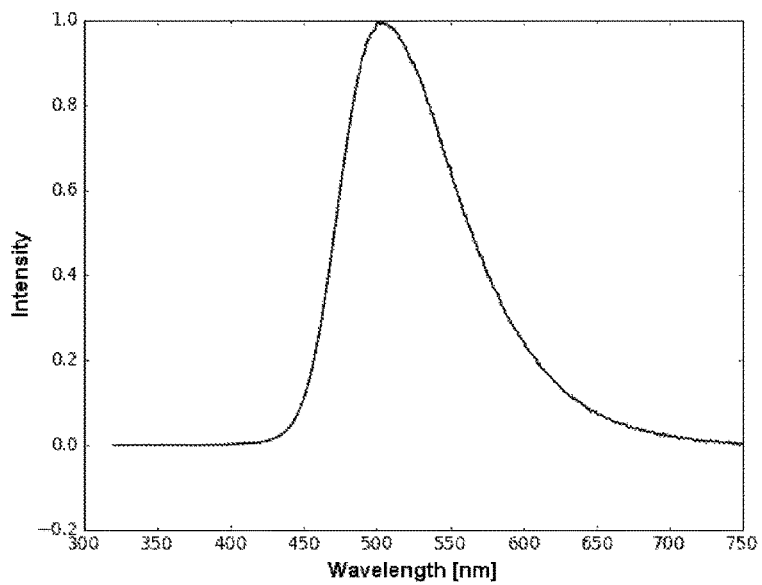
FIG. 10 Emission spectrum of Example 10 (10% in PMMA).

FIG. 10 shows the emission spectrum of Example 10 (10% in PMMA). The emission maximum is at 501 nm. The photoluminescence quantum yield (PLQY) is 68% and the half-height width is 0.44 eV. The emission lifetime is 18 μs.

Example 11

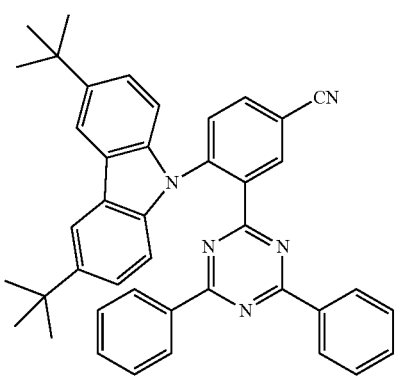 [SMILES: CC(C)(C)c1ccc2c(c1)c1cc(C(C)(C)C)ccc1n2-c1ccc(C#N)cc1-c1nc(-c2ccccc2)nc(-c2ccccc2)n1]

Example 11 was prepared according to GM6 with a boronic ester (80% yield) and GM8 (73% yield).

MS (HPLC-MS), m/z (retention time): 611, (10.55 min).

Figure 11:
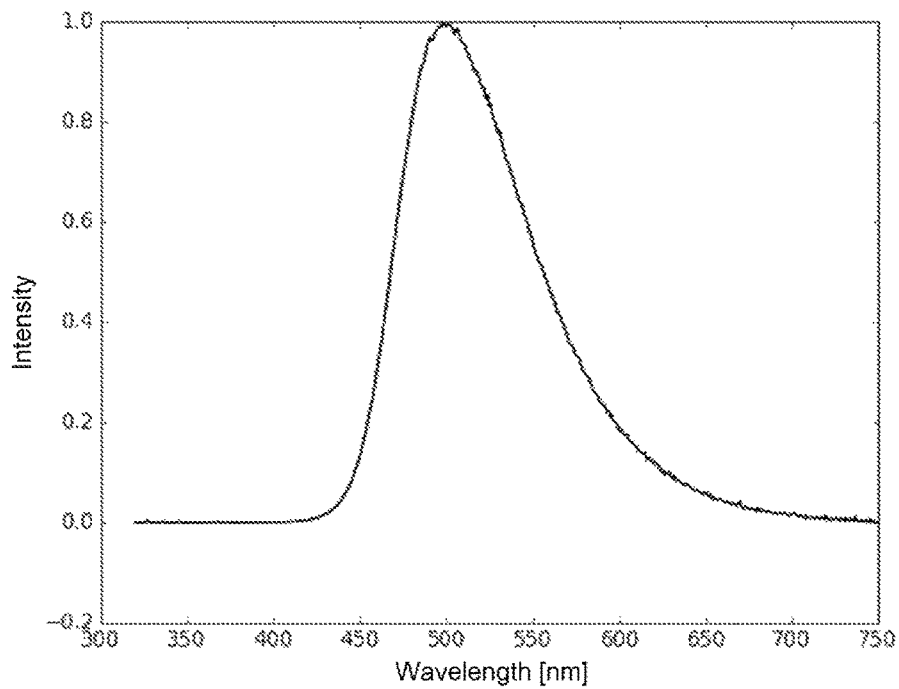
FIG. 11 Emission spectrum of Example 11 (10% in PMMA).

FIG. 11 shows the emission spectrum of Example 11 (10% in PMMA). The emission maximum is at 498 nm. The photoluminescence quantum yield (PLQY) is 71% and the half-height width is 0.42 eV. The emission lifetime is 9 µs.

Example 12

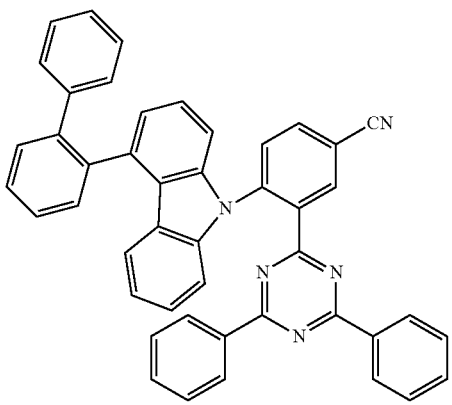 [SMILES: N#Cc1ccc(-n2c3ccccc3c3c(-c4ccccc4-c4ccccc4)cccc32)c(-c2nc(-c3ccccc3)nc(-c3ccccc3)n2)c1]

Example 12 was prepared according to GM6 with a boronic ester (80% yield) and GM8 (91% yield).

MS (HPLC-MS), m/z (retention time): 651 (9.15 min).

Figure 12:
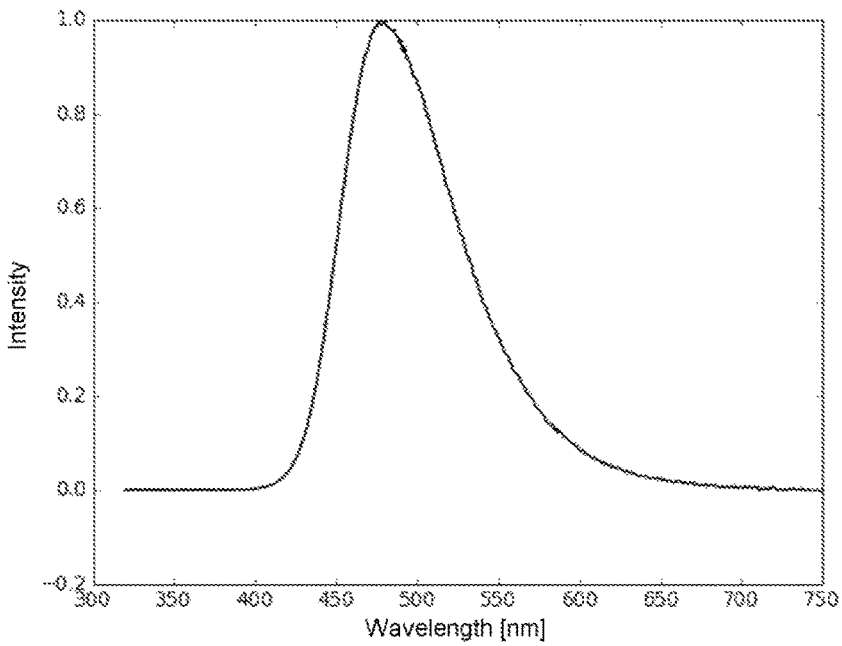
FIG. 12 Emission spectrum of Example 12 (10% in PMMA).

FIG. 12 shows the emission spectrum of Example 12 (10% in PMMA). The emission maximum is at 476 nm. The photoluminescence quantum yield (PLQY) is 80% and the half-height width is 0.42 eV. The emission lifetime is 26 µs.

Example 13

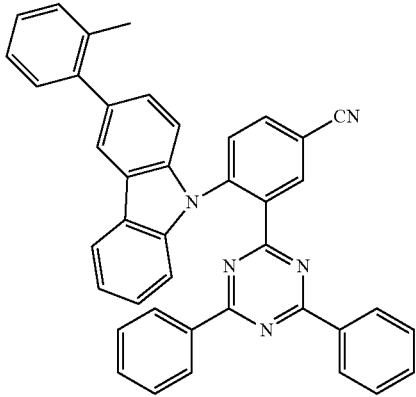 [SMILES: Cc1ccccc1-c1ccc2c(c1)c1ccccc1n2-c1ccc(C#N)cc1-c1nc(-c2ccccc2)nc(-c2ccccc2)n1]

Example 13 was prepared according to GM6 with a boronic ester (80% yield) and GM8 (44% yield).

MS (HPLC-MS), m/z (retention time): 589 (9.14 min).

Figure 13:
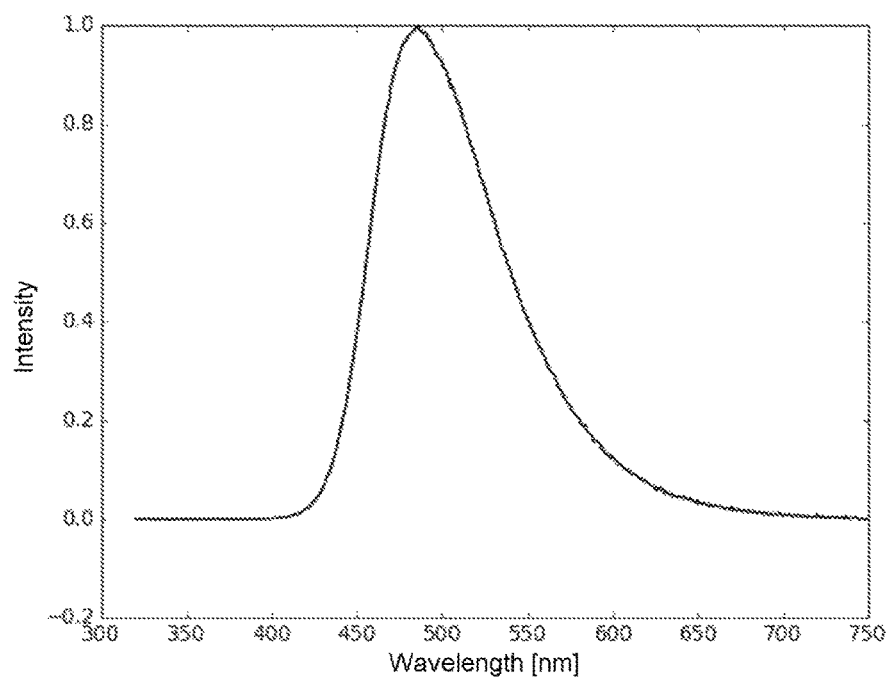
FIG. 13 Emission spectrum of Example 13 (10% in PMMA).

FIG. 13 shows the emission spectrum of Example 13 (10% in PMMA). The emission maximum is at 485 nm. The photoluminescence quantum yield (PLQY) is 78% and the half-height width is 0.43 eV. The emission lifetime is 12 µs.

Example 14

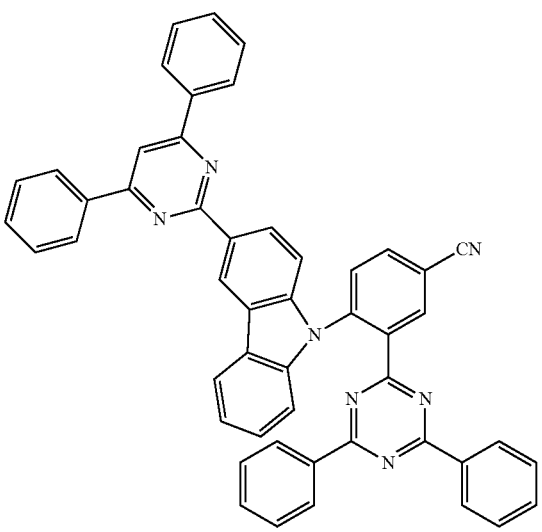 [SMILES: N#Cc1ccc(-n2c3ccccc3c3cc(-c4nc(-c5ccccc5)cc(-c5ccccc5)n4)ccc32)c(-c2nc(-c3ccccc3)nc(-c3ccccc3)n2)c1]

Example 14 was prepared according to GM6 (80% yield), according to GM8 with 3-bromocarbazole (65% yield), subsequent further reaction with bis(pinacol)boronic acid and subsequent further reaction with 2-chloro-4,6-diphenyl-1,3-pyrimidine.

MS (HPLC-MS), m/z (retention time): 729 (10.60 min).

Figure 14:
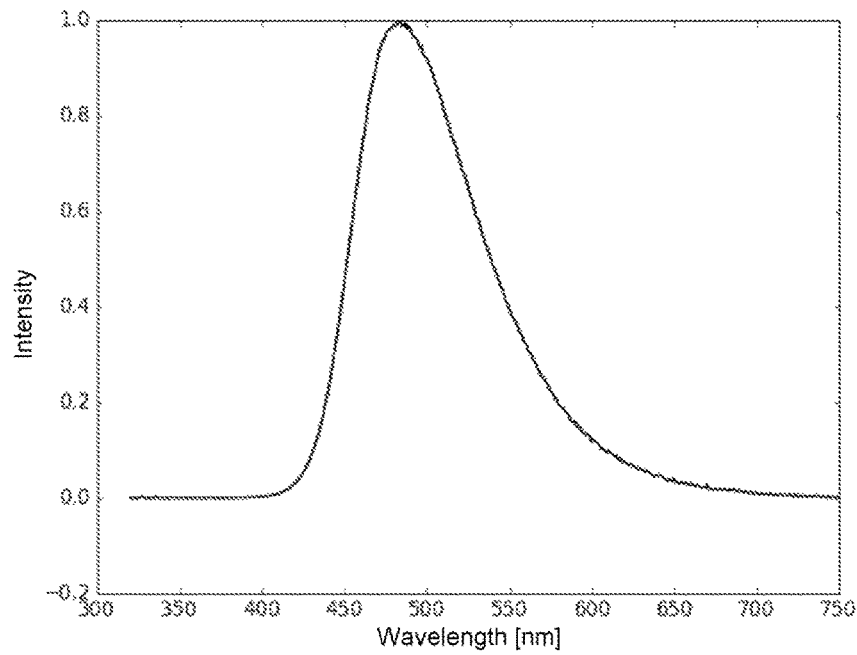
FIG. 14 Emission spectrum of Example 14 (10% in PMMA).

FIG. 14 shows the emission spectrum of Example 14 (10% in PMMA). The emission maximum is at 484 nm. The photoluminescence quantum yield (PLQY) is 73% and the half-height width is 0.44 eV. The emission lifetime is 25 µs.

Example 15

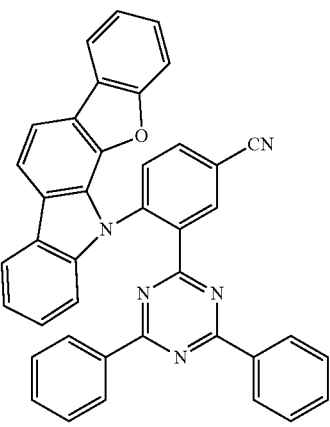 [SMILES: N#Cc1ccc(-n2c3ccccc3c3ccc4c5ccccc5oc4c32)c(-c2nc(-c3ccccc3)nc(-c3ccccc3)n2)c1]

Example 15 was prepared according to GM6 (80% yield) and GM8 (65% yield). MS (HPLC-MS), m/z (retention time): 589 (9.03 min).

Figure 15:
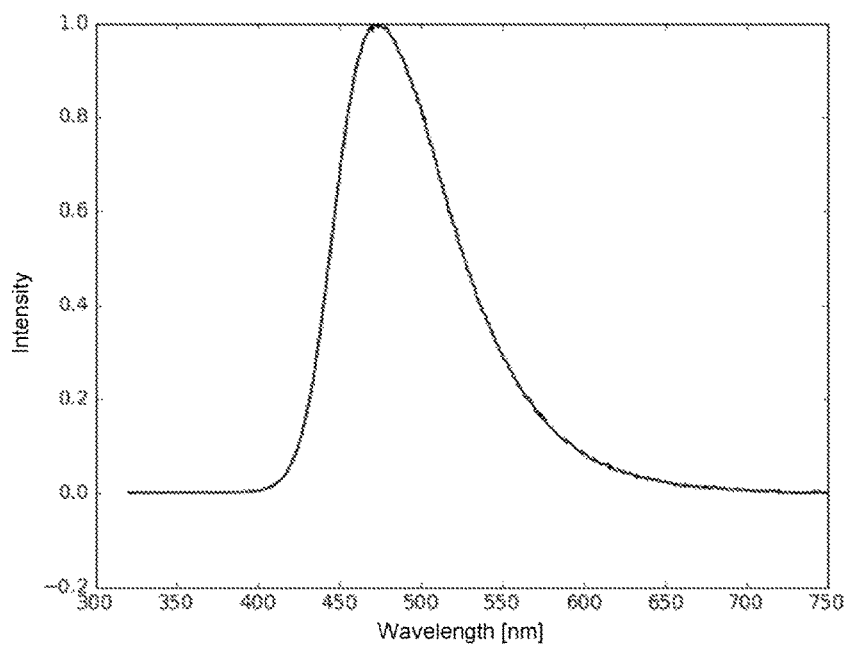

FIG. 15 shows the emission spectrum of Example 15 (10% in PMMA). The emission maximum is at 472 nm. The photoluminescence quantum yield (PLQY) is 63% and the half-height width is 0.44 eV. The emission lifetime is 5 µs.

Example 16

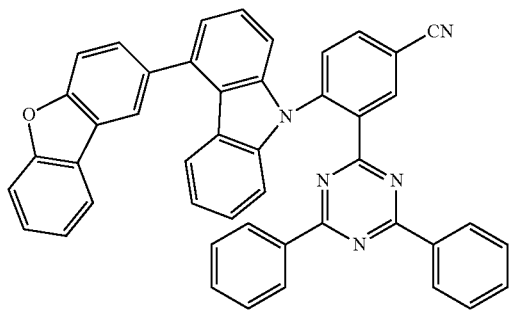 [SMILES: N#Cc1ccc(-n2c3ccccc3c3c(-c4ccc5oc6ccccc6c5c4)cccc32)c(-c2nc(-c3ccccc3)nc(-c3ccccc3)n2)c1]

Example 16 was prepared according to GM6 (80% yield) and GM8 (100% yield). MS (HPLC-MS), m/z (retention time): 666 (10.67 min).

Figure 16:
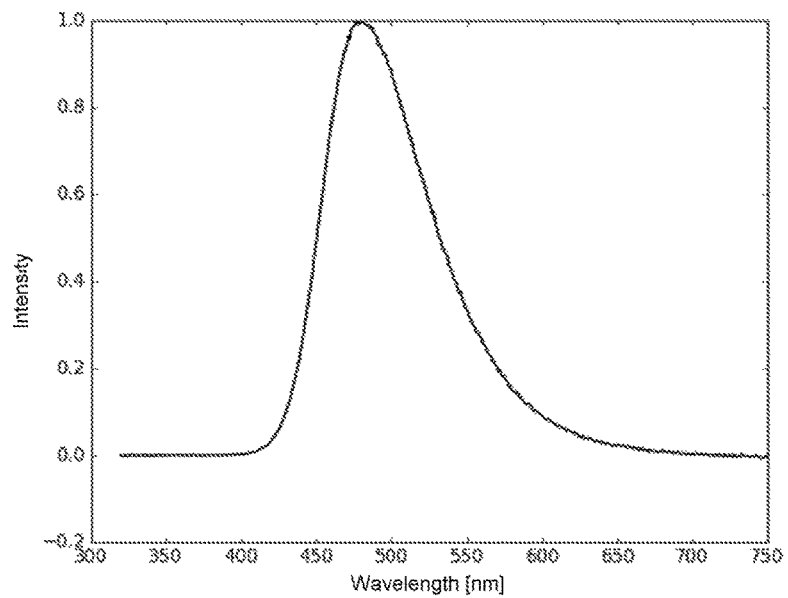
FIG. 16 Emission spectrum of Example 16 (10% in PMMA).

FIG. 16 shows the emission spectrum of Example 16 (10% in PMMA). The emission maximum is at 479 nm. The photoluminescence quantum yield (PLQY) is 81% and the half-height width is 0.42 eV. The emission lifetime is 6 μs.

Example 17

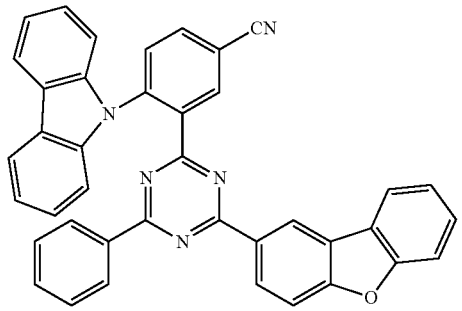 [SMILES: N#Cc1ccc(-n2c3ccccc3c3ccccc32)c(-c2nc(-c3ccccc3)nc(-c3ccc4oc5ccccc5c4c3)n2)c1]

Example 17 was prepared according to GM6, except using 2-chloro-4-(2-dibenzofuranyl)-6-phenyl-1,3,5-triazine instead of 2-chloro-4,6-diphenyl-1,3,5-triazine (85% yield), and GM8 (10% yield).

Figure 17:
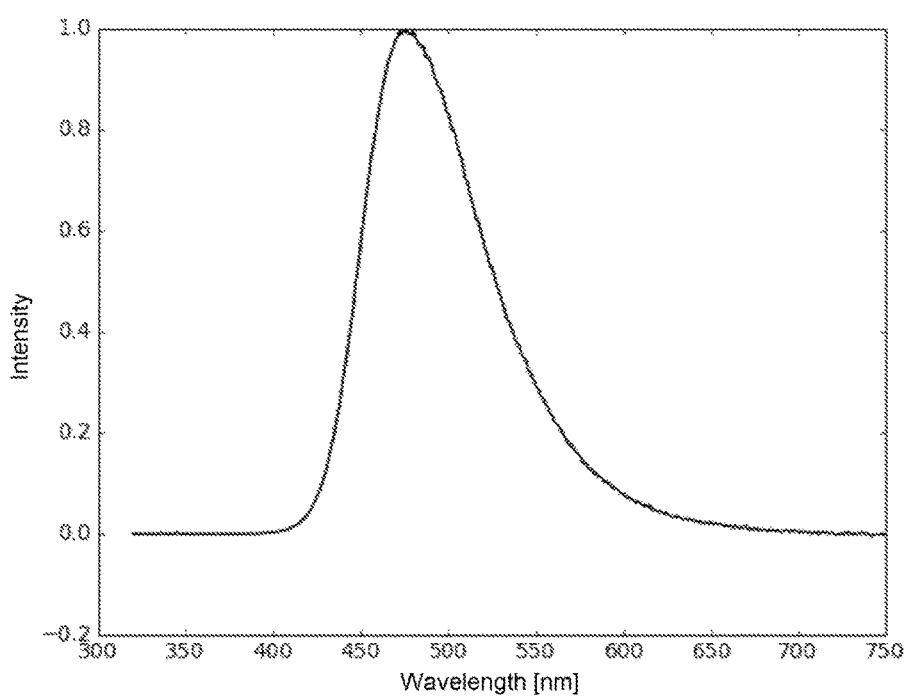
FIG. 17 Emission spectrum of Example 17 (10% in PMMA).

FIG. 17 shows the emission spectrum of Example 17 (10% in PMMA). The emission maximum is at 474 nm. The photoluminescence quantum yield (PLQY) is 74% and the half-height width is 0.42 eV. The emission lifetime is 17 μs.

OLED Component: Examples

Accelerated lifetime measurements were conducted (for example by applying an elevated current density). By way of example, LT80 values at 500 cd/m² are determined by the following equation:

$$LT80\left(500\frac{cd^2}{m^2}\right) = LT80(L_0)\left(\frac{500\frac{cd^2}{m^2}}{L_0}\right)^{-1.6}$$

where $L_0$ is the starting luminance at the current density used.

Examples D1 and D2

Example 5 was tested in the OLED components D1 and D2 with the following structures (the proportion of the molecule according to the invention in the emission layer is reported in percent by mass):

| Layer | Thickness | D1 |
|---|---|---|
| 10 | 100 nm | Al |
| 9 | 2 nm | Liq |
| 8 | 30 nm | TPBi |
| 7 | 10 nm | DPEPO |
| 6 | 20 nm | 5 (20%):DPEPO |
| 5 | 10 nm | CzSi |
| 4 | 20 nm | TCTA |
| 3 | 70 nm | NPB |
| 2 | 20 nm | m-MTDATA |
| 1 | 130 nm | ITO |
| Substrate | | Glass |

For component D1, an external quantum efficiency at 1000 cd/m² of 12.7%±0.4 was determined. The emission maximum is at 479 nm; CIEx was determined as 0.32 and CIEy: 0.17 at 6 V.

| Layer | Thickness | D2 |
|---|---|---|
| 7 | 100 nm | Al |
| 6 | 2 nm | Liq |
| 5 | 40 nm | NBPhen |
| 4 | 20 nm | 5 (10%):mCBP |
| 3 | 10 nm | TCTA |
| 2 | 80 nm | NPB |
| 1 | 130 nm | ITO |
| Substrate | | glass |

For component D2, an external quantum efficiency at 1000 cd/m² of 8.2%±0.1 and an LT80 at 500 cd/m² of 10 h were determined from the accelerated lifetime measurements. The emission maximum is at 463 nm; CIEx was determined as 0.16 and CIEy: 0.20 at 6 V.

Examples D3, D4, D5, D6 and D7

Example 3 was tested in OLED components D3, D4, D5, D6 and D7 with the following structures (the proportion of the molecule according to the invention in the emission layer is reported in percent by mass):

| Layer | Thickness | D3 | D4 | D5 | D6 |
|---|---|---|---|---|---|
| 8 | 100 nm | Al | Al | Al | Al |
| 7 | 2 nm | Liq | Liq | Liq | Liq |
| 6 | 40 nm | NBPhen | NBPhen | NBPhen | NBPhen |
| 5 | 20 nm | 3 (20%):mCBP | 3 (10%):mCBP | 3 (10%):T2T (15%):mCBP (75%) | 3 (20%):T2T (15%):mCBP (65%) |
| 4 | 5 nm | mCBP | mCBP | mCBP | mCBP |
| 3 | 10 nm | TCTA | TCTA | TCTA | TCTA |

| Layer | Thickness | D3 | D4 | D5 | D6 |
|---|---|---|---|---|---|
| 2 | 75 nm | NPB | NPB | NPB | NPB |
| 1 | 130 nm | ITO | ITO | ITO | ITO |
| Substrate | | Glass | Glass | Glass | Glass |

For component D3, an external quantum efficiency at 1000 cd/m$^2$ of 14.8%±0.1 and an LT80 at 500 cd/m$^2$ of 1277 h were determined from the accelerated lifetime measurements. The emission maximum is at 488 nm; CIEx was determined as 0.23 and CIEy: 0.41 at 6 V. For component D4, an external quantum efficiency at 1000 cd/m$^2$ of 12.5%±0.1 and an LT80 at 500 cd/m$^2$ of 817 h were determined from the accelerated lifetime measurements. The emission maximum is at 480 nm; CIEx was determined as 0.21 and CIEy: 0.36 at 6 V. For component D5, an external quantum efficiency at 1000 cd/m$^2$ of 13.9%±0.1 and an LT80 at 500 cd/m$^2$ of 553 h were determined from the accelerated lifetime measurements. The emission maximum is at 487 nm; CIEx was determined as 0.21 and CIEy: 0.38 at 6 V. For component D6, an external quantum efficiency at 1000 cd/m$^2$ of 13.3%±0.2 and an LT80 at 500 cd/m$^2$ of 840 h were determined from the accelerated lifetime measurements. The emission maximum is at 493 nm; CIEx was determined as 0.23 and CIEy: 0.42 at 6 V.

Example D7

| Layer | Thickness | D7 |
|---|---|---|
| 9 | 100 nm | Al |
| 8 | 2 nm | Liq |
| 7 | 30 nm | NBPhen |
| 6 | 10 nm | T2T |
| 5 | 20 nm | 3 (20%):mCBP (65%):T2T (15%) |
| 4 | 5 nm | mCBP |
| 3 | 10 nm | TCTA |
| 2 | 75 nm | NPB |
| 1 | 130 nm | ITO |
| Substrate | | Glass |

For component D7, an external quantum efficiency at 1000 cd/m$^2$ of 17.2%±0.1 and an LT80 at 500 cd/m$^2$ of 640 h were determined from the accelerated lifetime measurements. The emission maximum is at 493 nm; CIEx was determined as 0.23 and CIEy: 0.45 at 6 V.

Examples D8 and D9

Example 6 was tested in OLED components D8 and D9 with the following structures (the proportion of the molecule according to the invention in the emission layer is reported in percent by mass):

| Layer | | Thickness D1 | Thickness D2 |
|---|---|---|---|
| 8 | Al | 100 nm | 100 nm |
| 7 | Liq | 2 nm | 2 nm |
| 6 | NBPhen | 40 nm | 40 nm |
| 5 | 6 (20%):mCBP | 50 nm | 60 nm |
| 4 | mCBP | 10 nm | 10 nm |
| 3 | TCTA | 10 nm | 10 nm |
| 2 | NPB | 115 nm | 30 nm |
| 1 | ITO | 130 nm | 130 nm |
| Substrate | Glass | | |

For component D8, an external quantum efficiency at 1000 cd/m$^2$ of 17.7%±0.2 and an LT80 at 500 cd/m$^2$ of 539 h were determined from the accelerated lifetime measurements. The emission maximum is at 482 nm; CIEx was determined as 0.17 and CIEy: 0.34 at 6 V. For component D9, an external quantum efficiency at 1000 cd/m$^2$ of 14.9%±0.2 and an LT80 at 500 cd/m$^2$ of 480 h were determined from the accelerated lifetime measurements. The emission maximum is at 475 nm; CIEx was determined as 0.19 and CIEy: 0.33 at 6 V.

Example D10

Example 13 was tested in OLED component D10 with the following structure (the proportion of the molecule according to the invention in the emission layer is reported in percent by mass):

| Layer | Thickness | |
|---|---|---|
| 8 | 100 nm | Al |
| 7 | 2 nm | Liq |
| 6 | 40 nm | NBPhen |
| 5 | 30 nm | 13 (20%):9-[3,5-bis(2-dibenzofuranyl)phenyl]-9H-carbazole |
| 4 | 8 nm | 9-[3,5-bis(2-dibenzofuranyl)phenyl]-9H-carbazole |
| 3 | 10 nm | TCTA |
| 2 | 62 nm | NPB |
| 1 | 130 nm | ITO |
| Substrate | | Glass |

For component D10, an external quantum efficiency at 1000 cd/m$^2$ of 14.5%±0.8 and an LT80 at 500 cd/m$^2$ of 91 h were determined from the accelerated lifetime measurements. The emission maximum is at 480 nm; CIEx was determined as 0.20 and CIEy: 0.37 at 6 V.

Examples D11 and D12

Example 5 and Example 6 were tested in OLED components D11 and D12 with the following structures (the proportion of the molecule according to the invention in the emission layer is reported in percent by mass):

| Layer | Thickness | D11 | D12 |
|---|---|---|---|
| 9 | 100 nm | Al | Al |
| 8 | 2 nm | Liq | Liq |
| 7 | 30 nm | NBPhen | NBPhen |
| 6 | 40 nm | 5 (30%):mCBP | 6 (30%):mCBP |
| 5 | 10 nm | 5 (10%):mCBP | 6 (10%):mCBP |
| 4 | 10 nm | mCBP | mCBP |
| 3 | 10 nm | TCTA | TCTA |
| 2 | 100 nm | NPB | NPB |
| 1 | 130 nm | ITO | ITO |
| Substrate | | Glass | Glass |

For component D11, an external quantum efficiency at 1000 cd/m² of 15.2%±0.1 and an LT80 at 500 cd/m² of 110 h were determined from the accelerated lifetime measurements. The emission maximum is at 474 nm; CIEx was determined as 0.15 and CIEy: 0.24 at 6 V. For component D12, an external quantum efficiency at 1000 cd/m² of 16.3%±0.1 and an LT80 at 500 cd/m² of 431 h were determined from the accelerated lifetime measurements. The emission maximum is at 480 nm; CIEx was determined as 0.17 and CIEy: 0.33 at 6 V.

Further examples of molecules according to the invention:

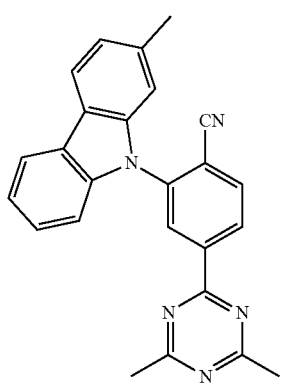

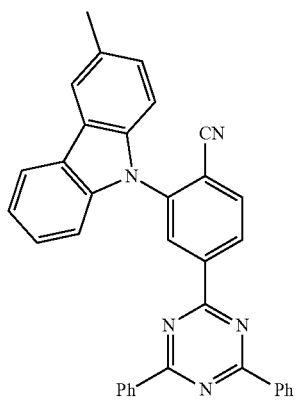

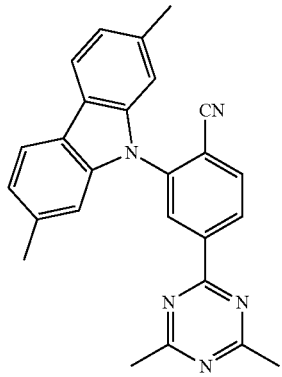

-continued

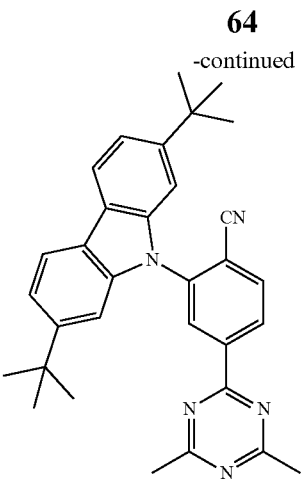

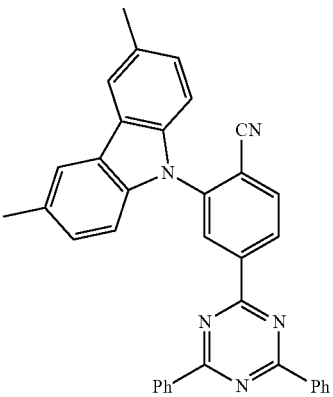

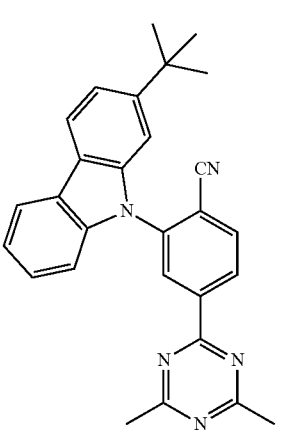

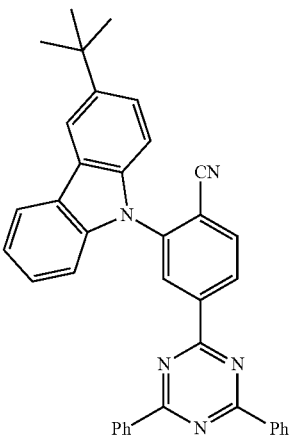

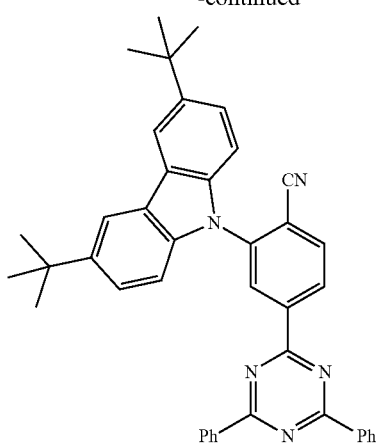
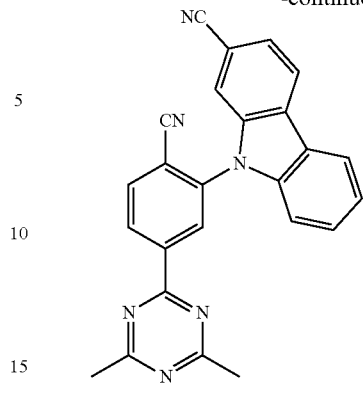
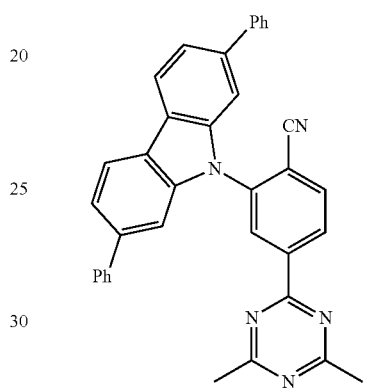
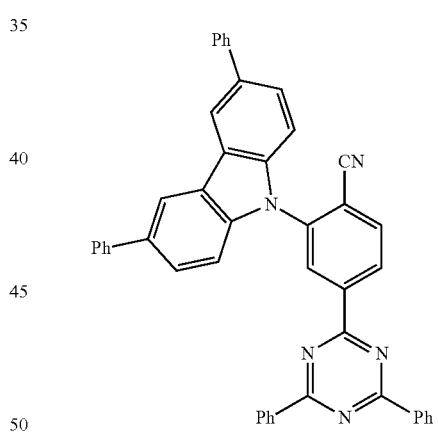
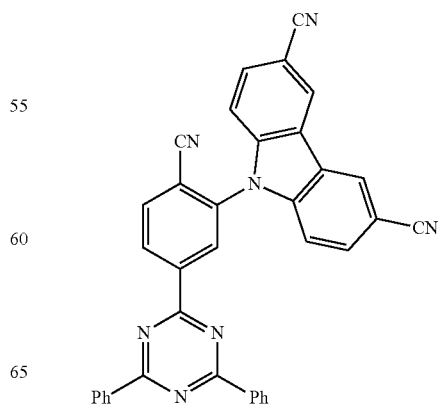

-continued
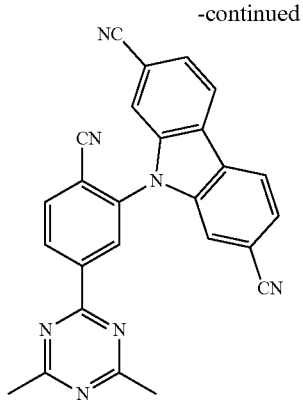
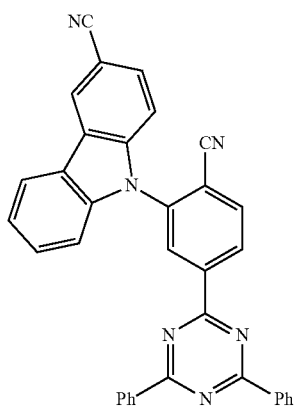
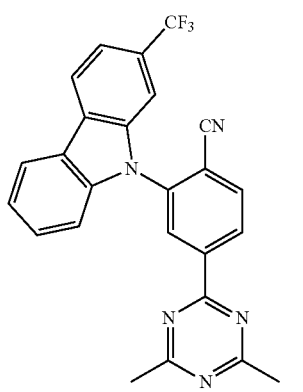
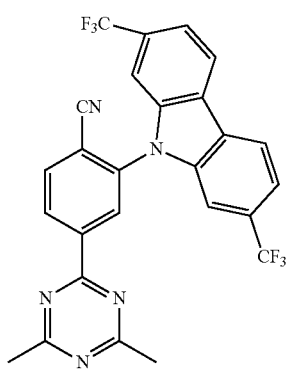
-continued
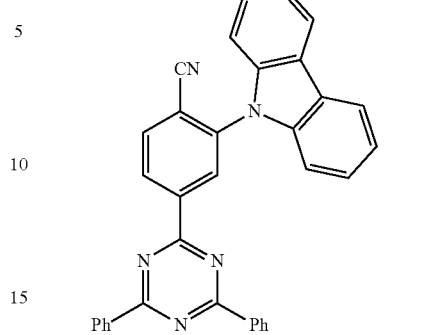
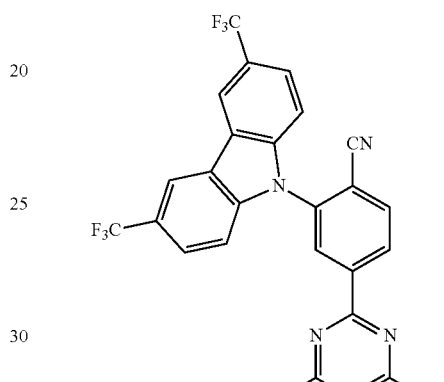
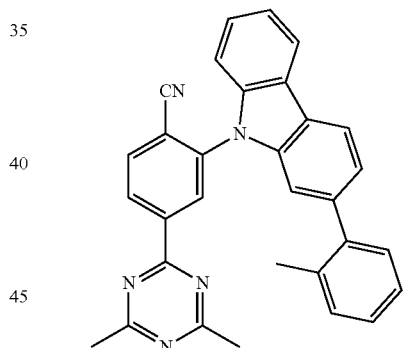
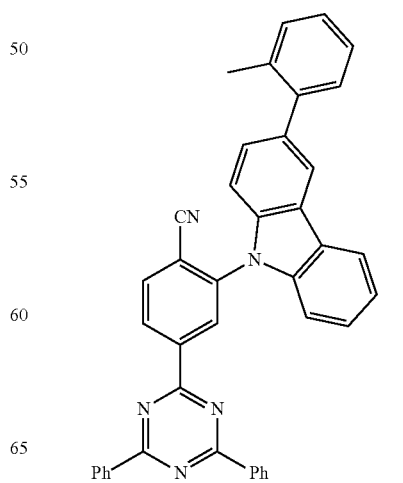

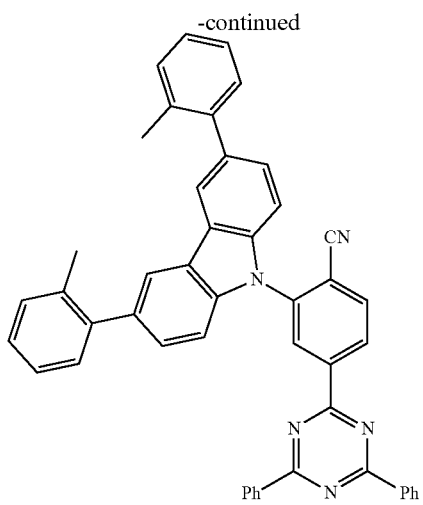
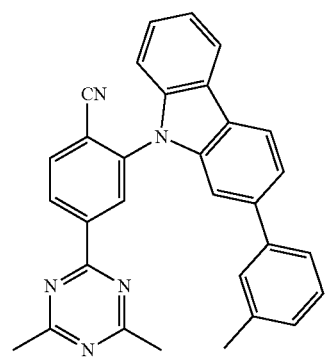
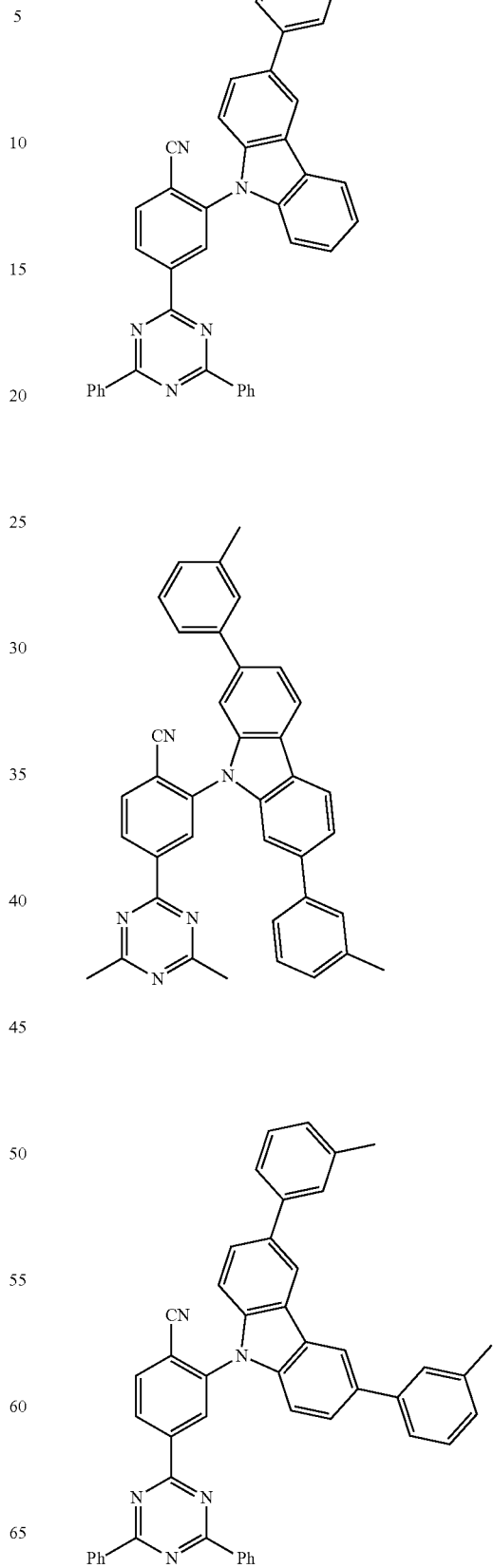

71
-continued
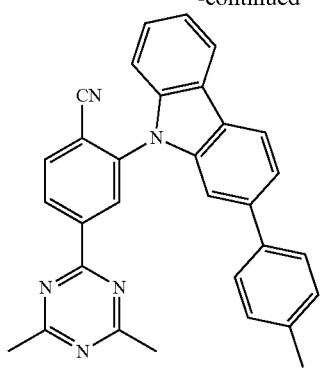
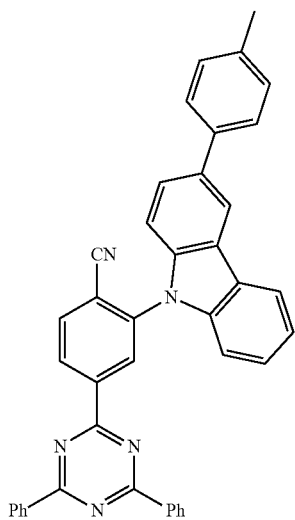
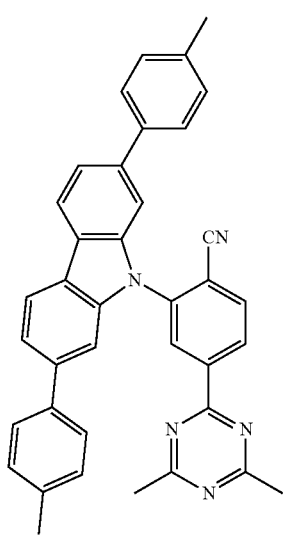
72
-continued
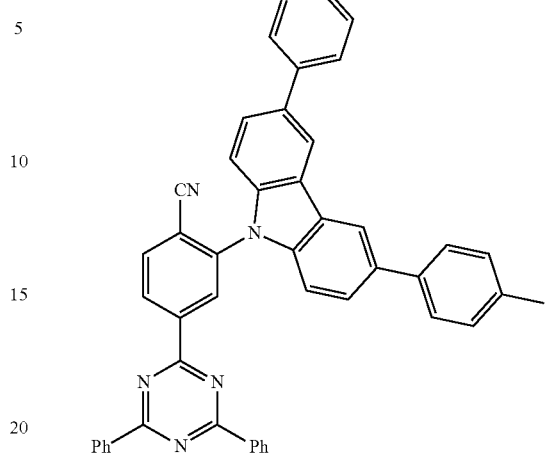
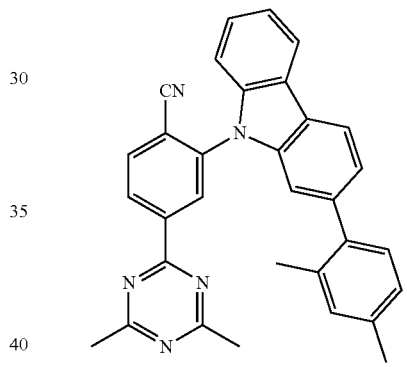
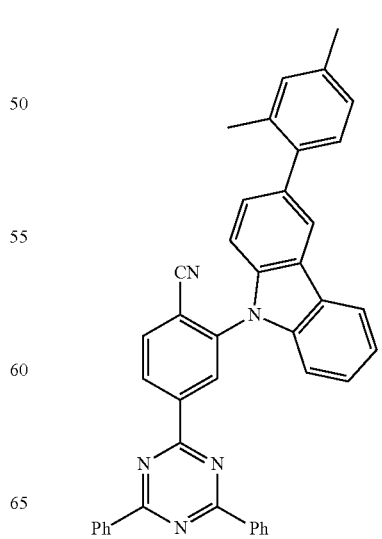

73
-continued
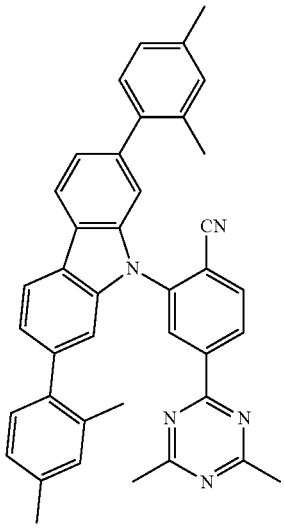
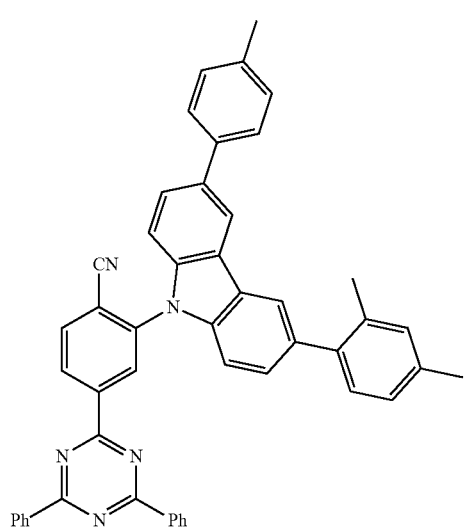
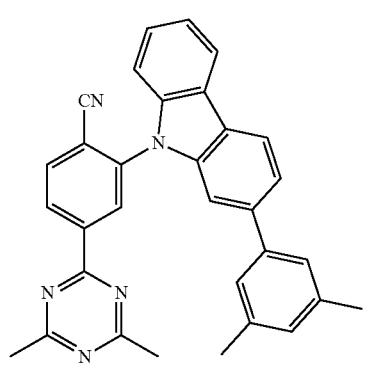
74
-continued
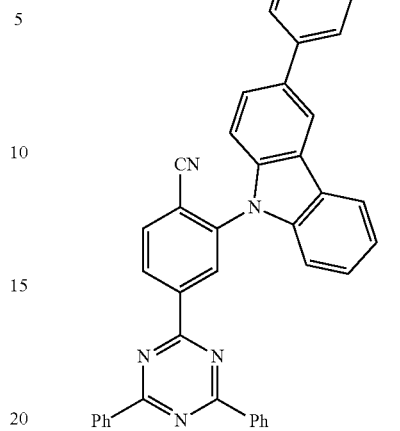

75
-continued
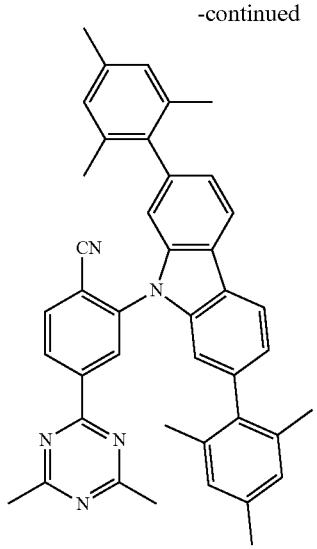
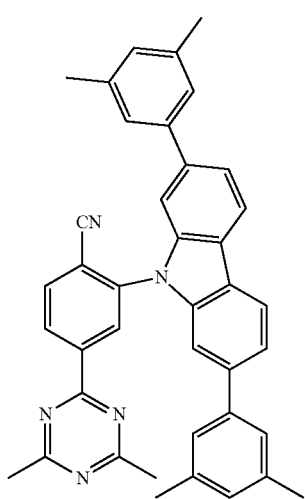
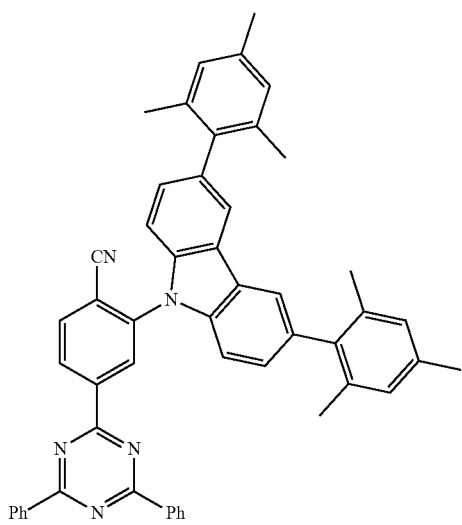
76
-continued
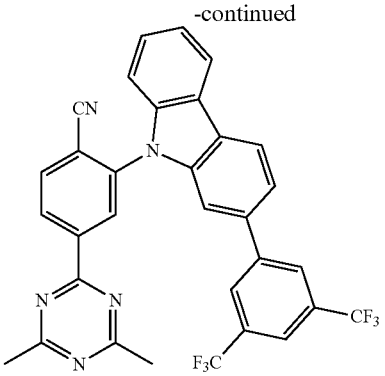
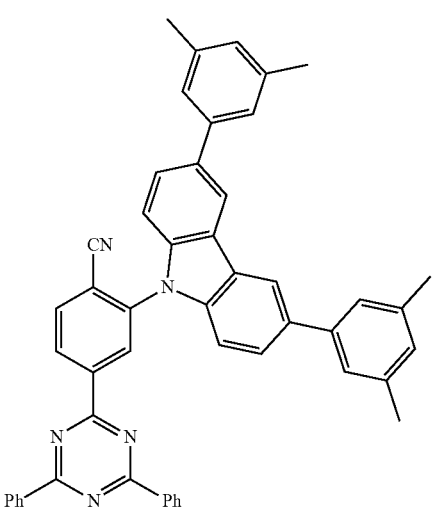
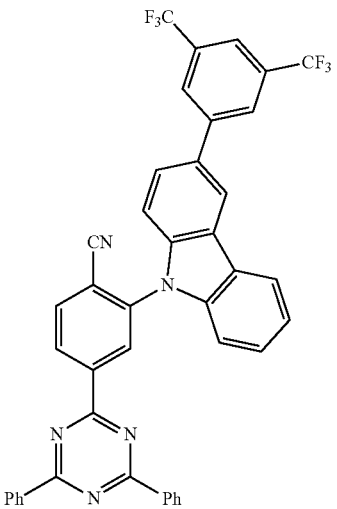

77
-continued
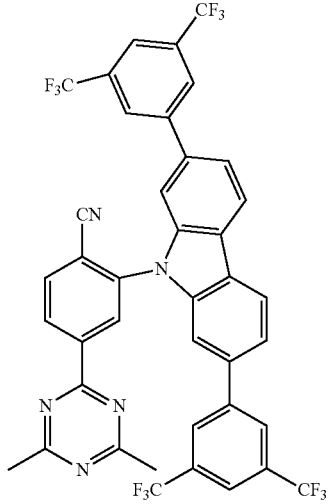
78
-continued
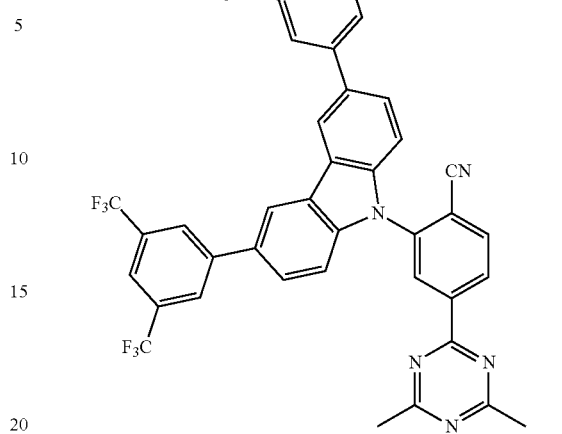
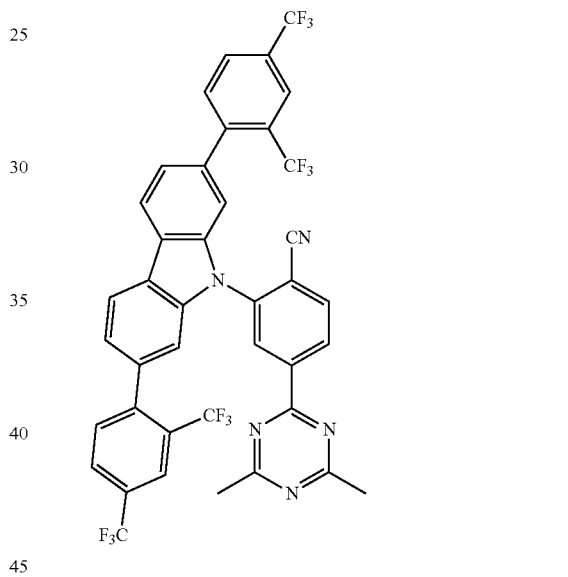
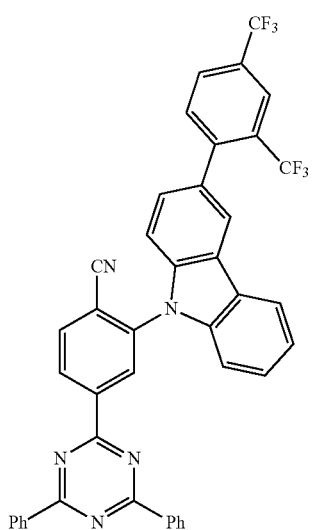 [SMILES: N#Cc1ccc(-c2nc(-c3ccccc3)nc(-c3ccccc3)n2)cc1-n1c2ccccc2c2cc(-c3ccc(C(F)(F)F)cc3C(F)(F)F)ccc21]
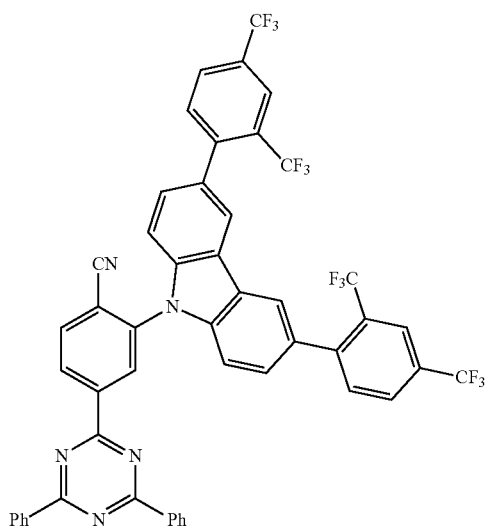

79
-continued
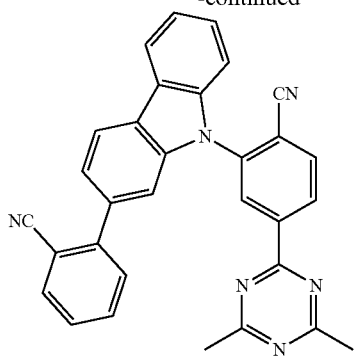
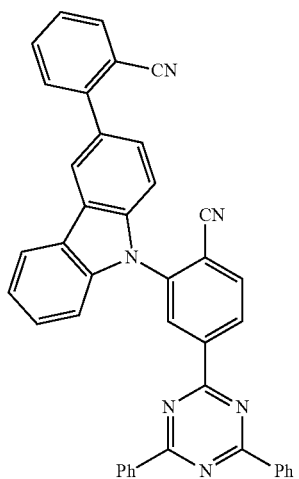
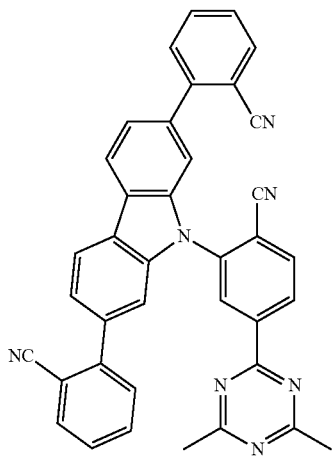
80
-continued
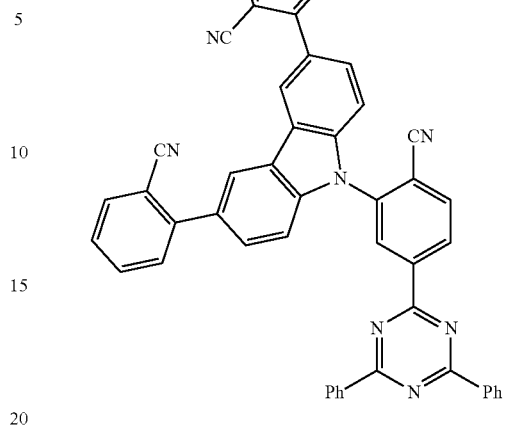
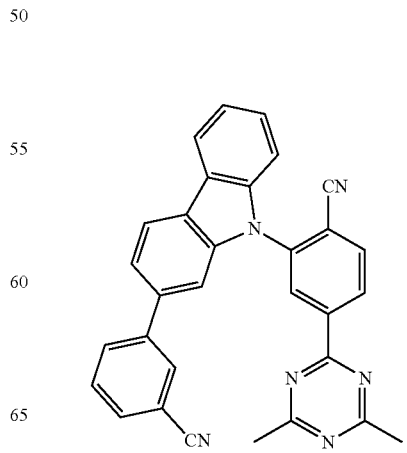

81
-continued
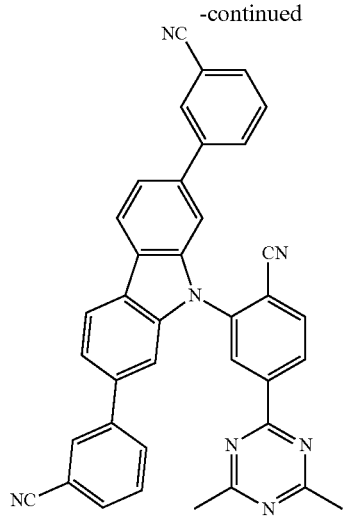
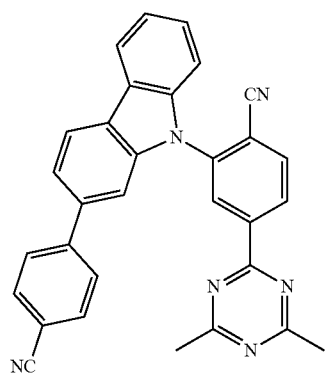
82
-continued
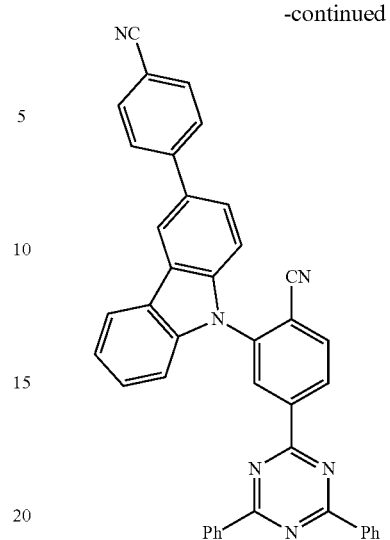
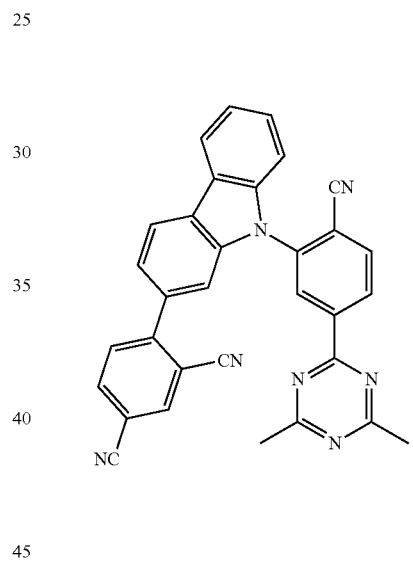
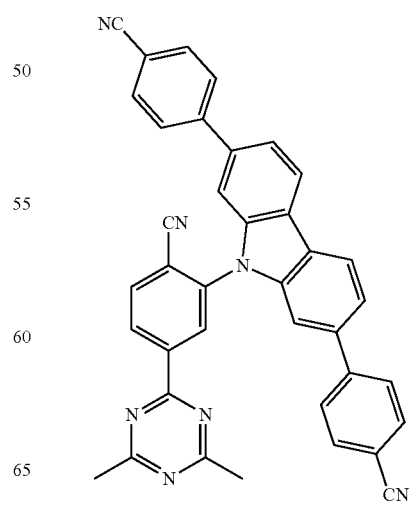

-continued
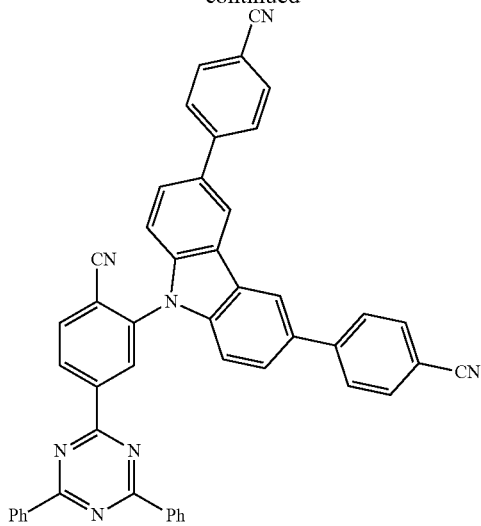
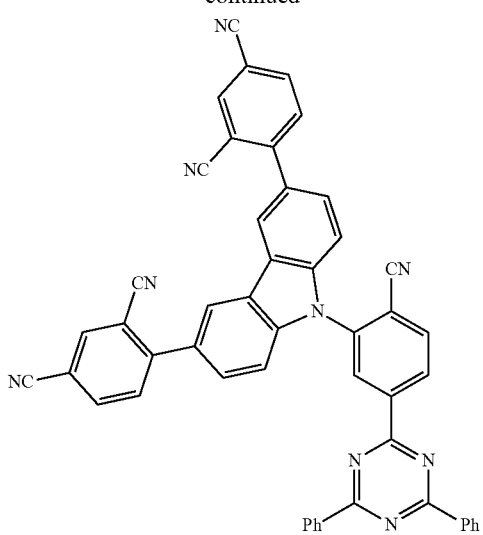
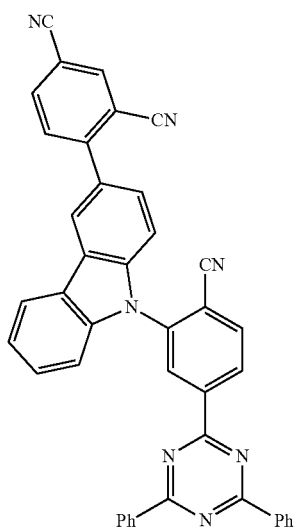
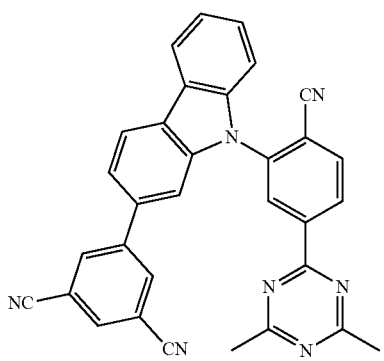
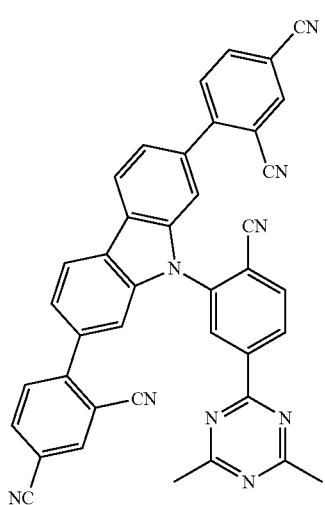
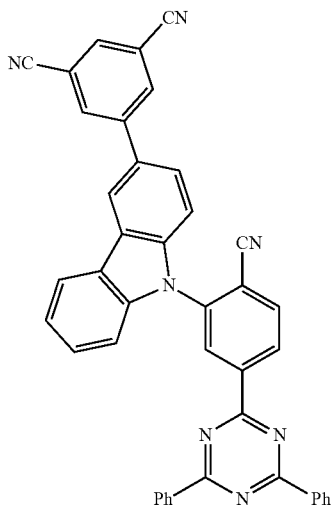

85
-continued
86
-continued
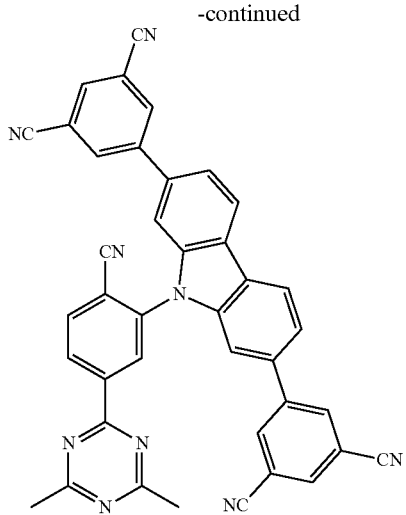
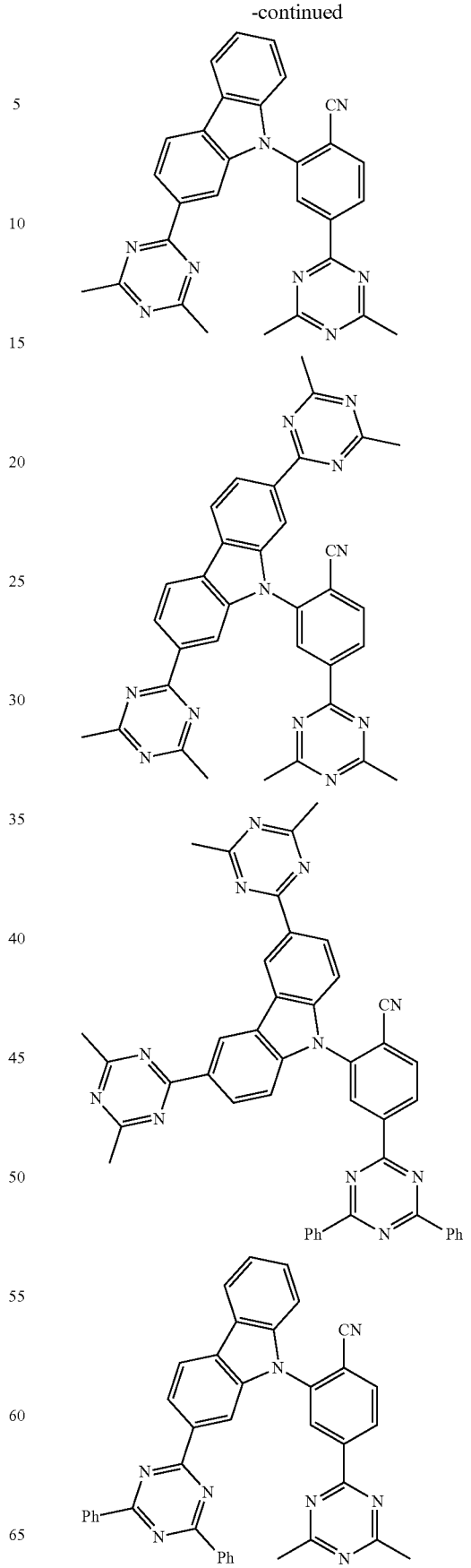

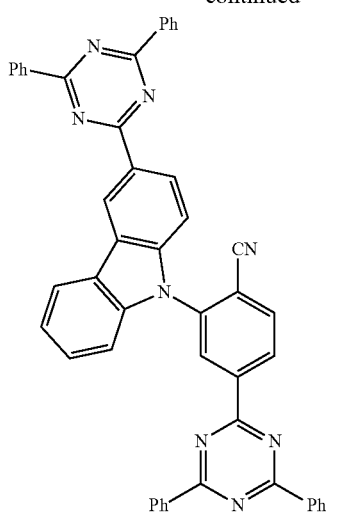
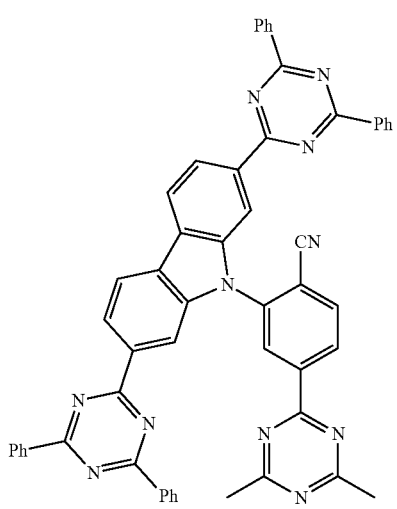
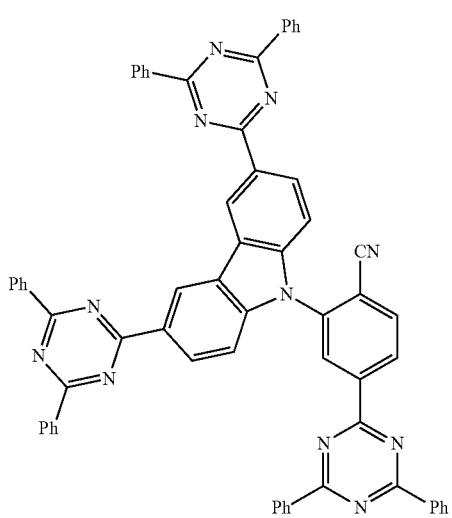 [SMILES: N#Cc1ccc(-c2nc(-c3ccccc3)nc(-c3ccccc3)n2)cc1-n1c2ccc(-c3nc(-c4ccccc4)nc(-c4ccccc4)n3)cc2c2cc(-c3nc(-c4ccccc4)nc(-c4ccccc4)n3)ccc21]
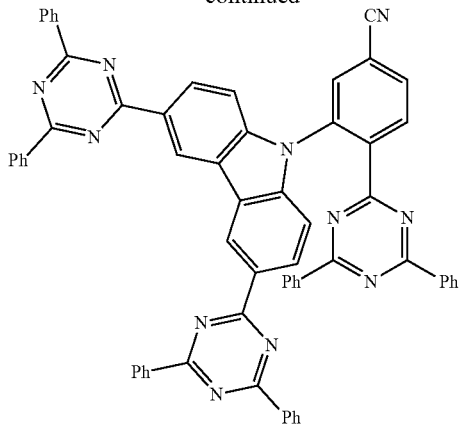
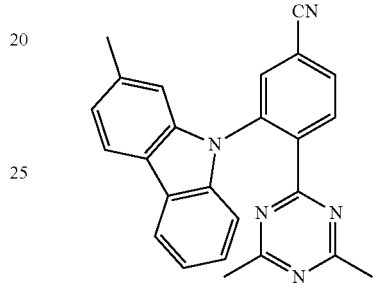
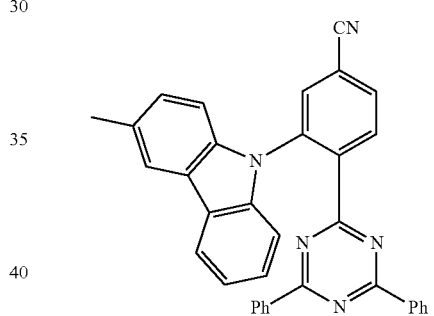
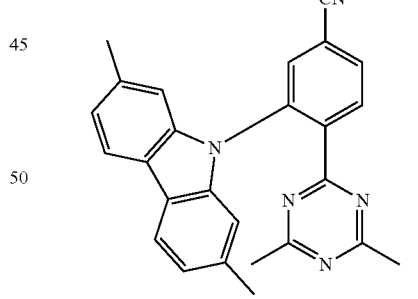
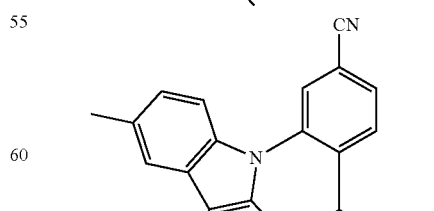
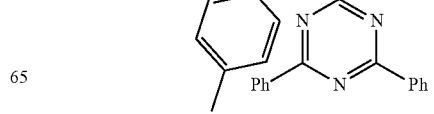

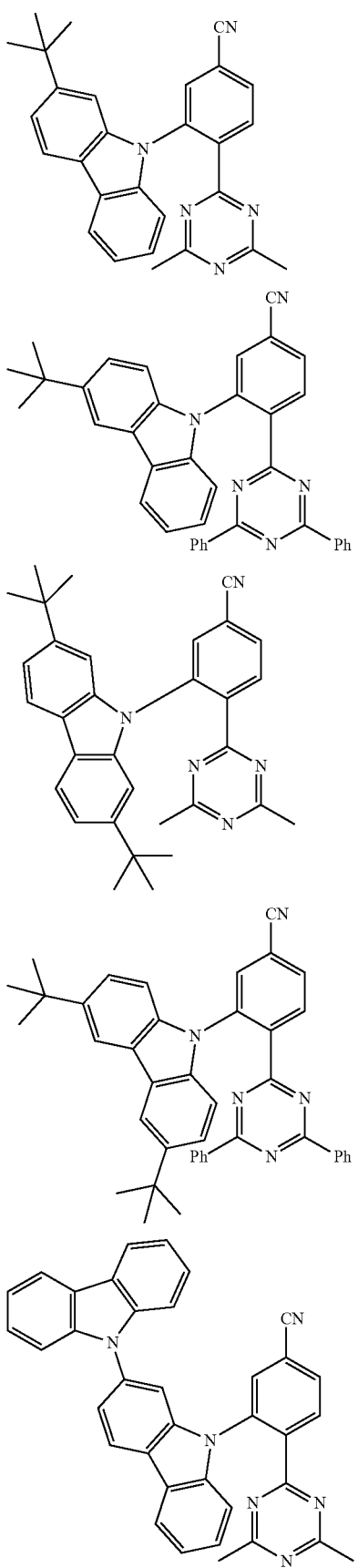
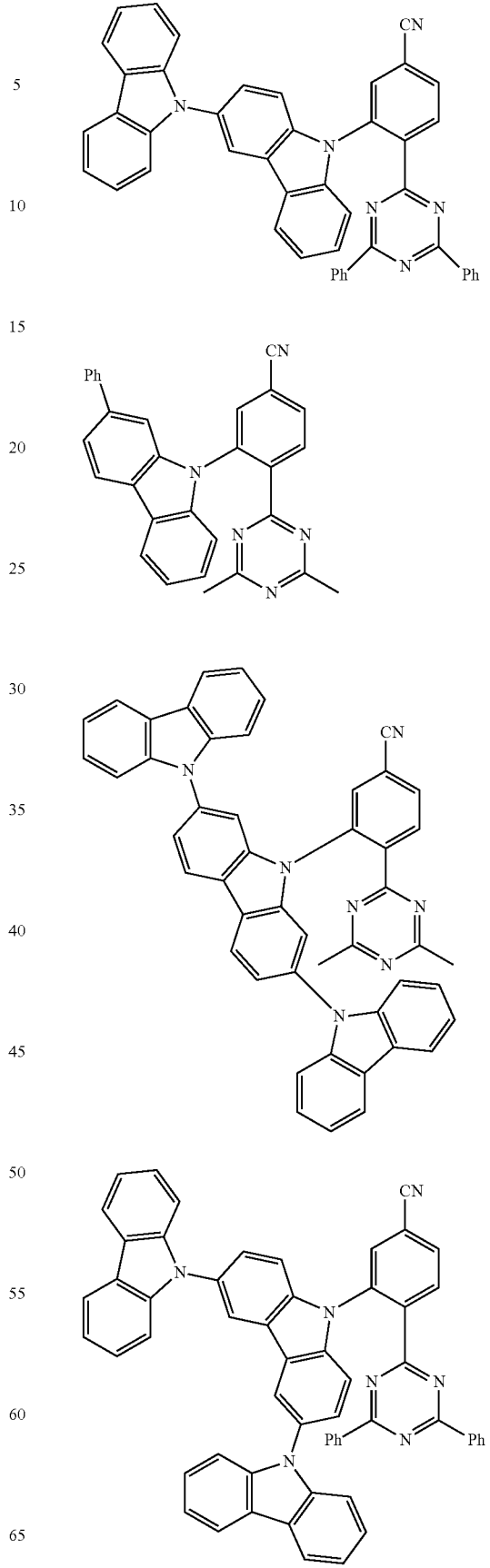

-continued
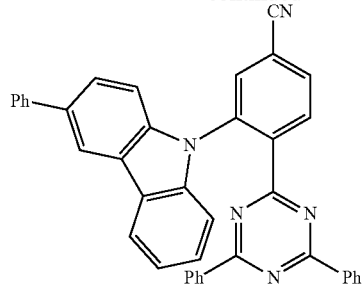
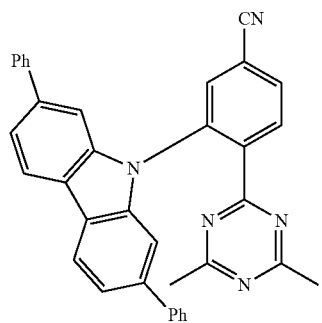
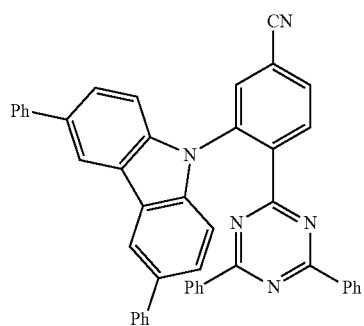
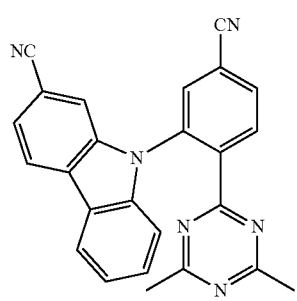
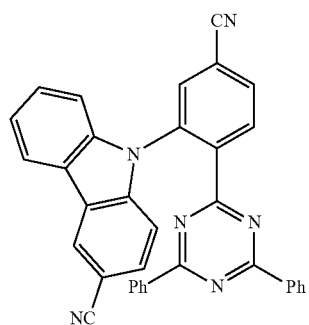
-continued
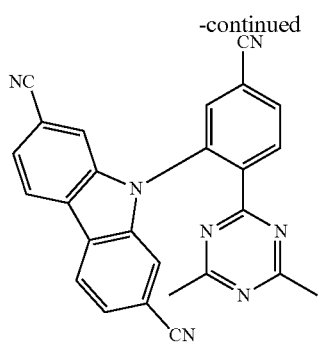
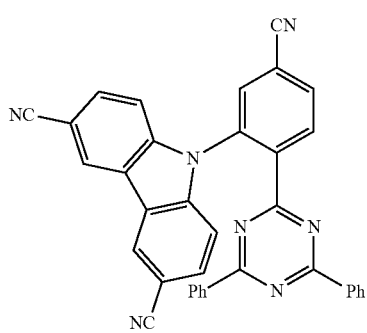
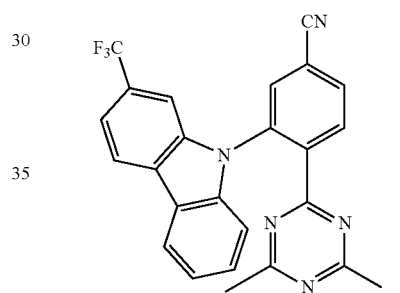
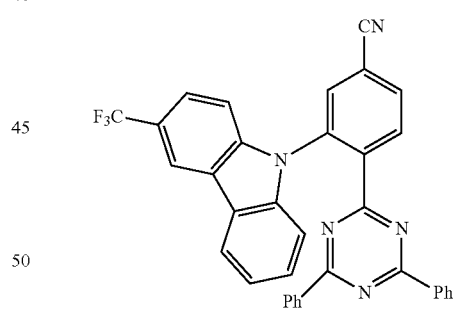
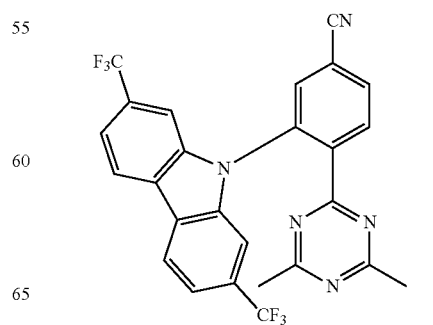

-continued
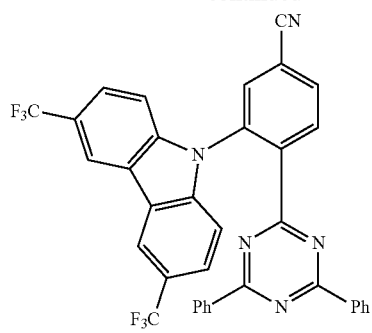
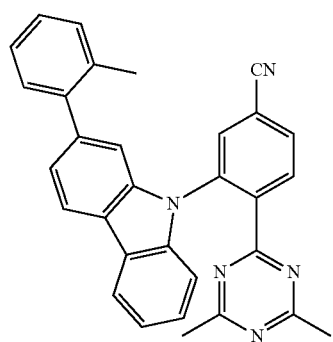
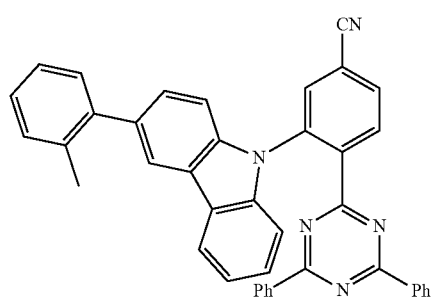
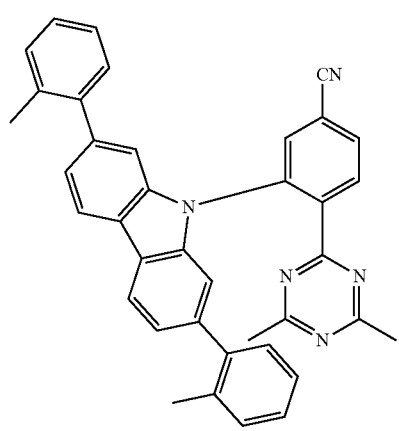
-continued
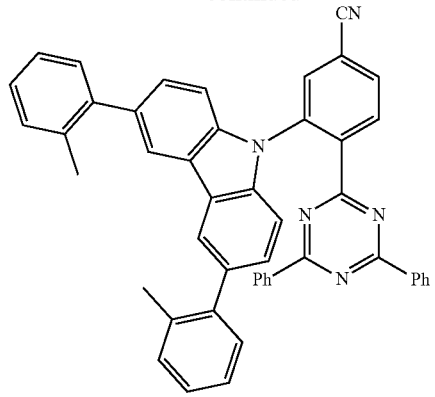
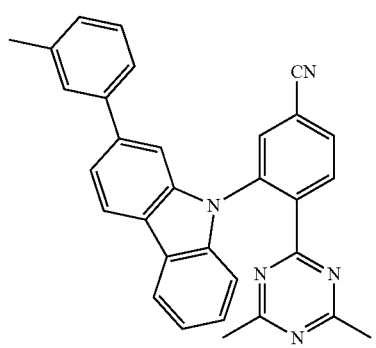
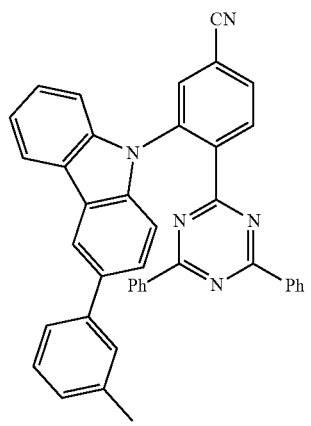
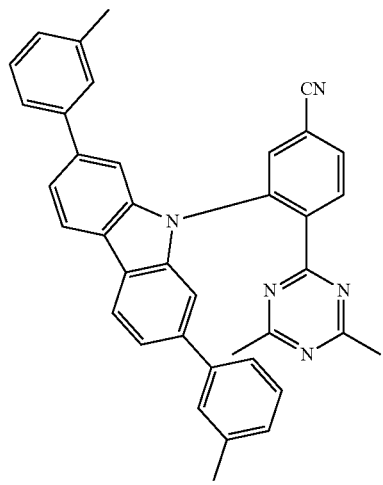

95
-continued
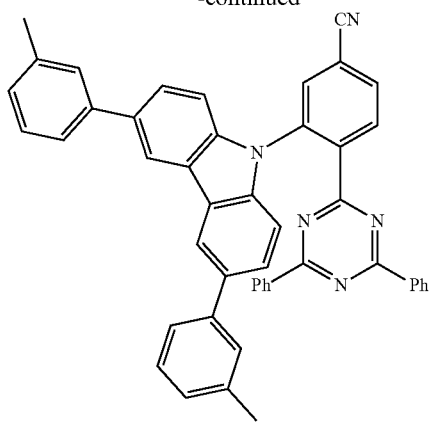
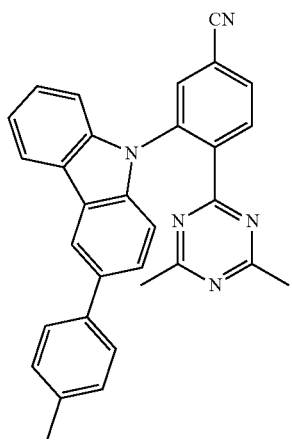
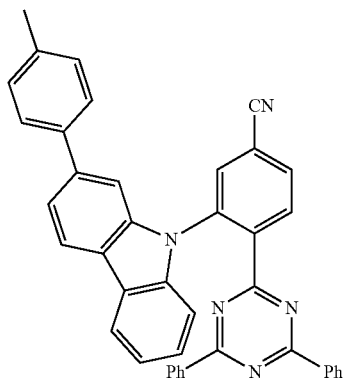
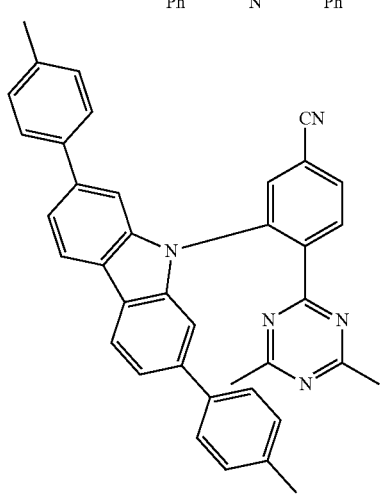
96
-continued
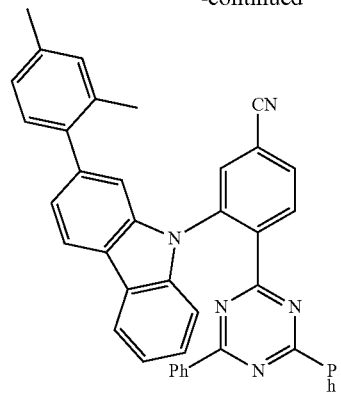
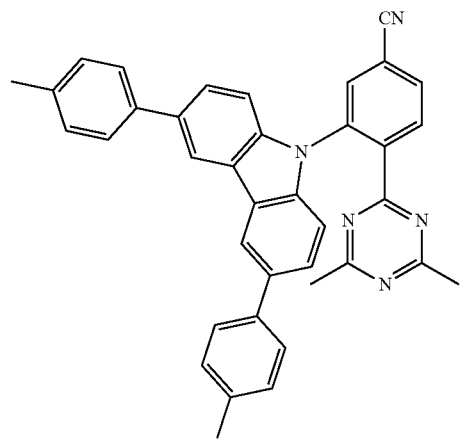
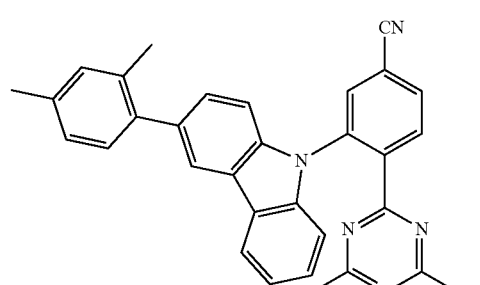
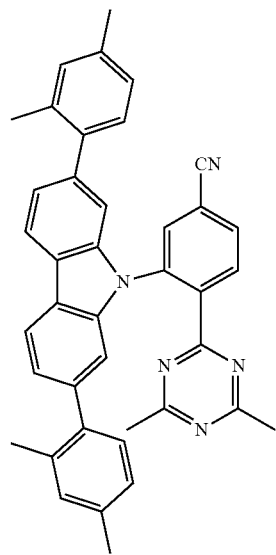

97
-continued
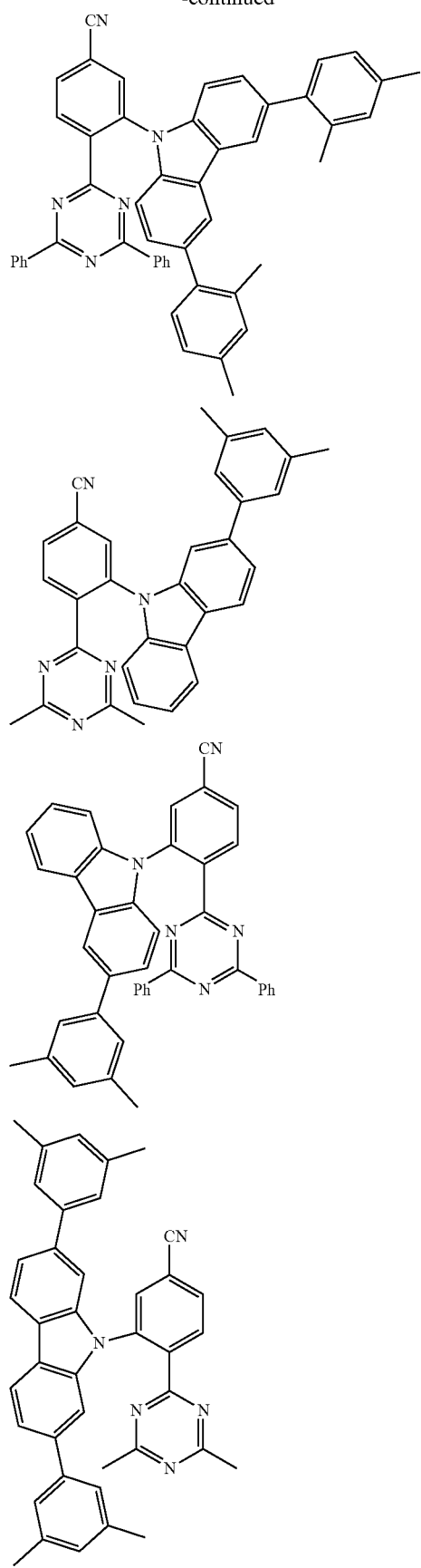
98
-continued
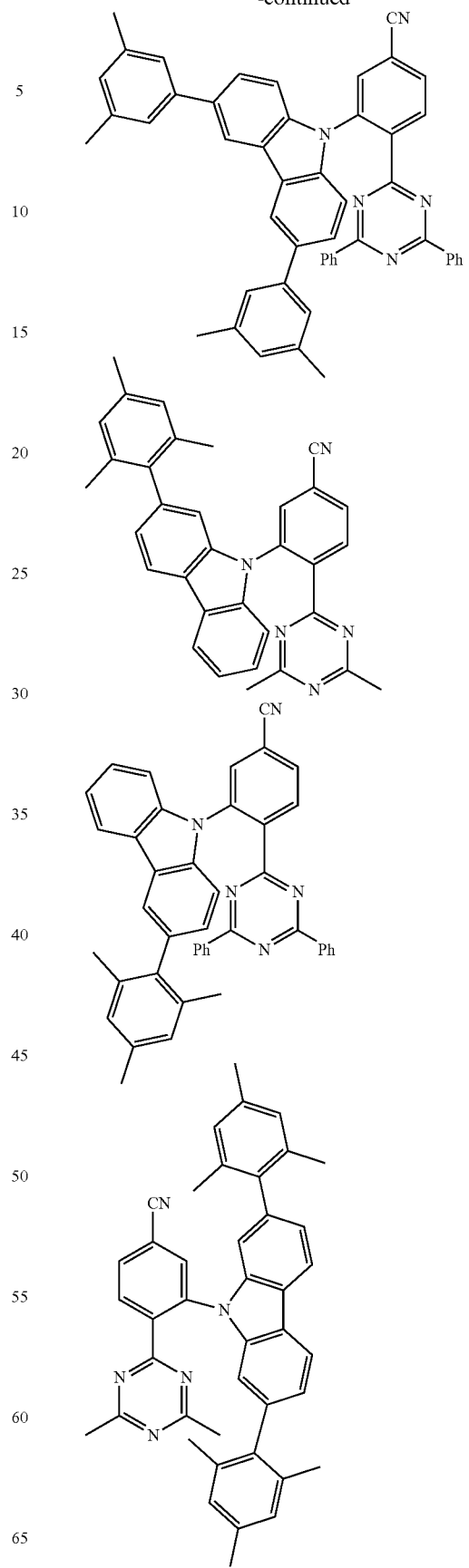

99
-continued
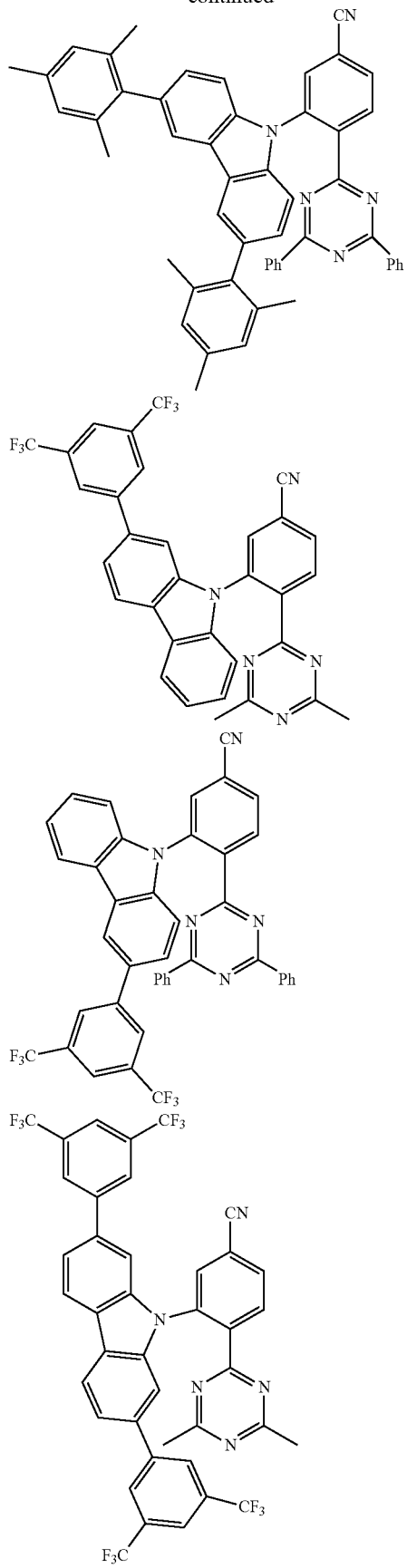
100
-continued
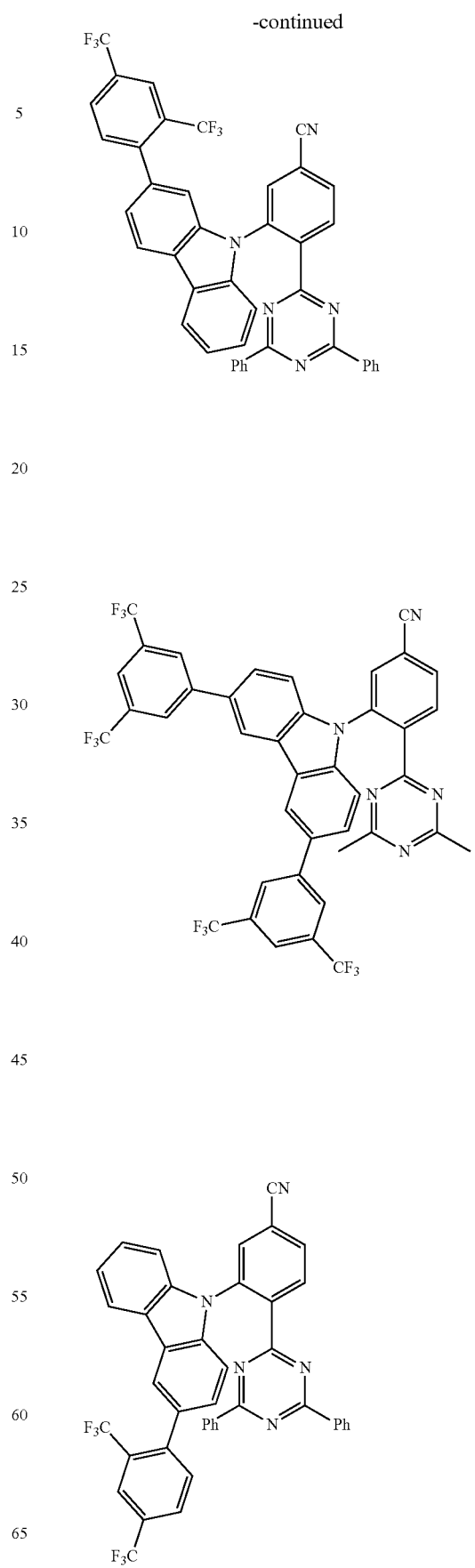

101
-continued
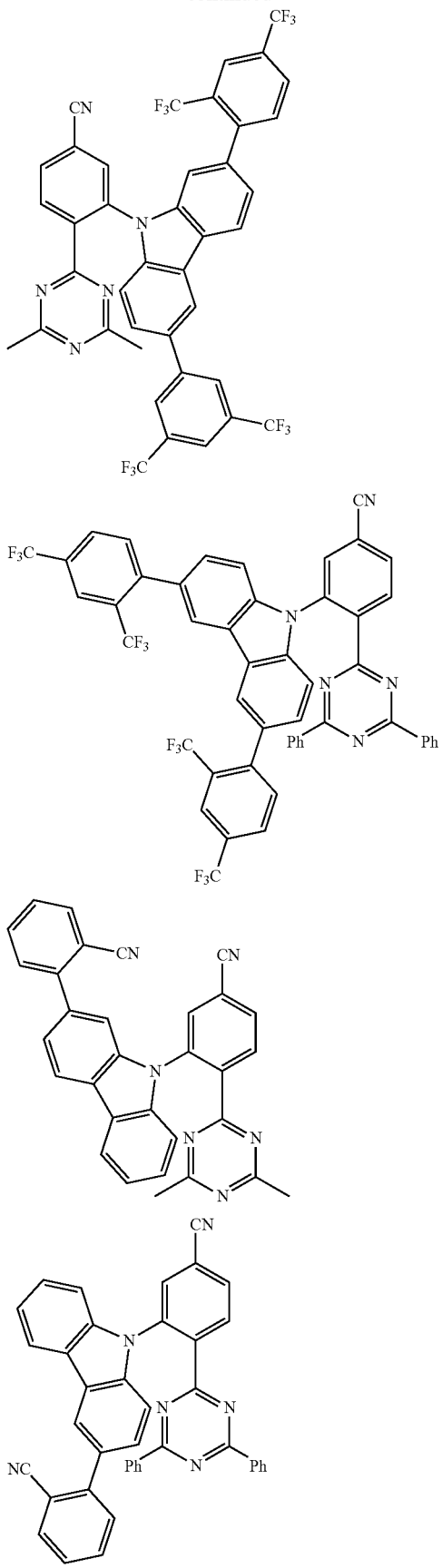
102
-continued
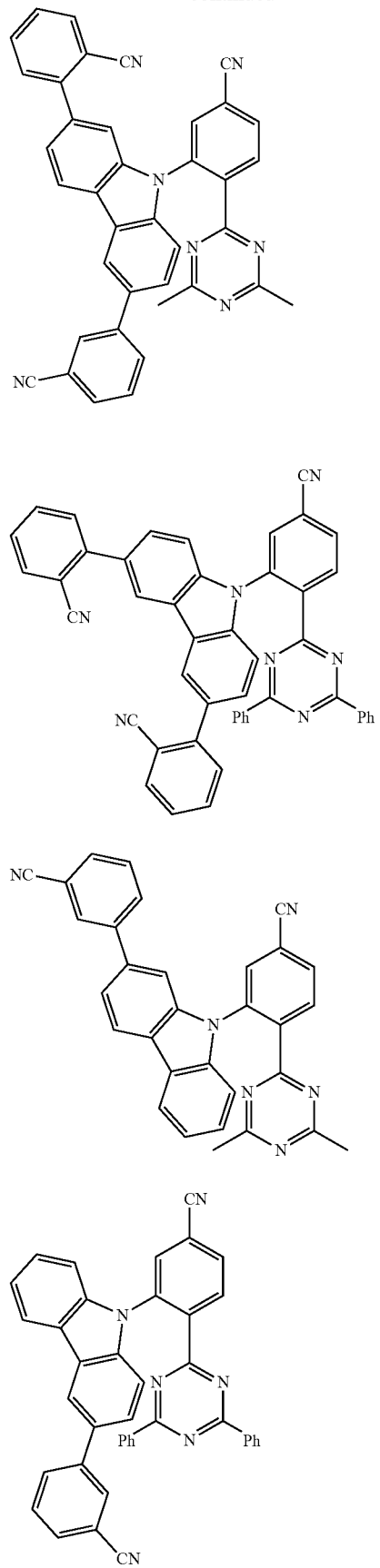

103
-continued
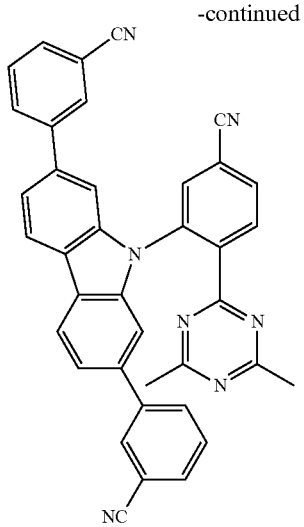
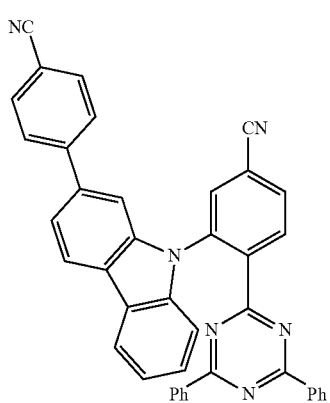
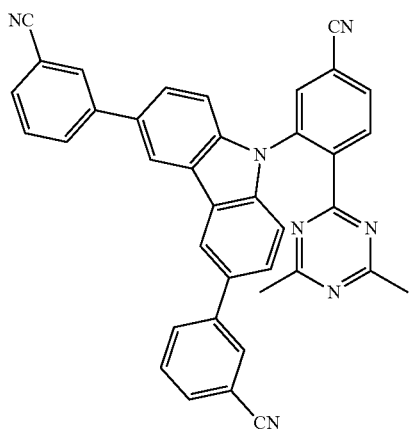
104
-continued
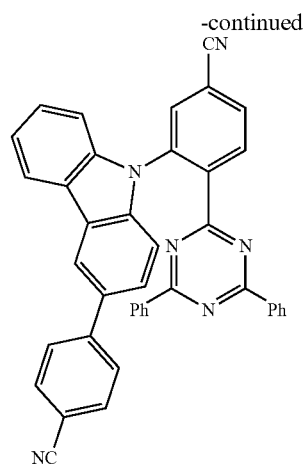
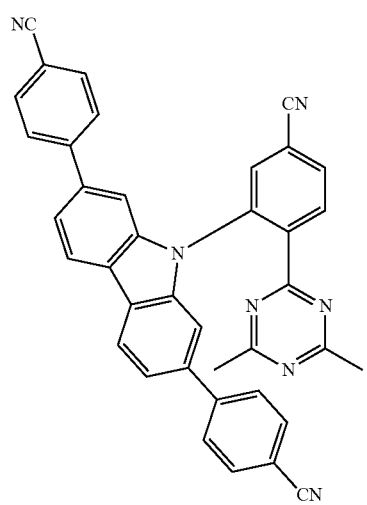
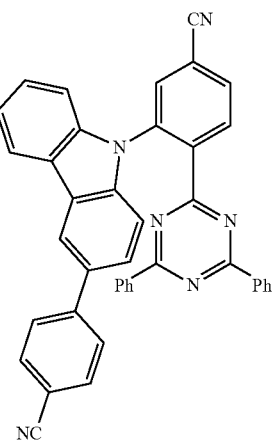

105
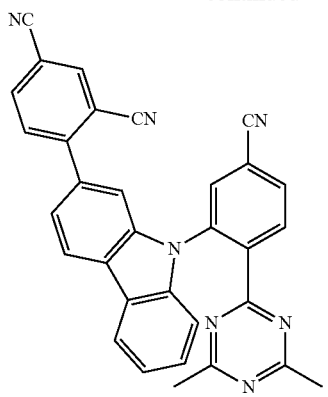
106
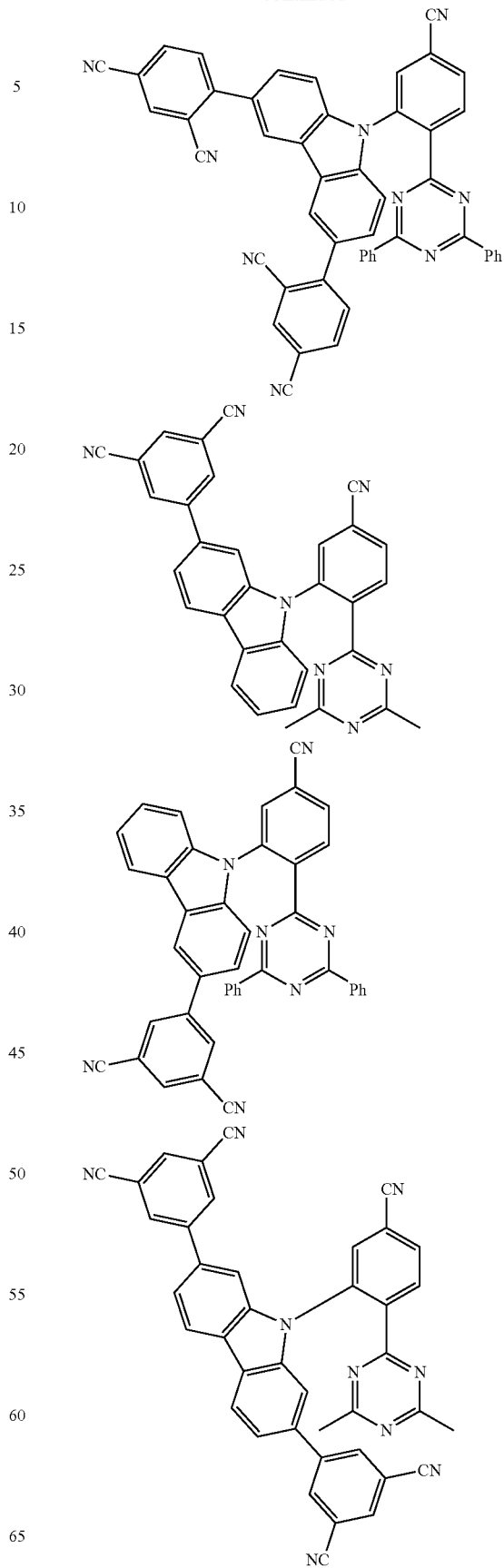

107
-continued
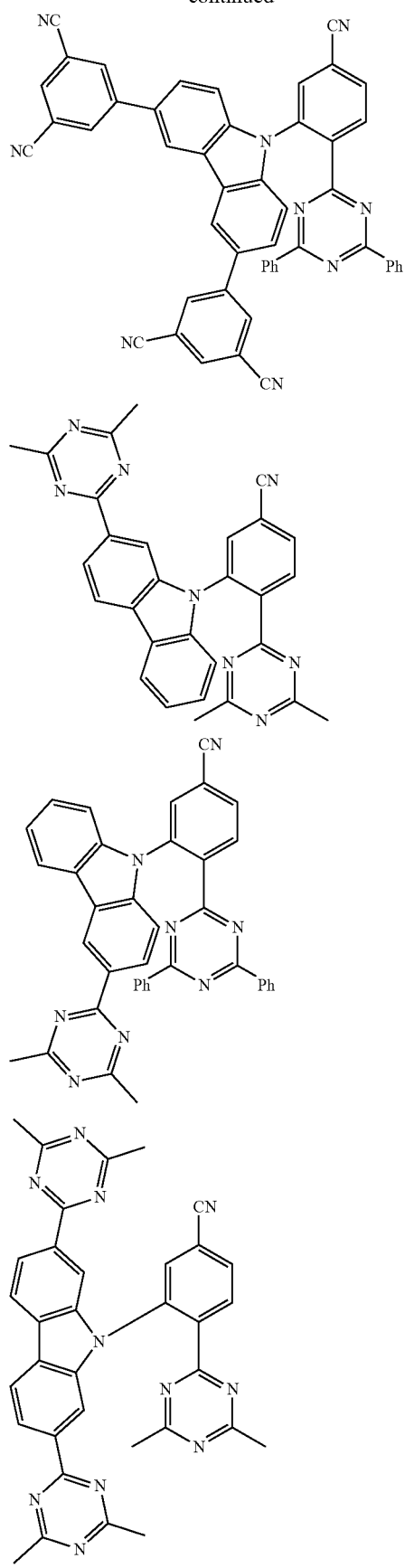
108
-continued
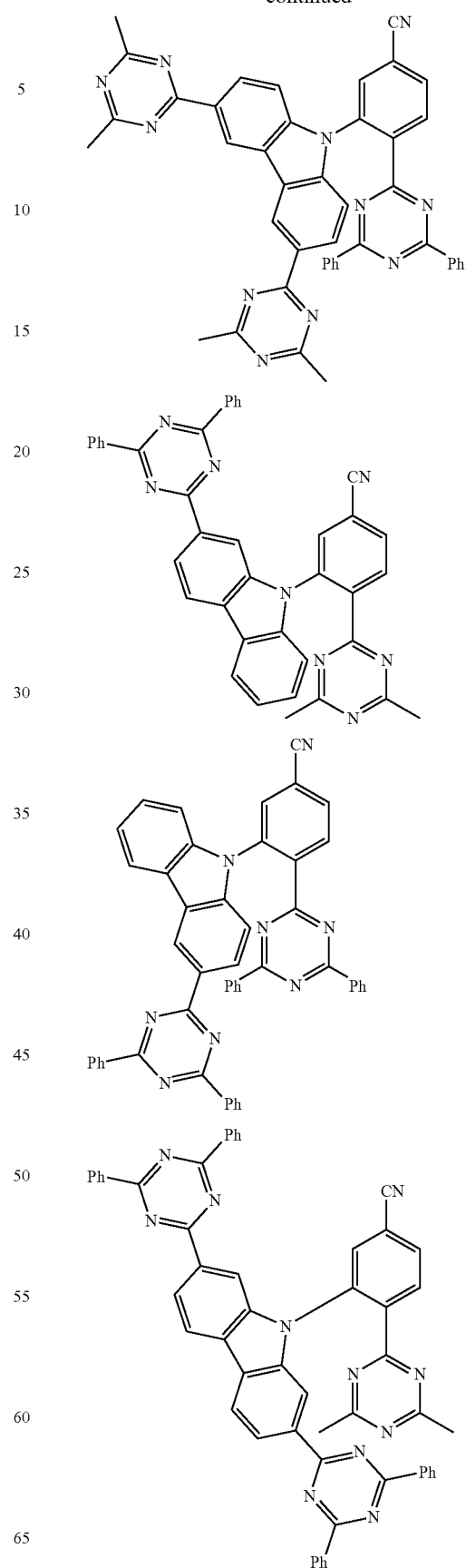

109
-continued
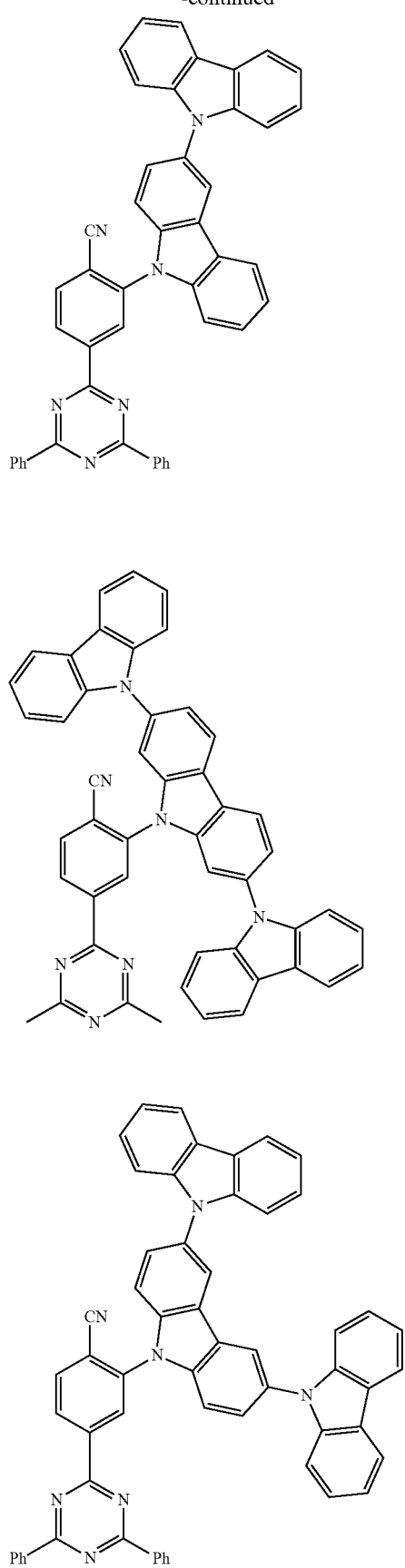
110
-continued
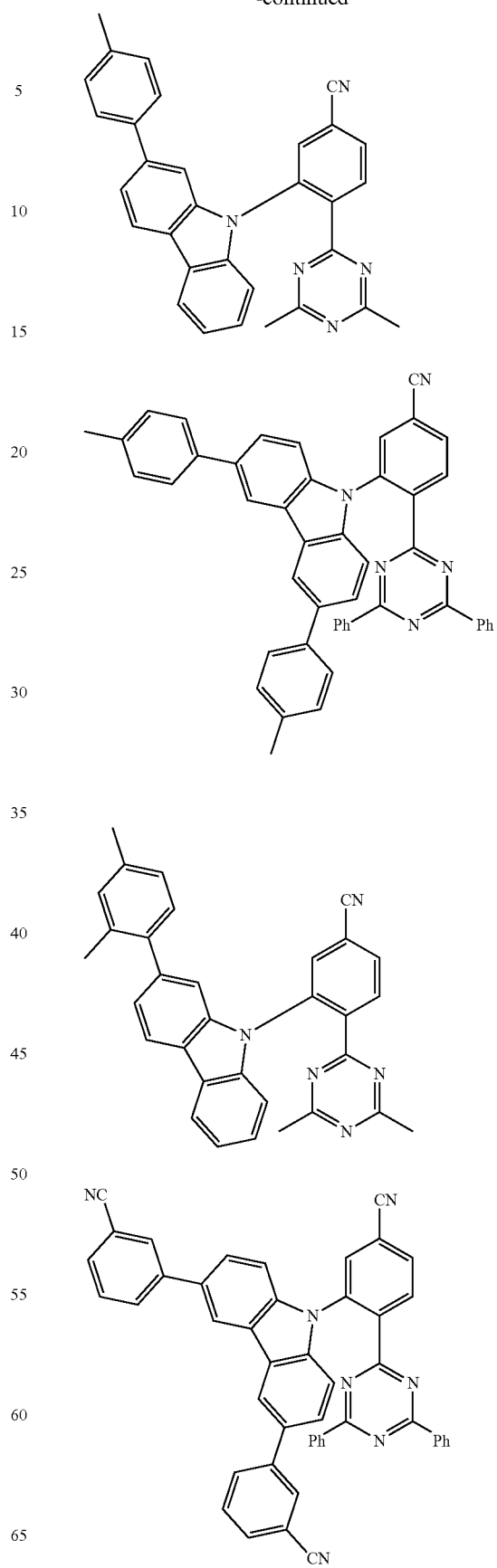

-continued
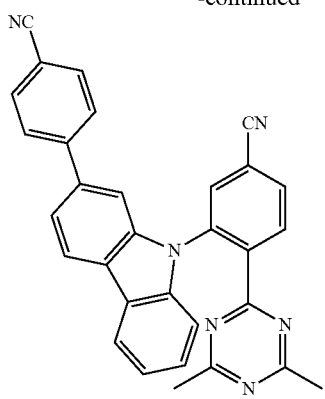
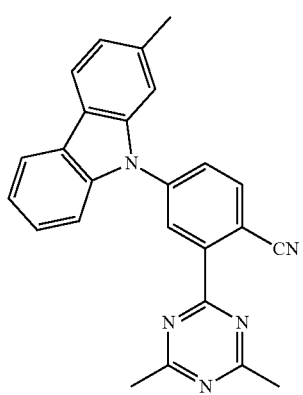
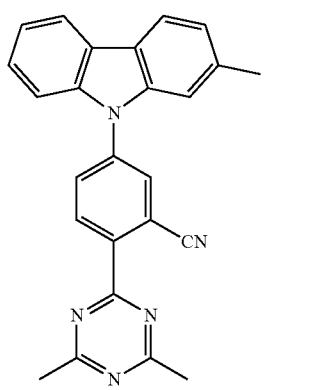
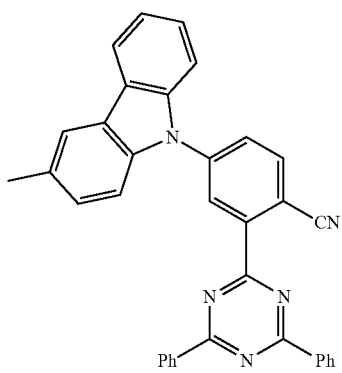
-continued
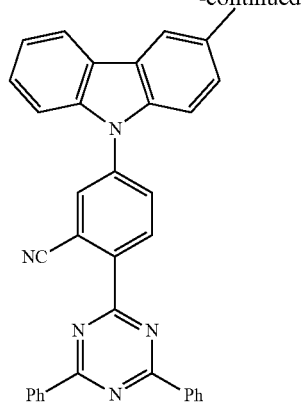
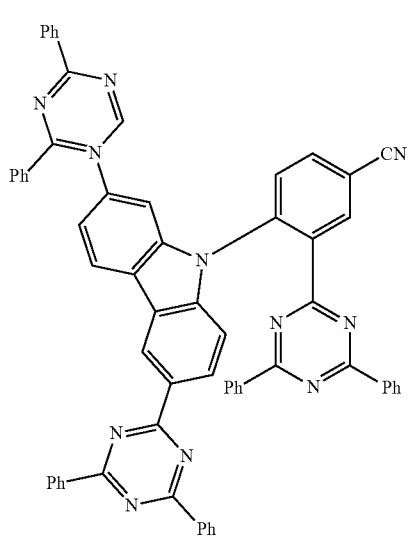
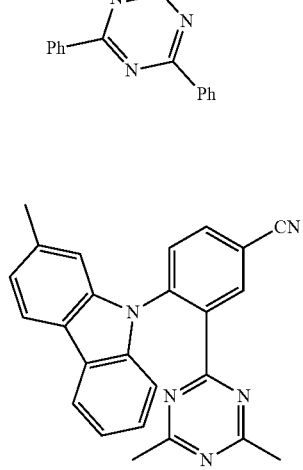
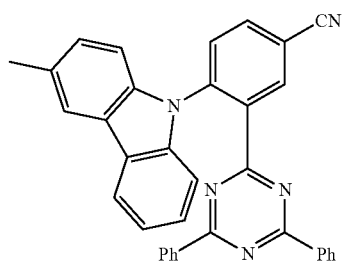

113
-continued
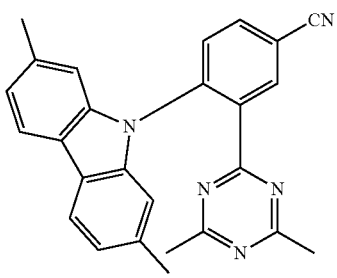
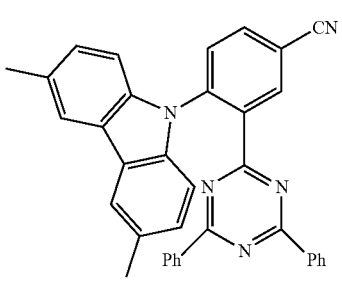
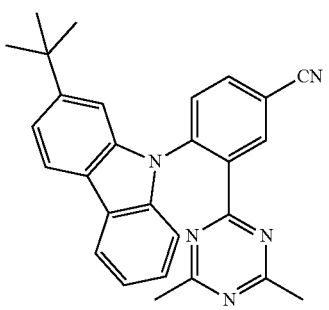
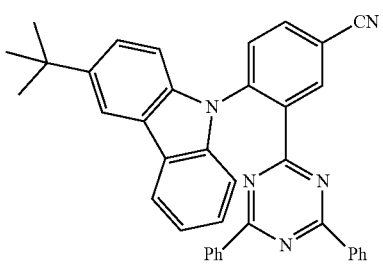
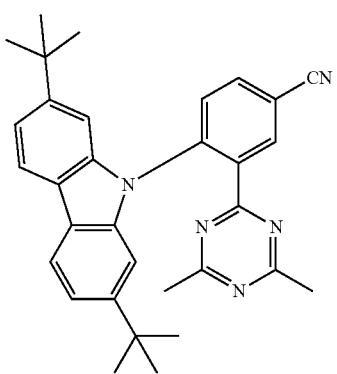
114
-continued
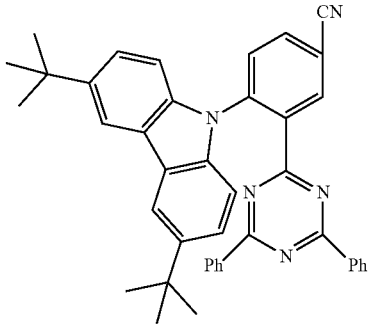
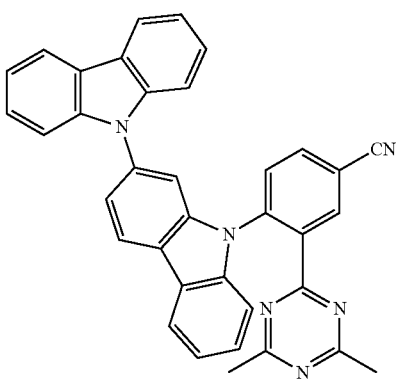
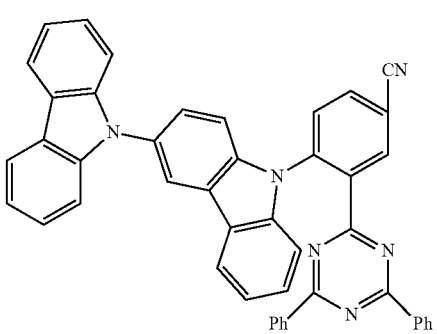
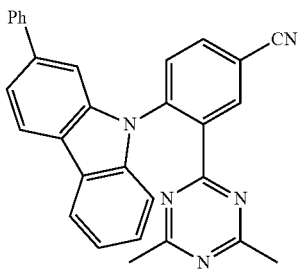

115
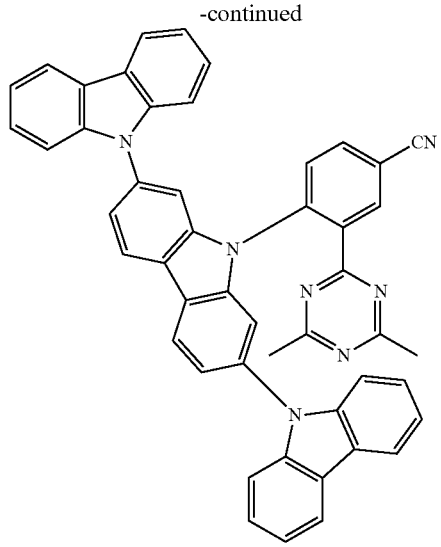
116
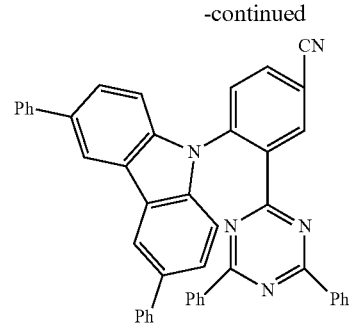
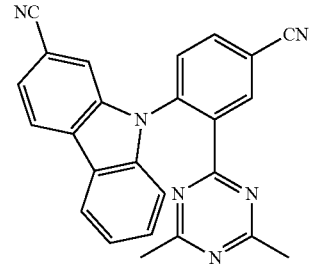
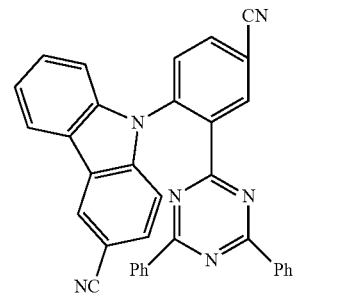
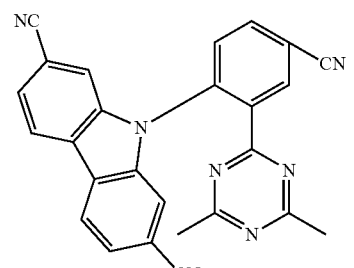
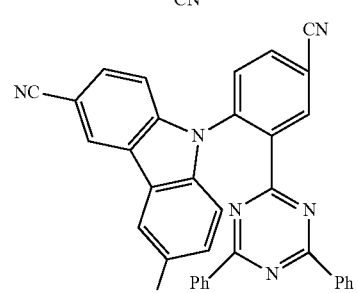
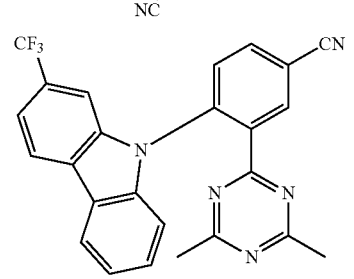

117
-continued
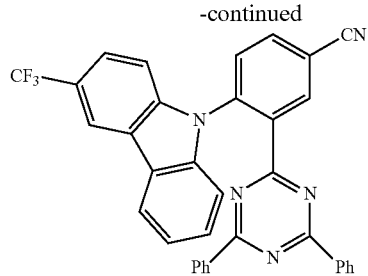
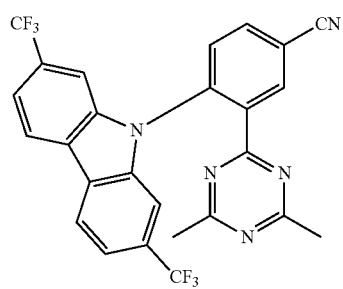
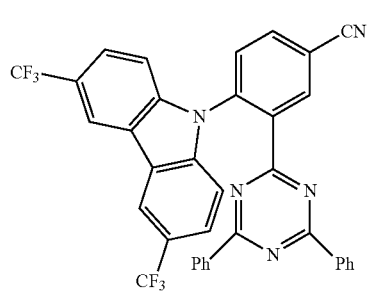
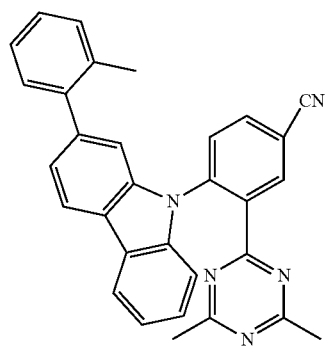
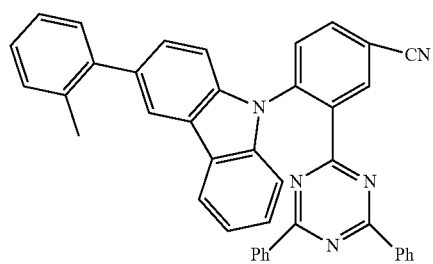
118
-continued
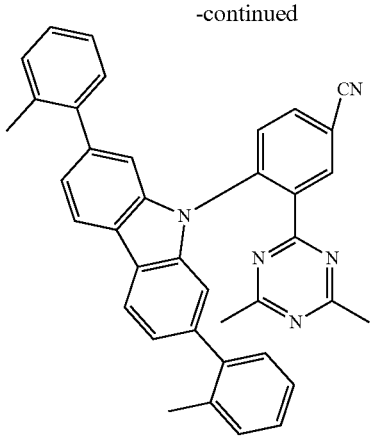
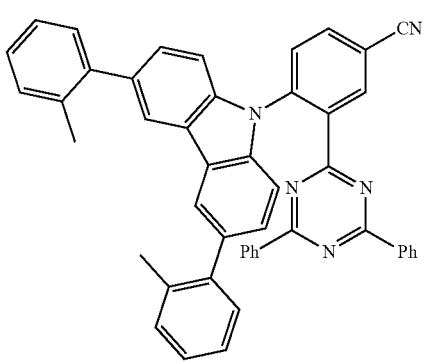
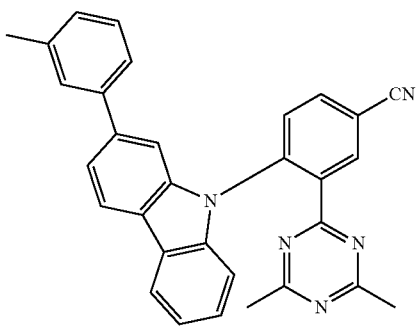
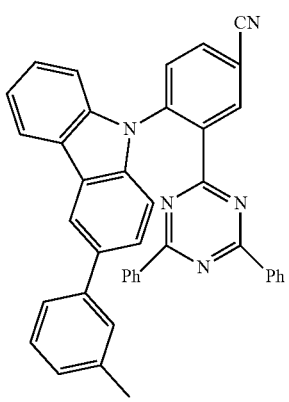

119
-continued
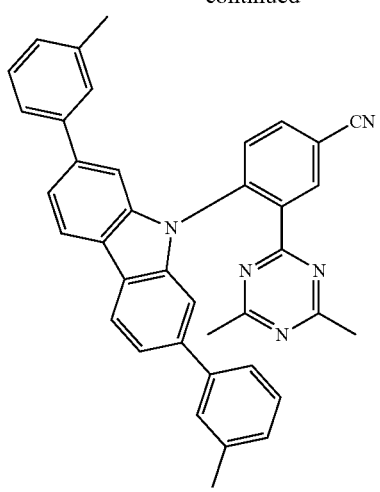
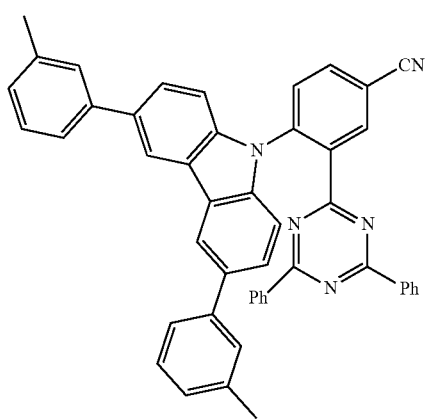
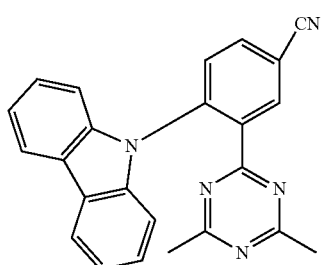
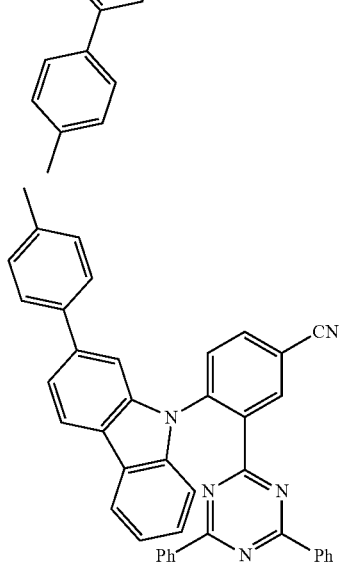
120
-continued
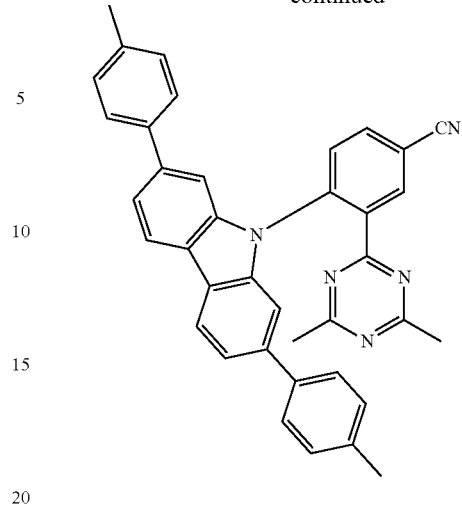
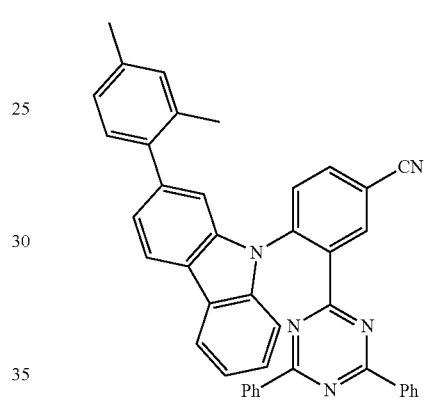
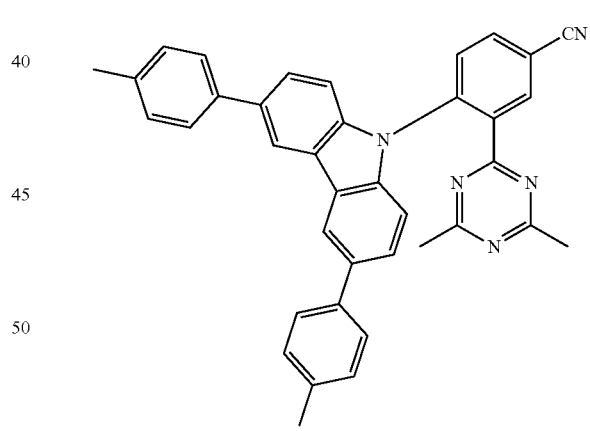
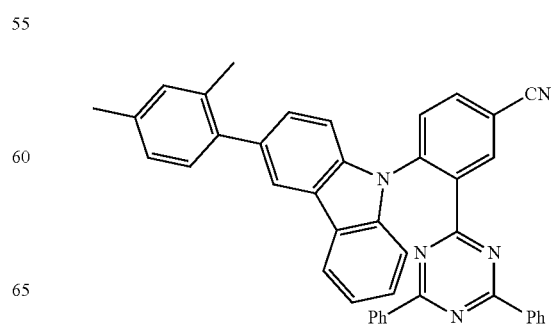

121
-continued
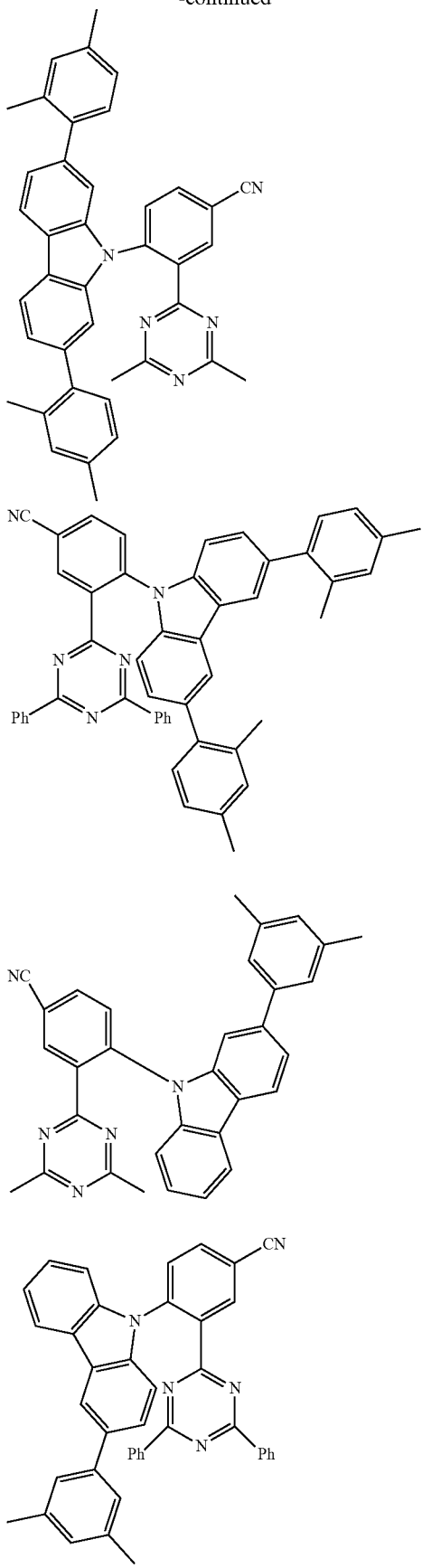
122
-continued
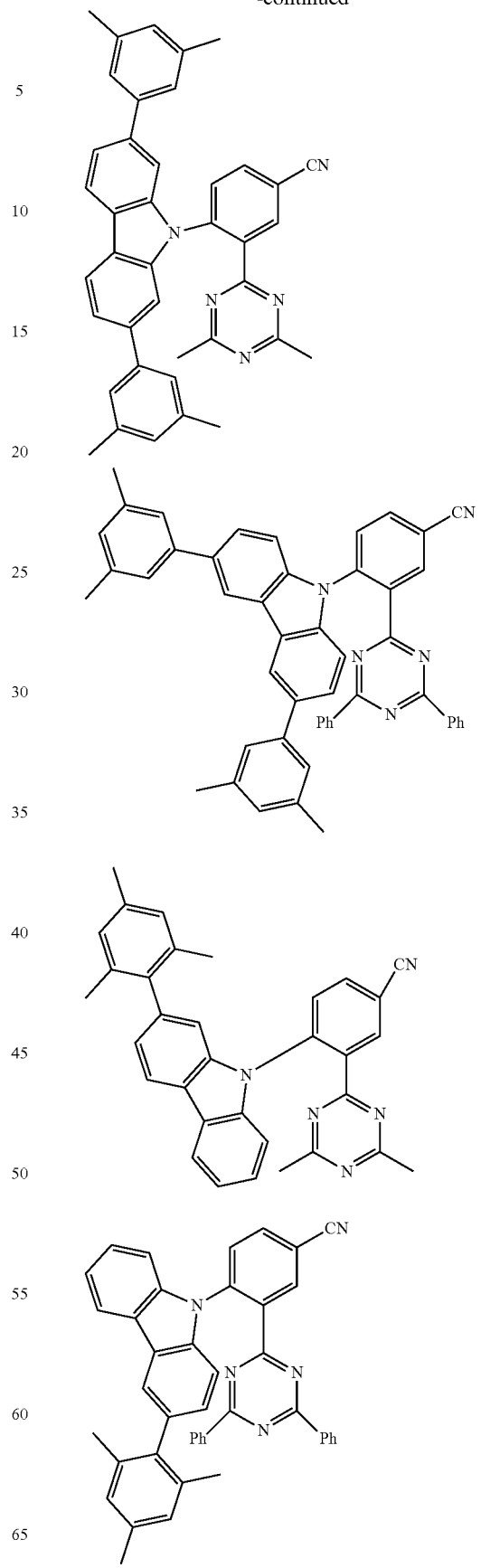

-continued
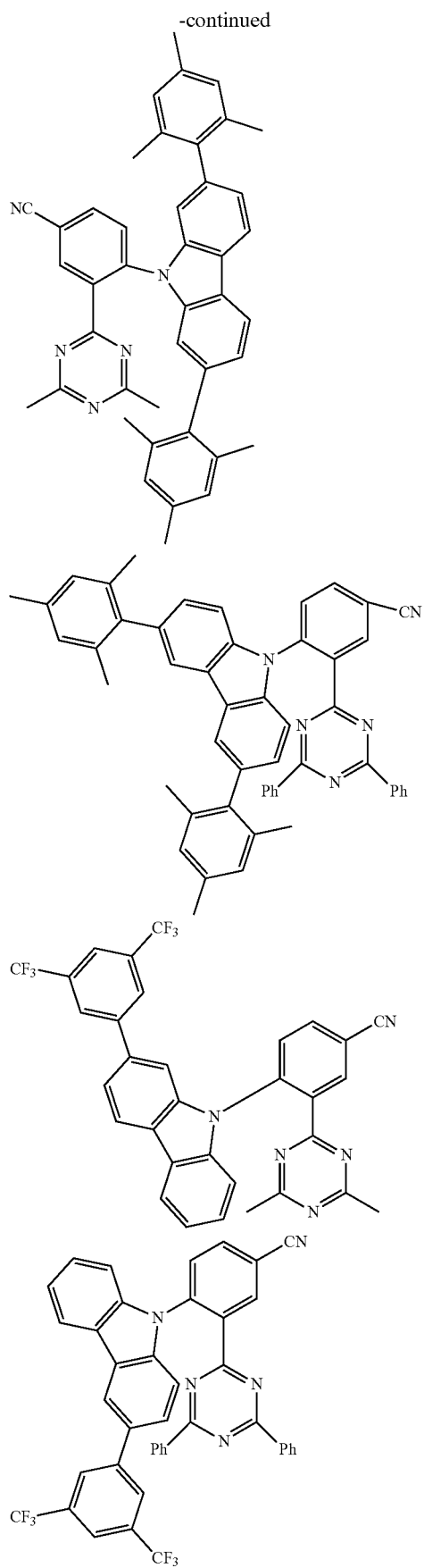
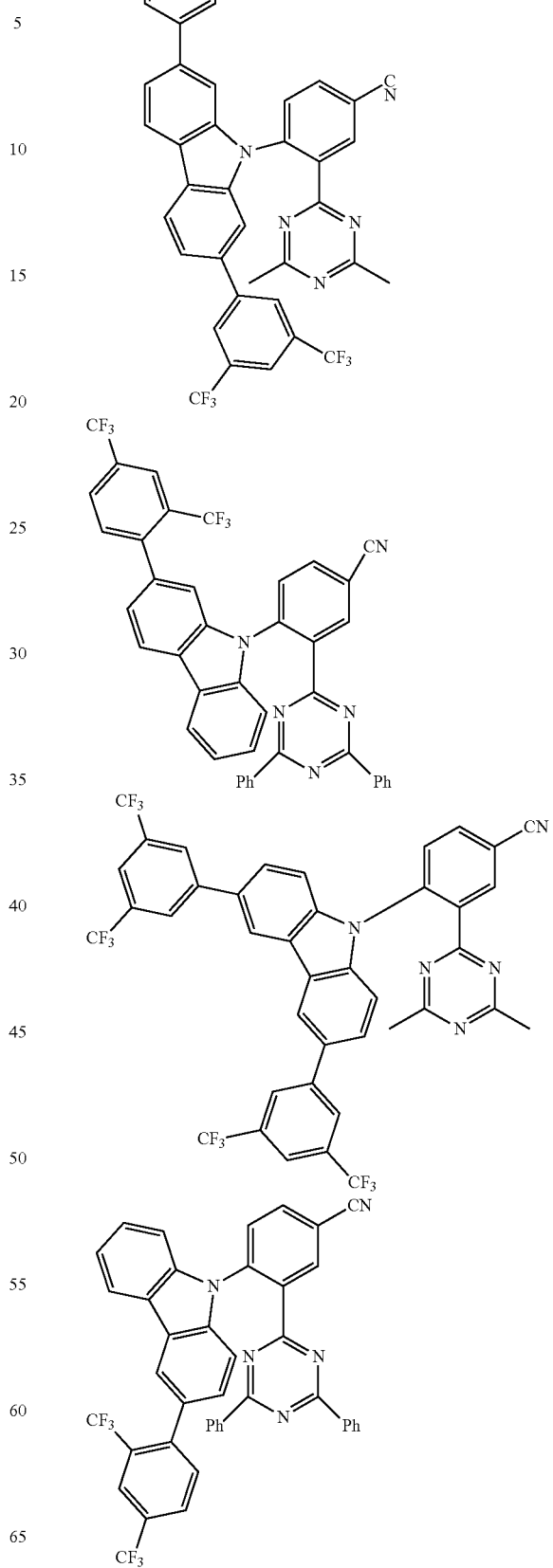

125
-continued
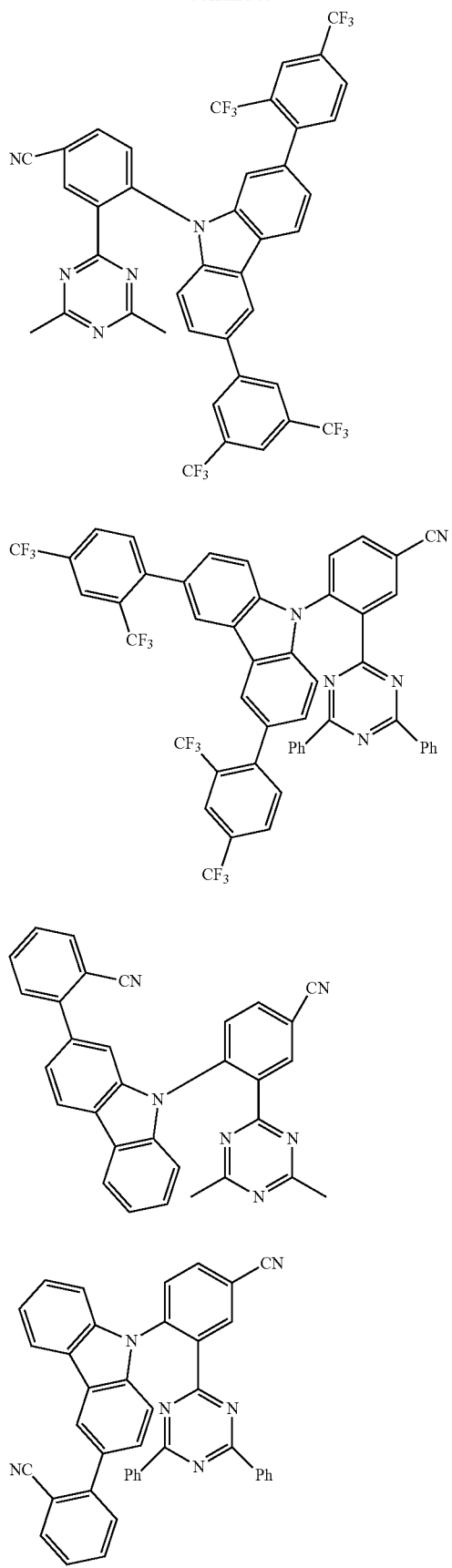
126
-continued
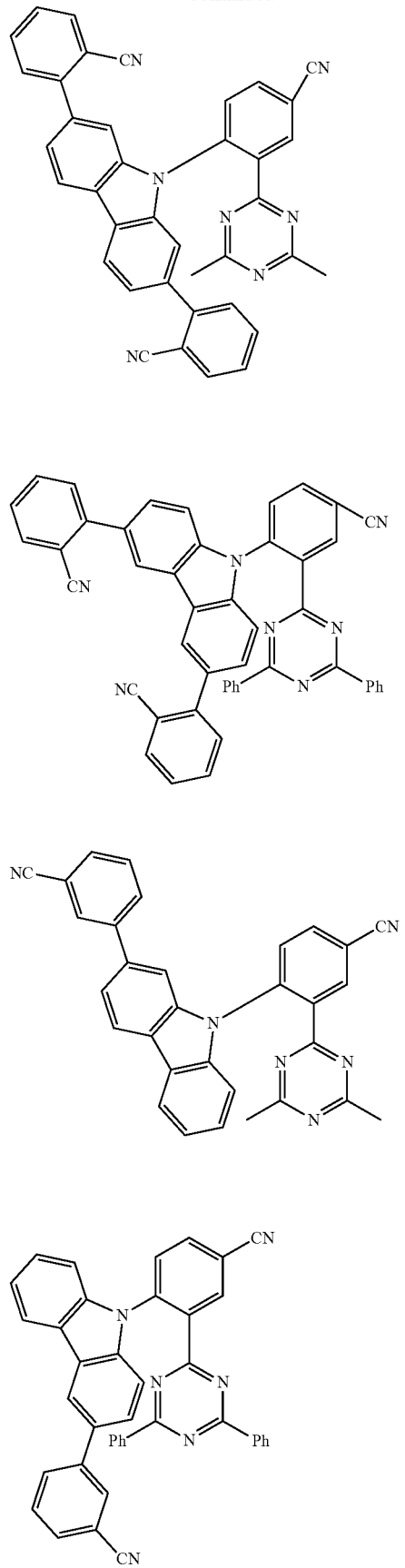

127
-continued
128
-continued
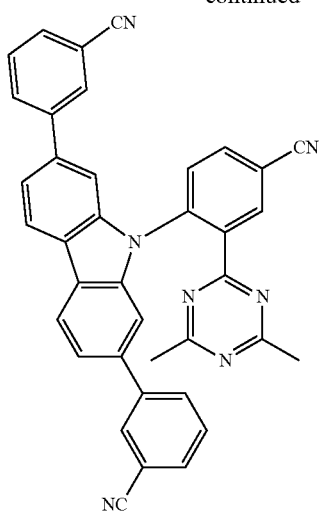
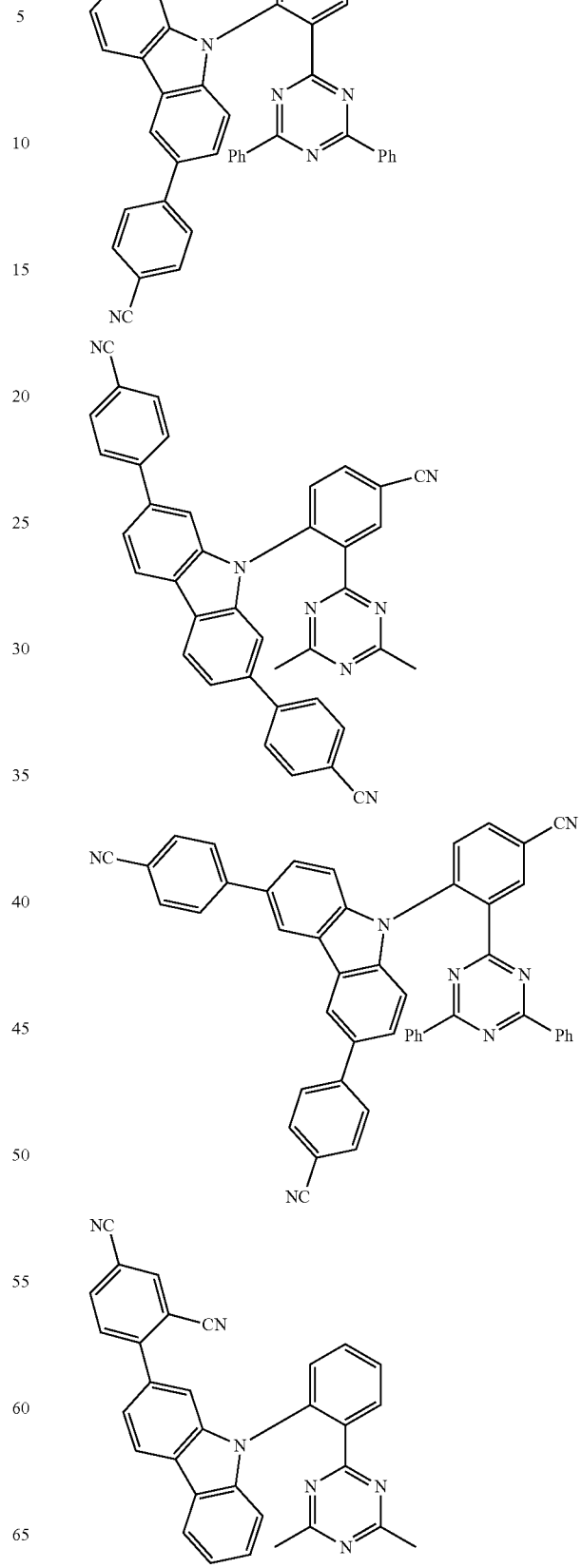

129
-continued
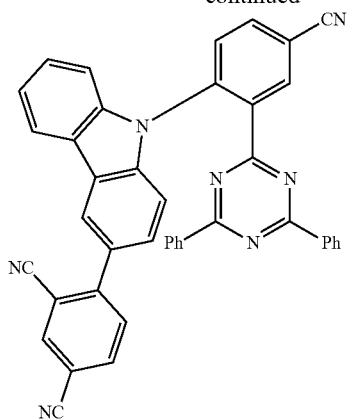
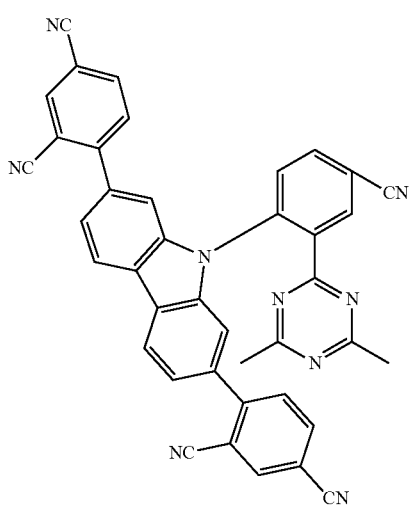
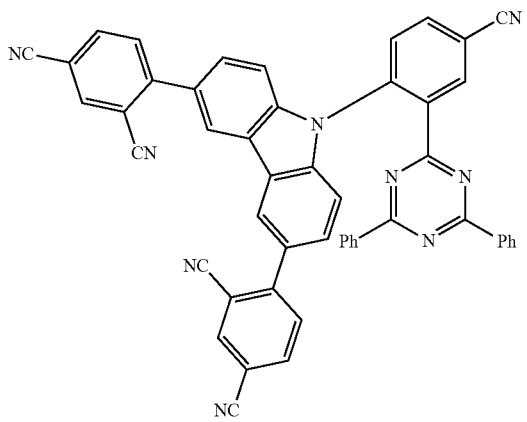
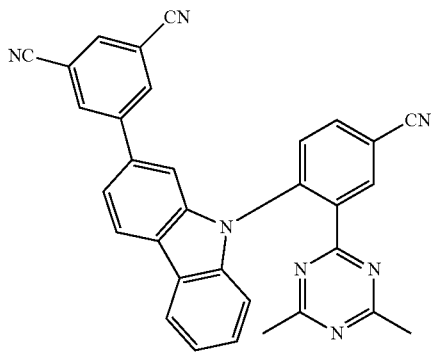
130
-continued
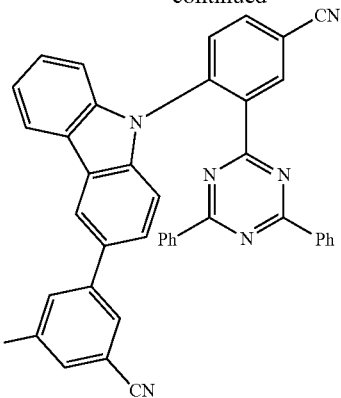
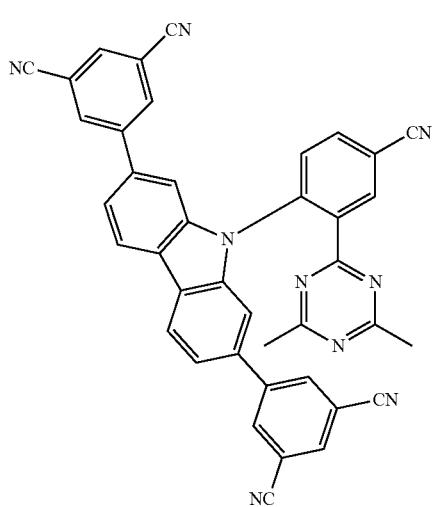
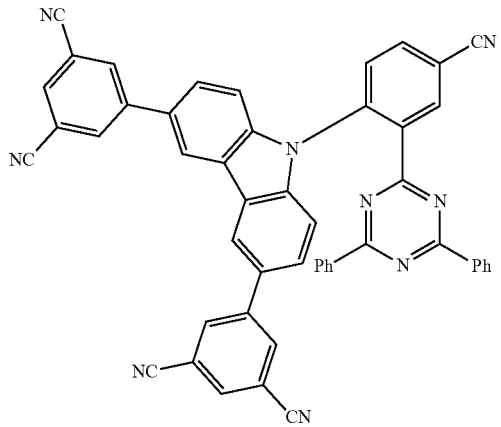
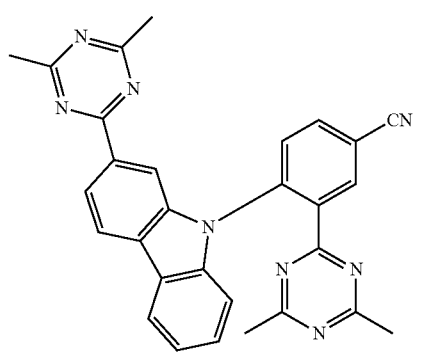

131
-continued
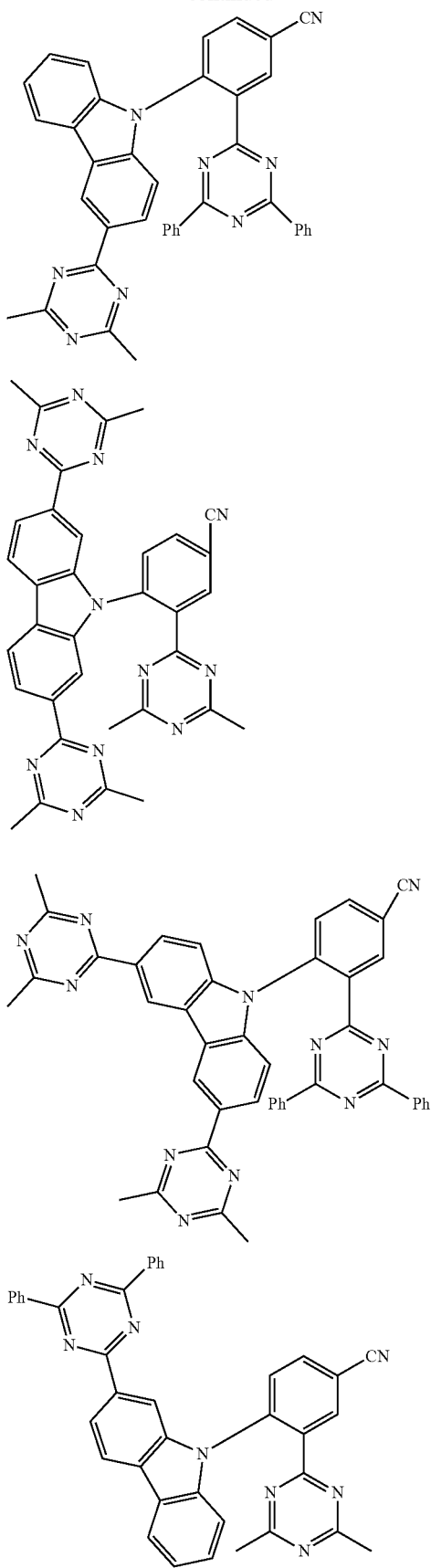
132
-continued
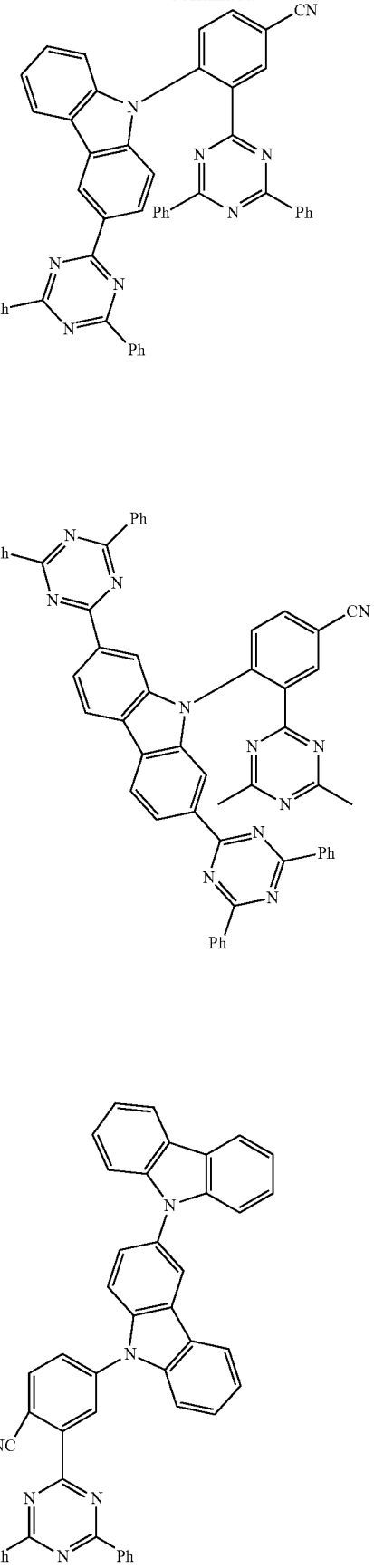

133
-continued
134
-continued
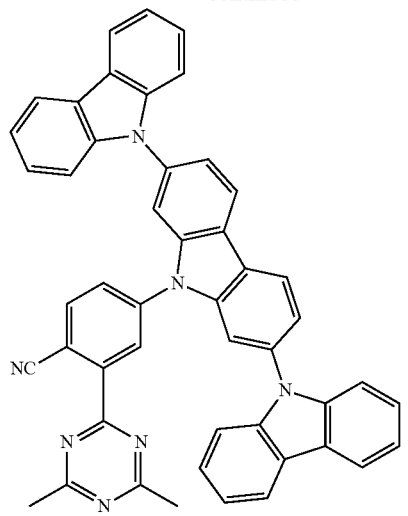
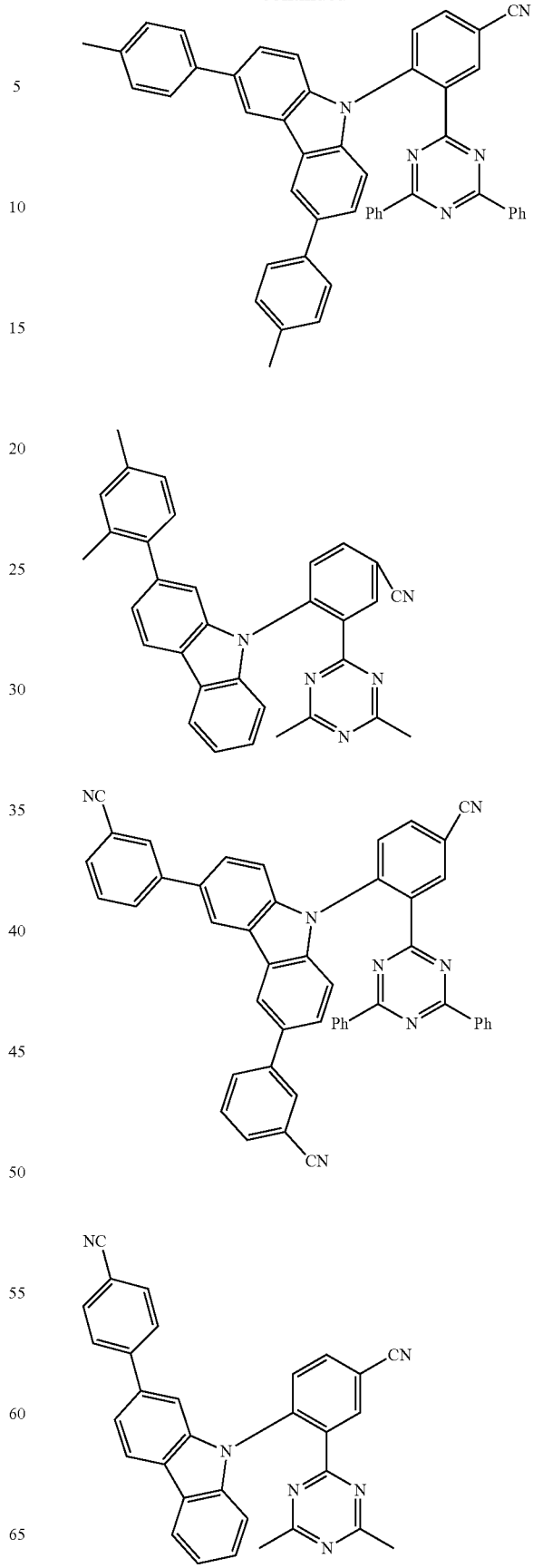

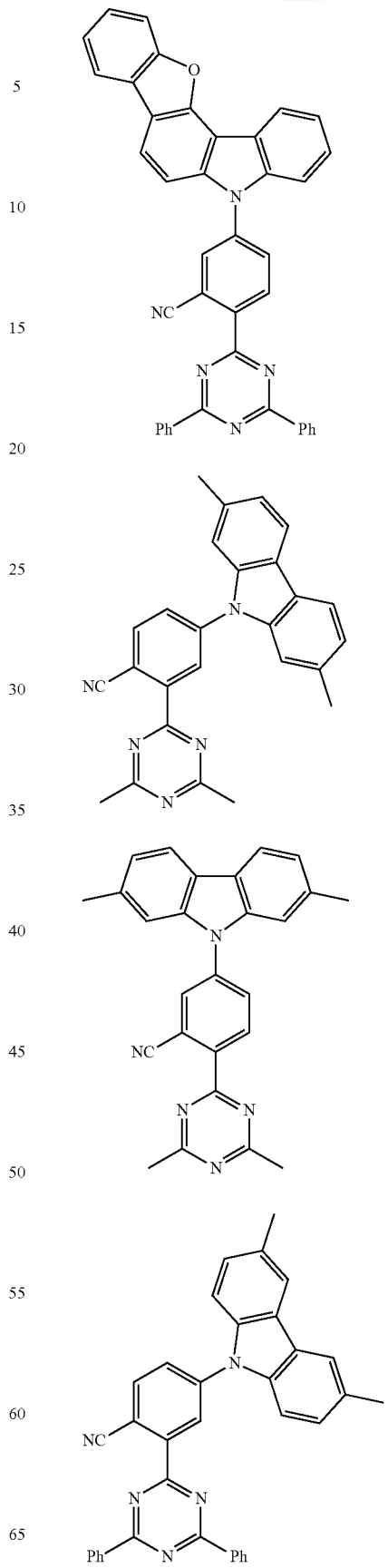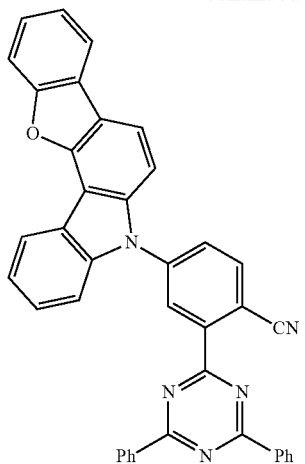

137 138
-continued -continued
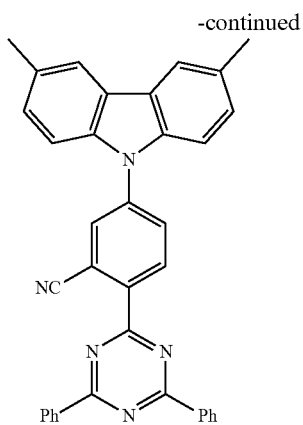
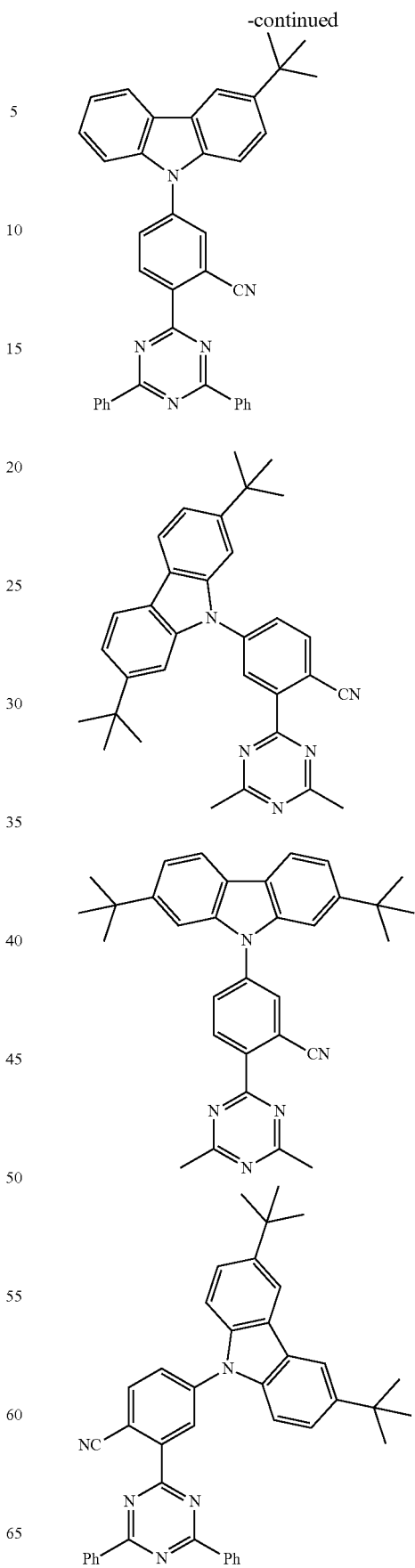

139
-continued
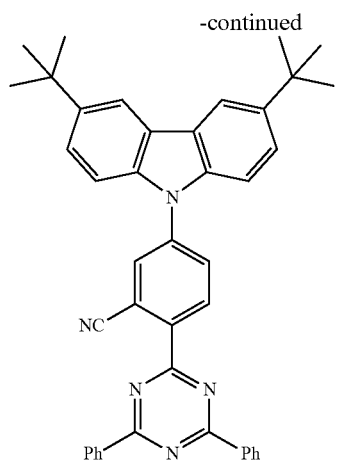
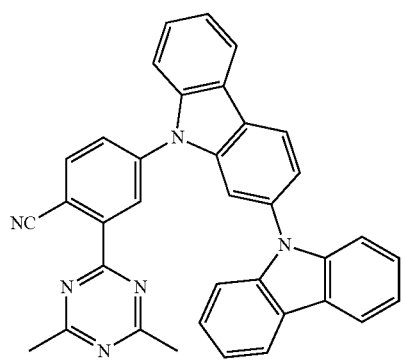
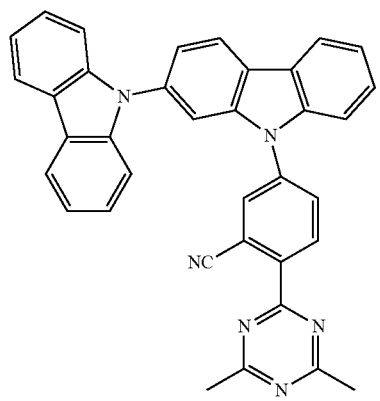
140
-continued
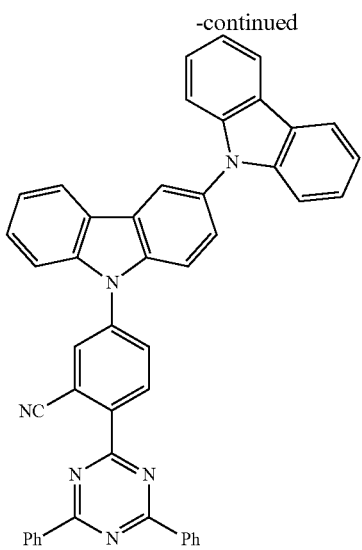
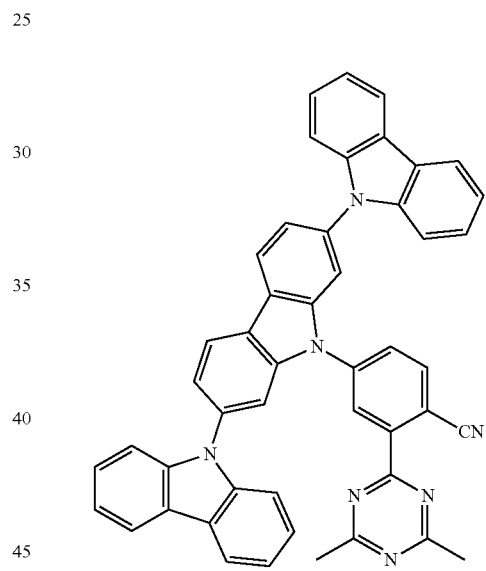
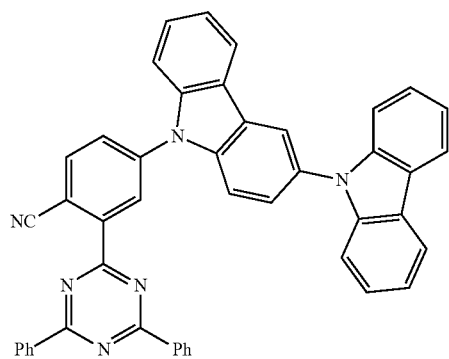
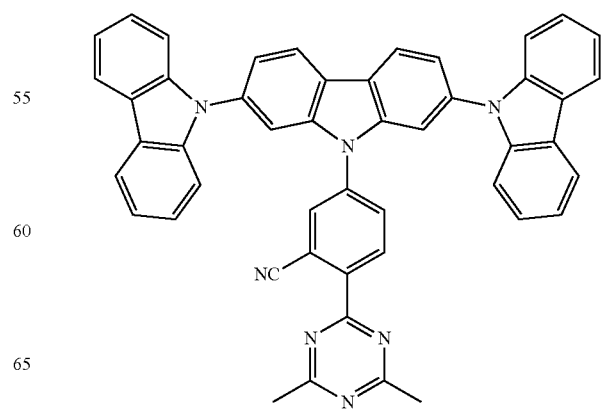

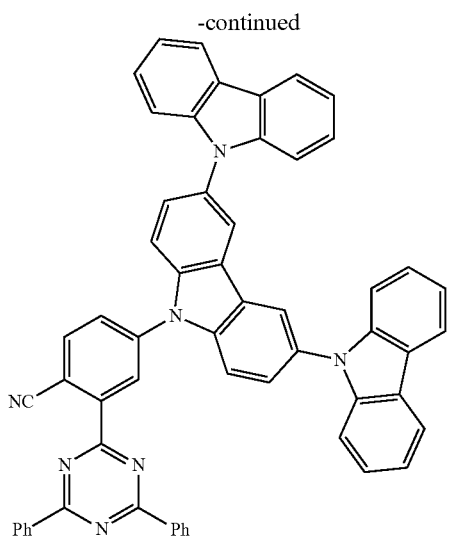
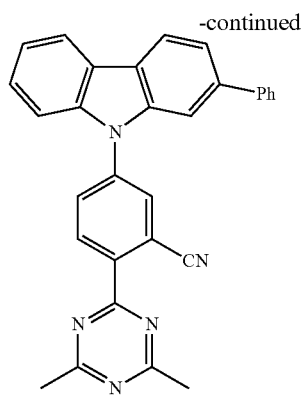
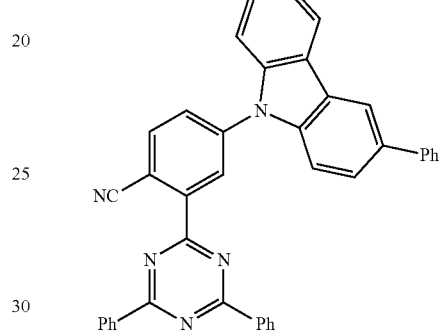
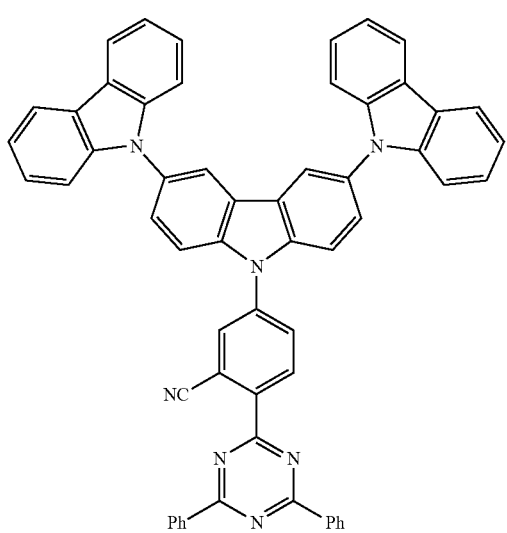
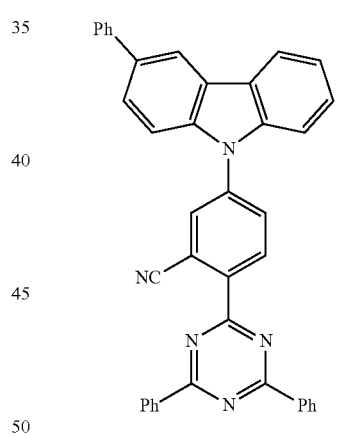
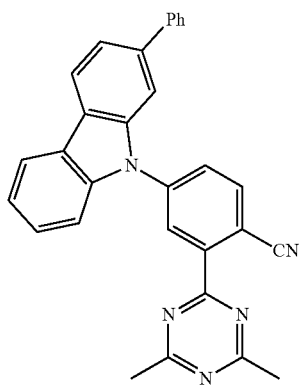
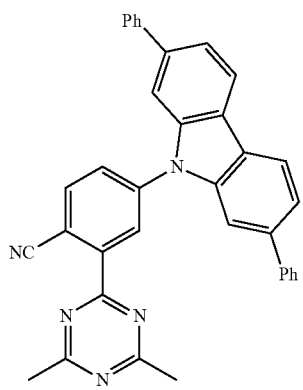

-continued
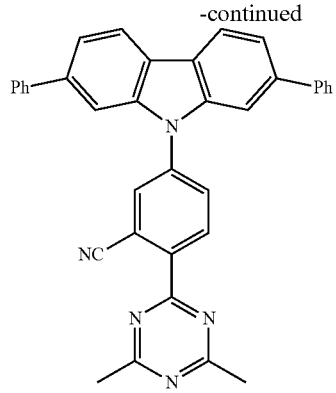
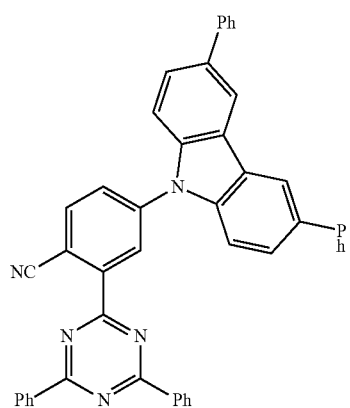
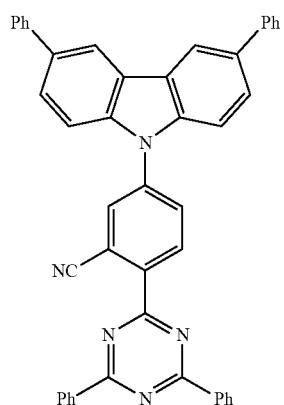
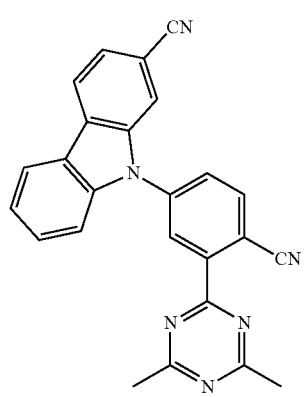
-continued
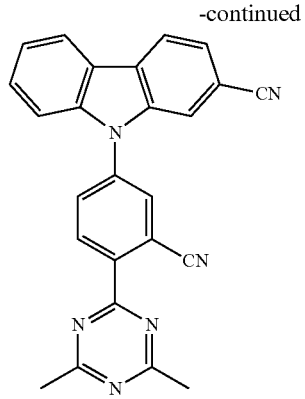
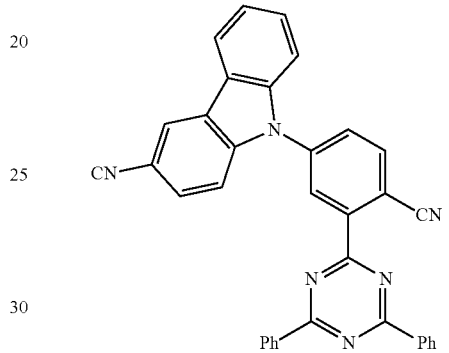
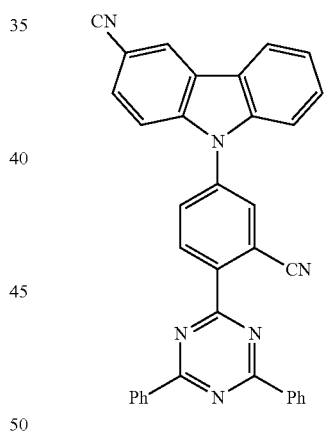
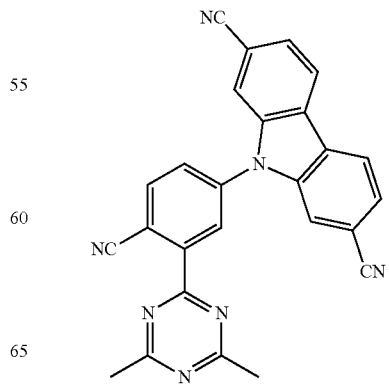

145
-continued
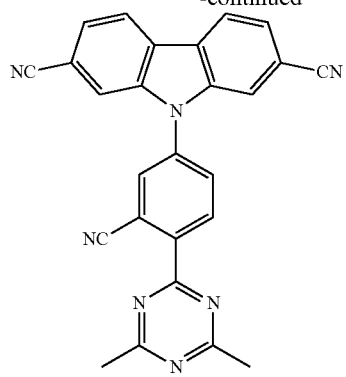
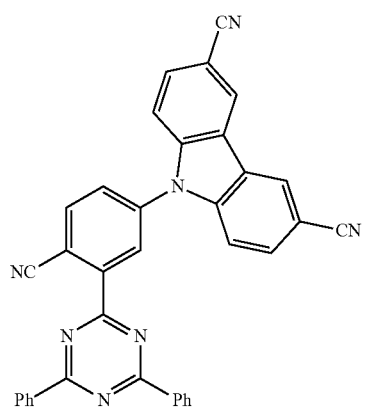
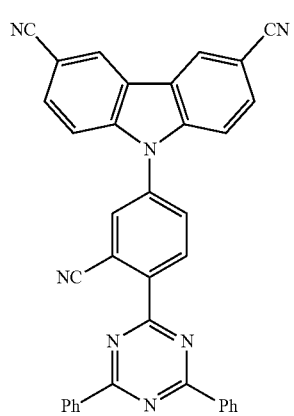
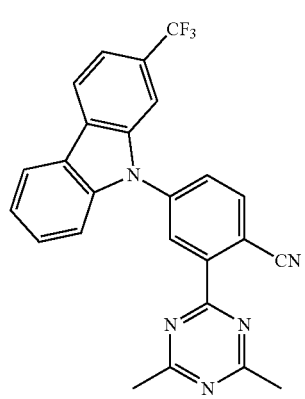
146
-continued
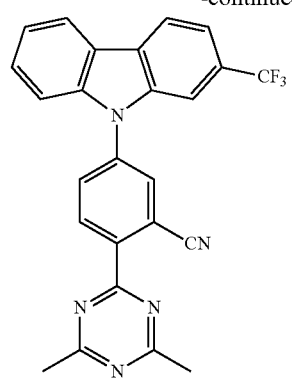
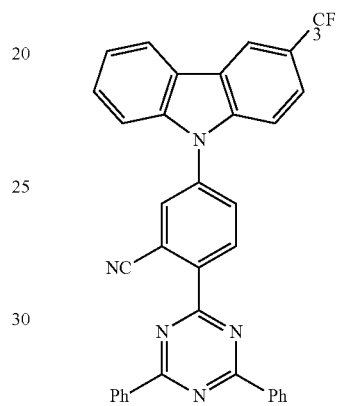
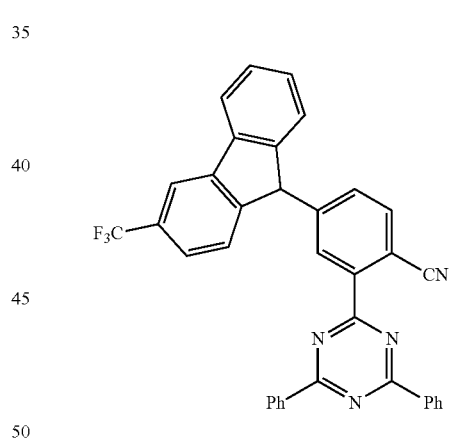
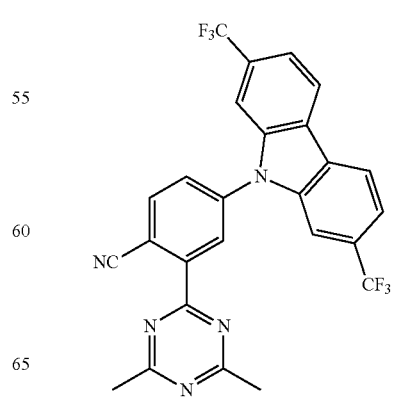

147
-continued
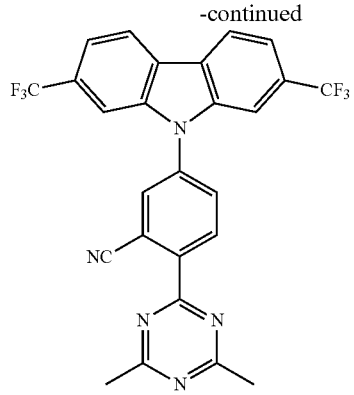
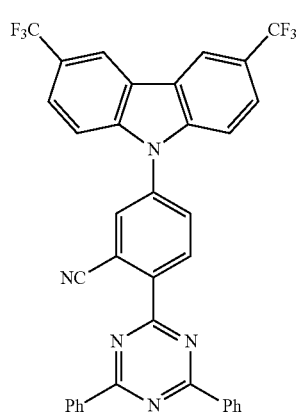
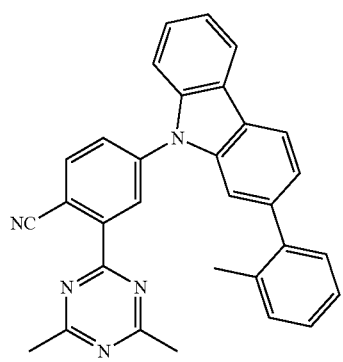
148
-continued
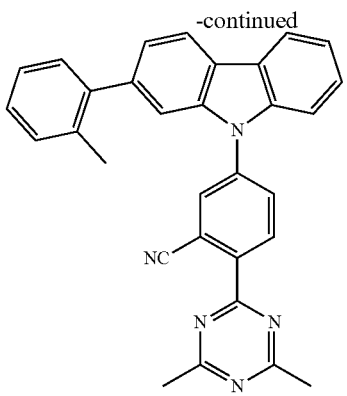
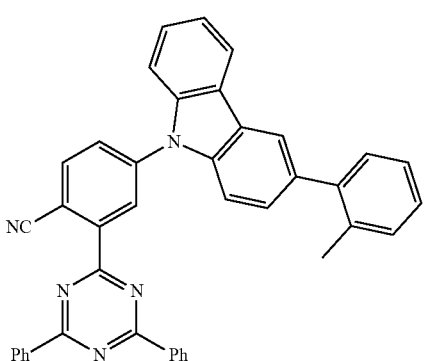
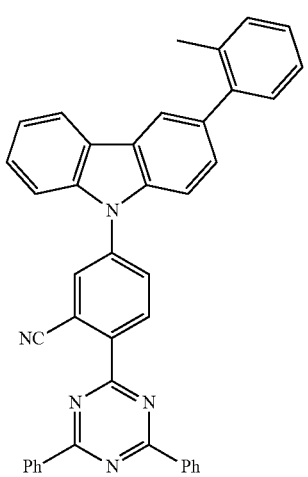
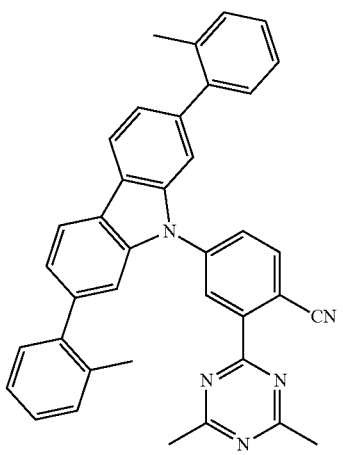

149
-continued
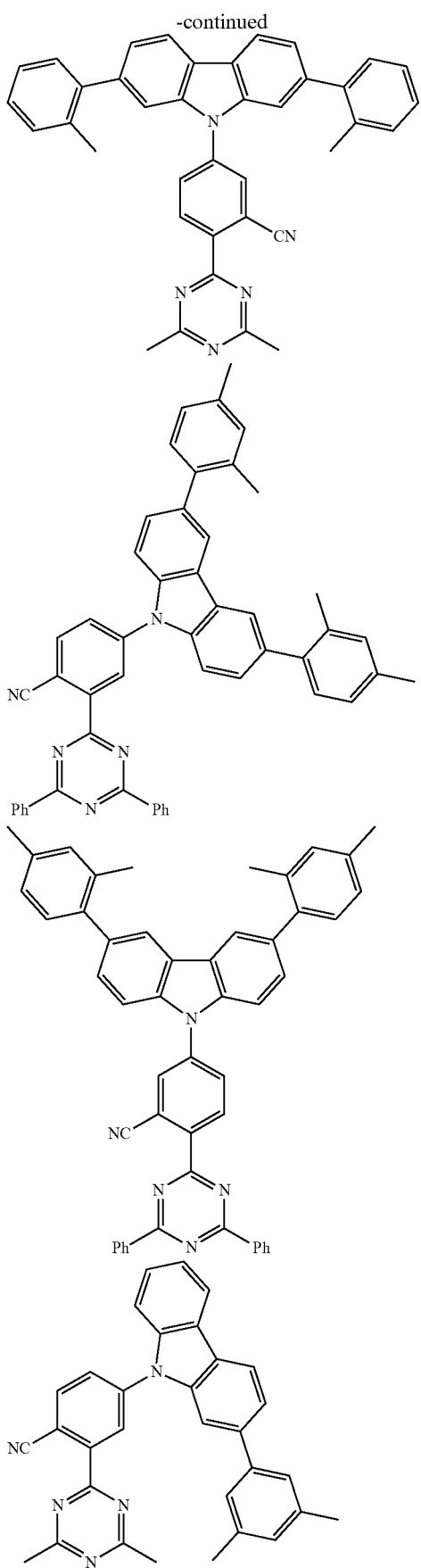
150
-continued
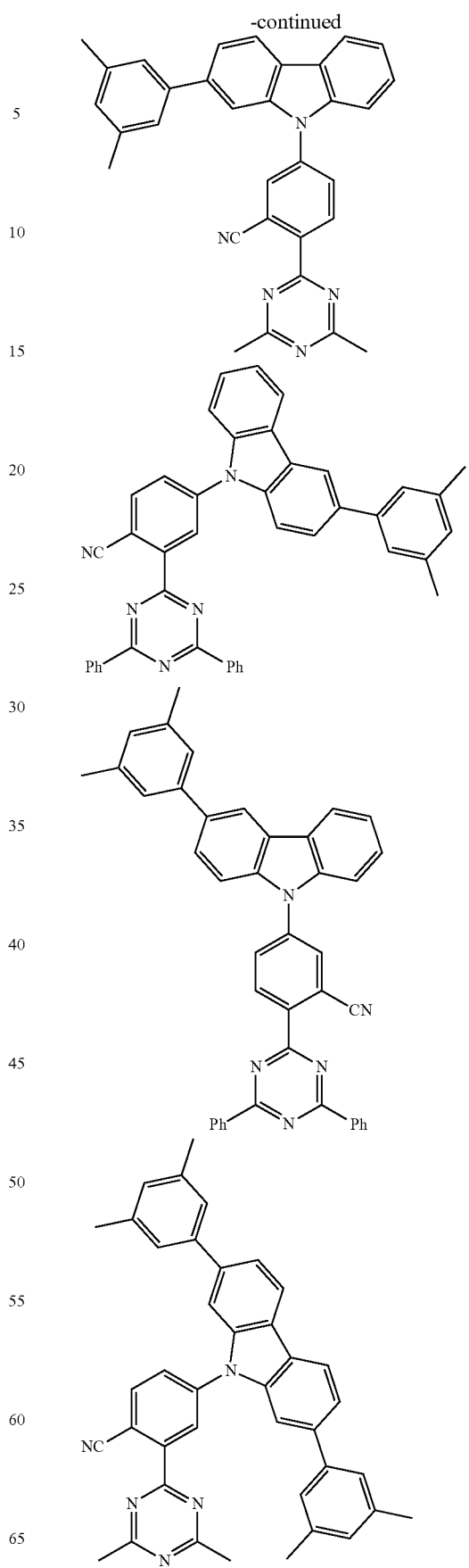

151
-continued
152
-continued
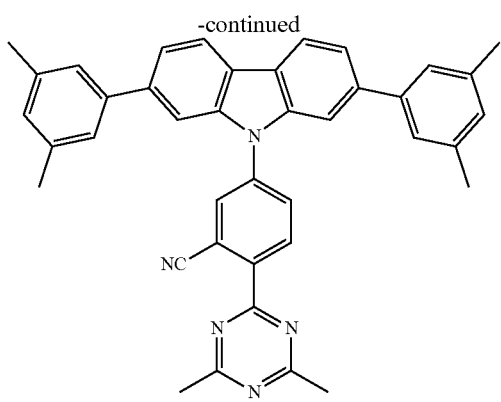
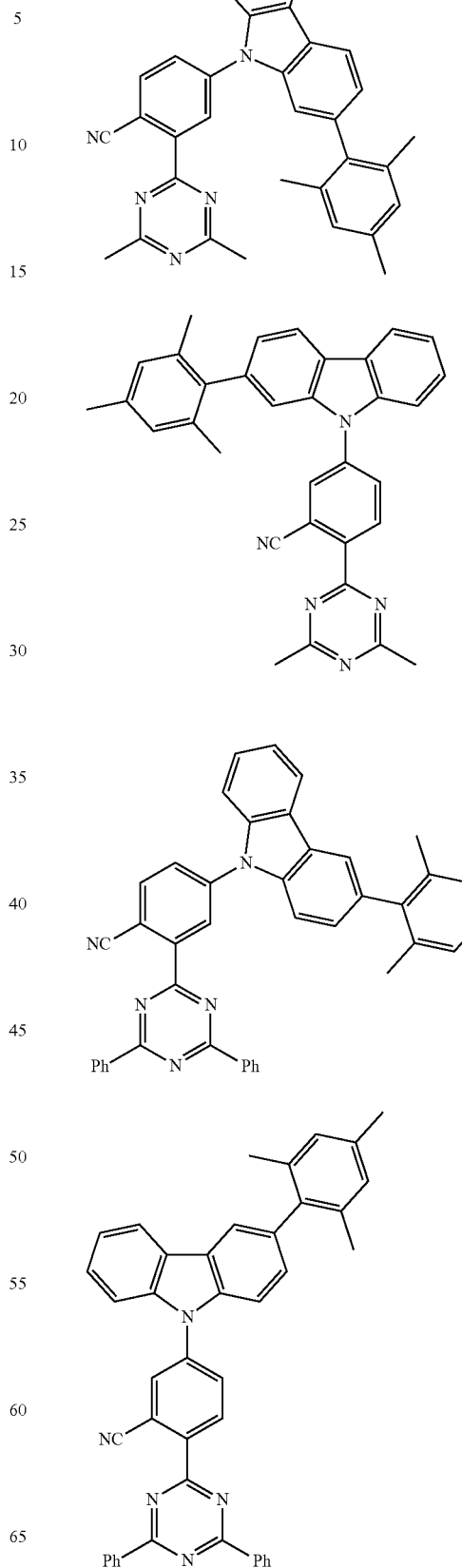

153
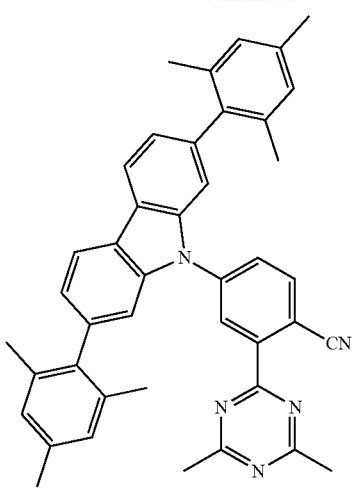
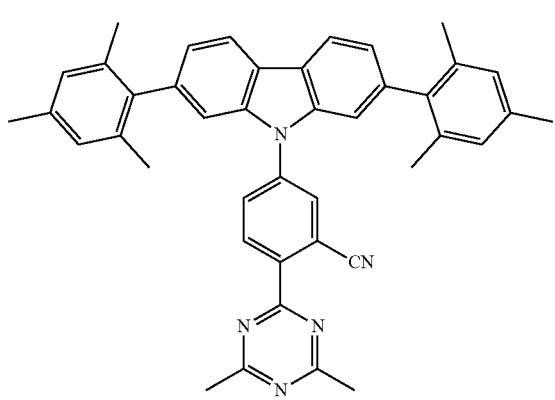
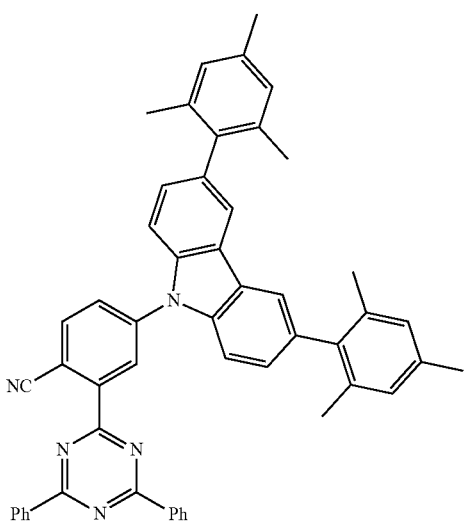
154
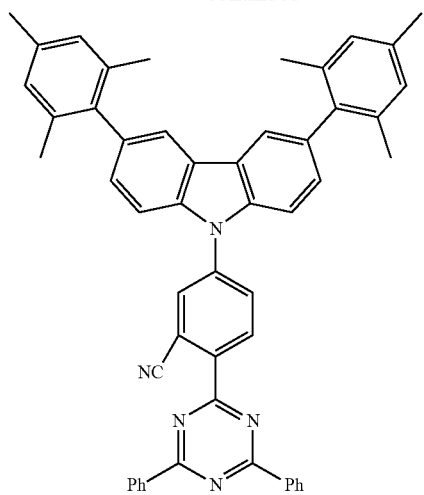
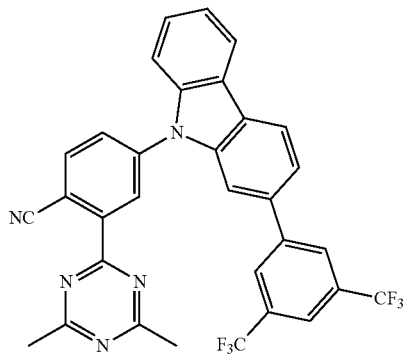
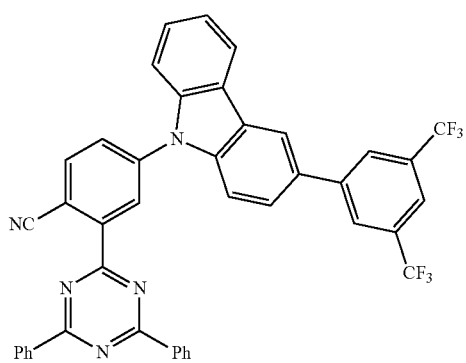

-continued
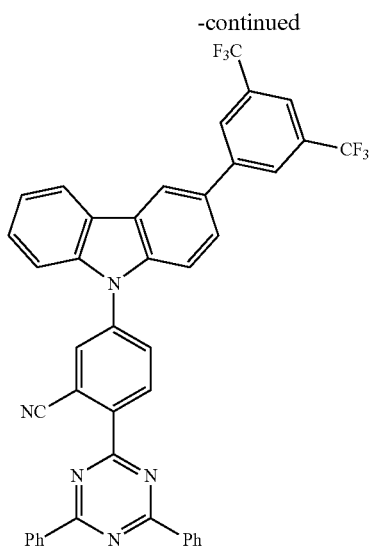
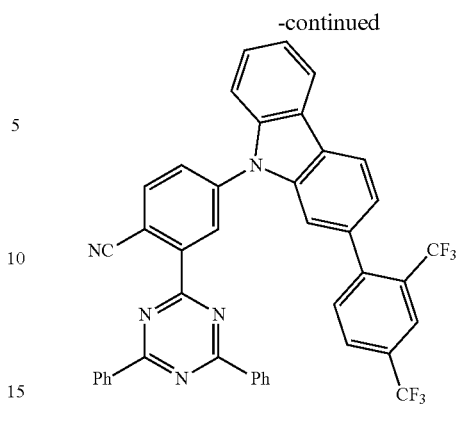
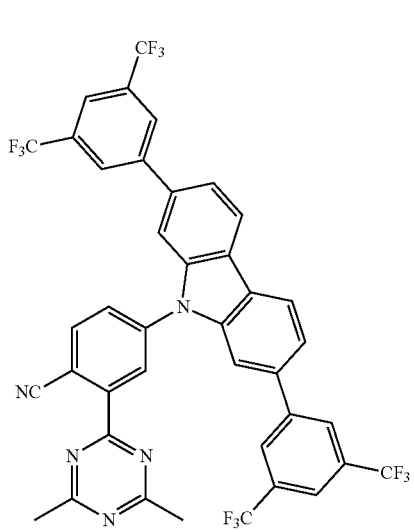
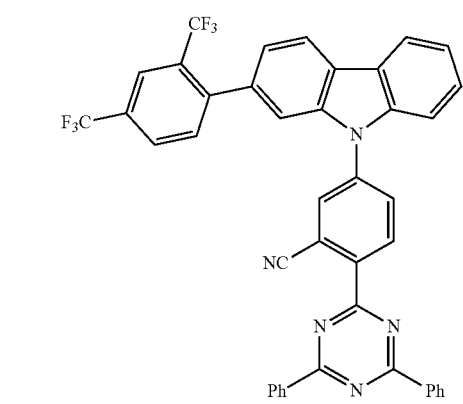
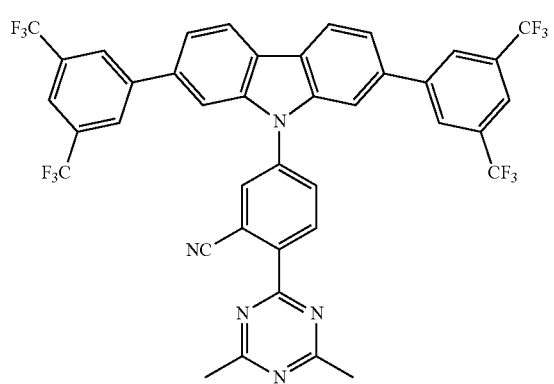
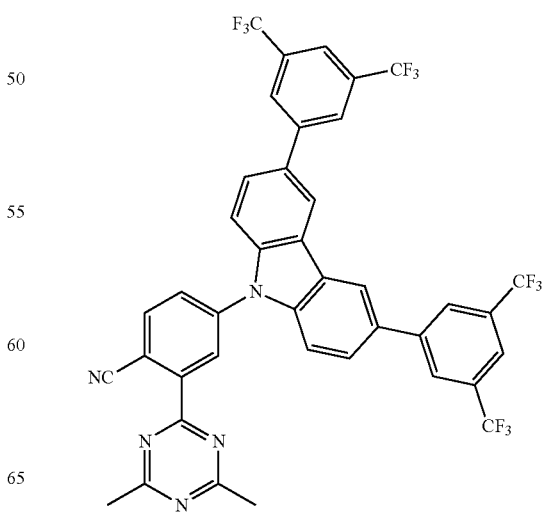

157
-continued
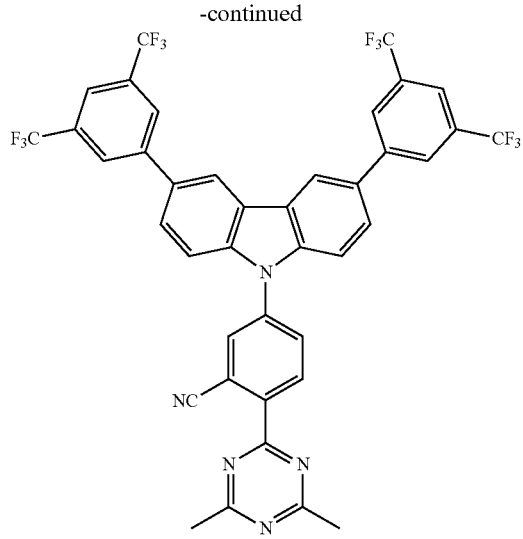
158
-continued
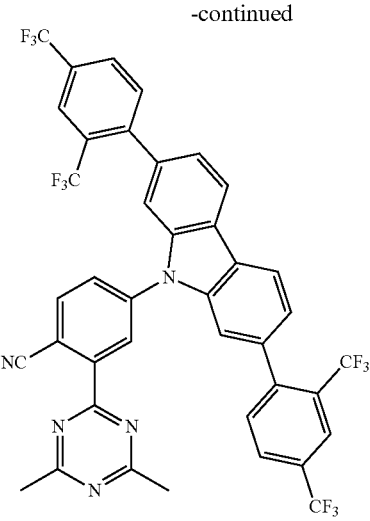
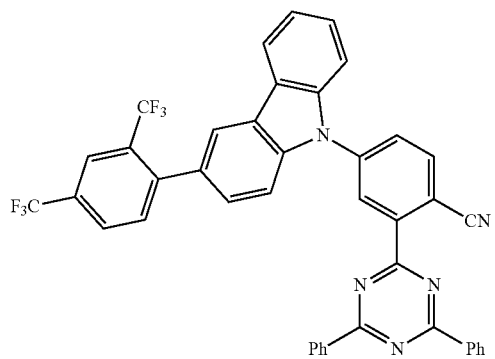
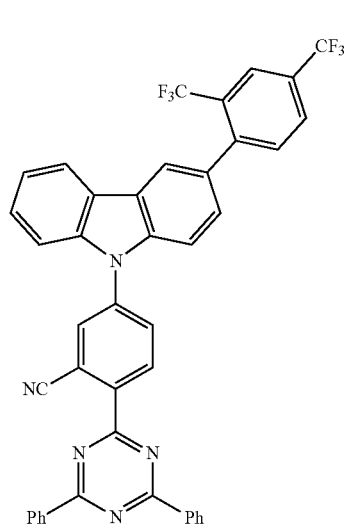
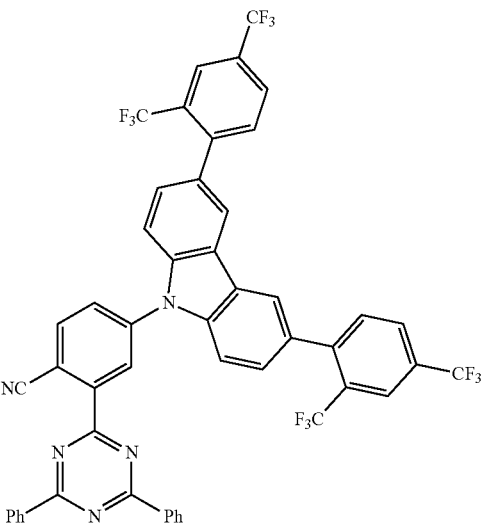

159
-continued
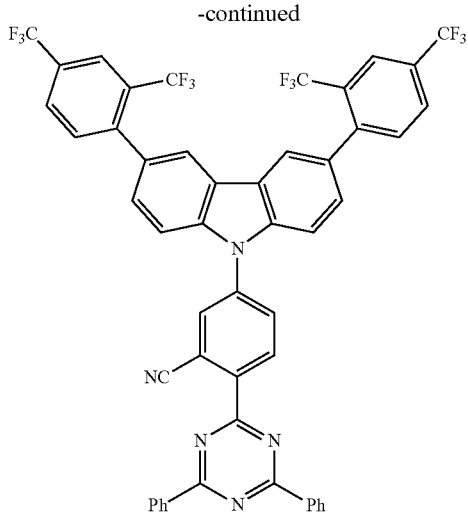
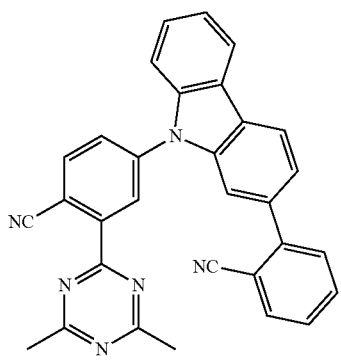
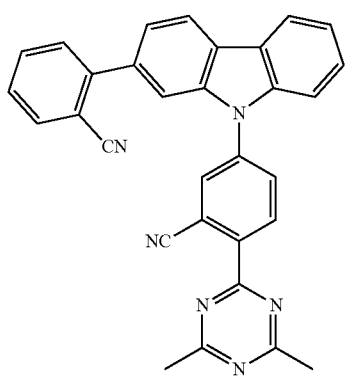
160
-continued
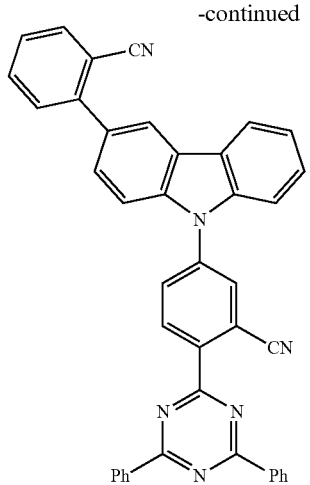
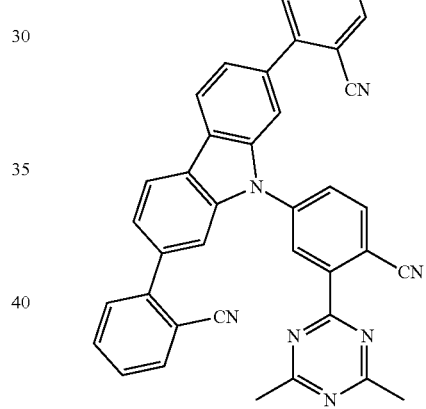
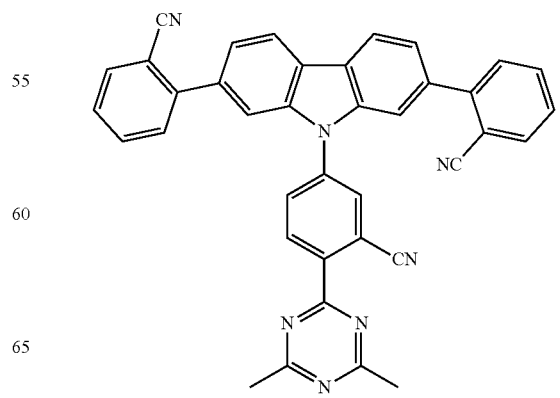

161
-continued
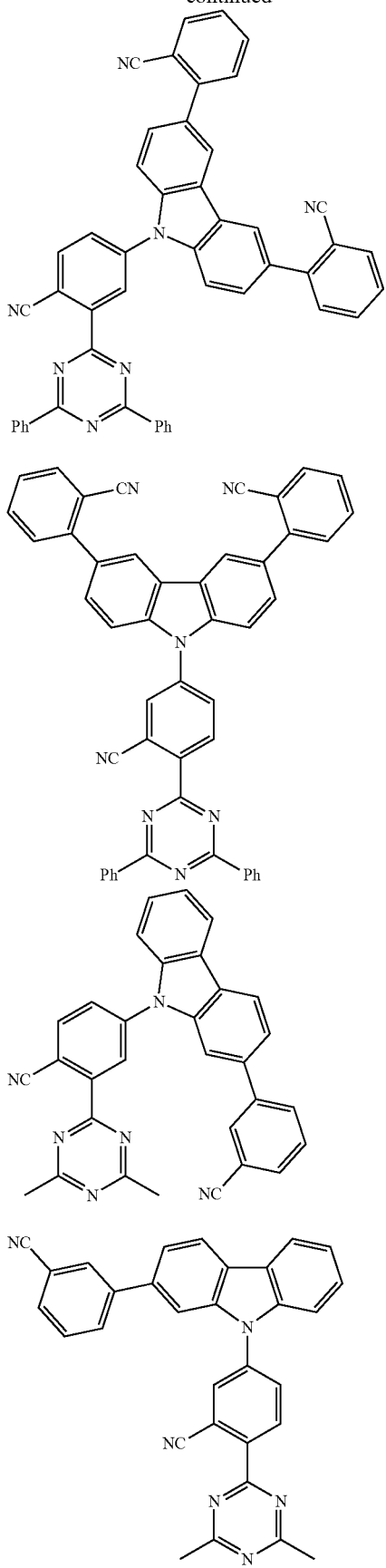
162
-continued
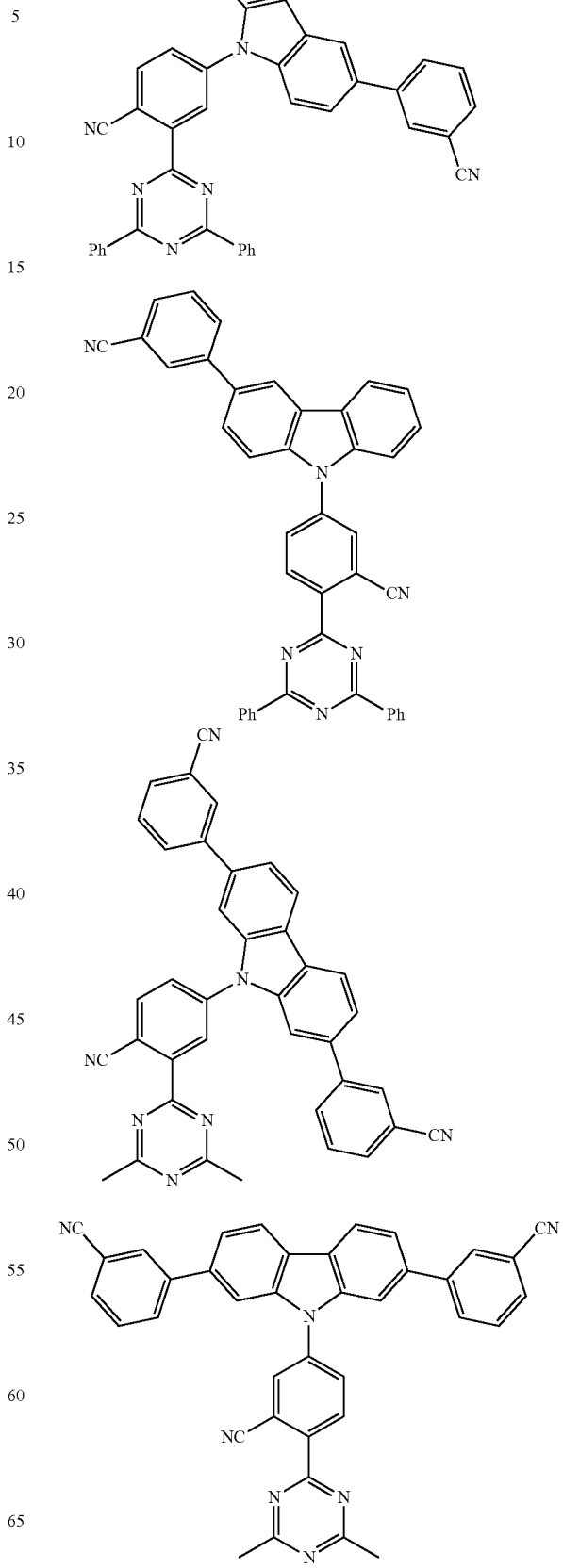

-continued
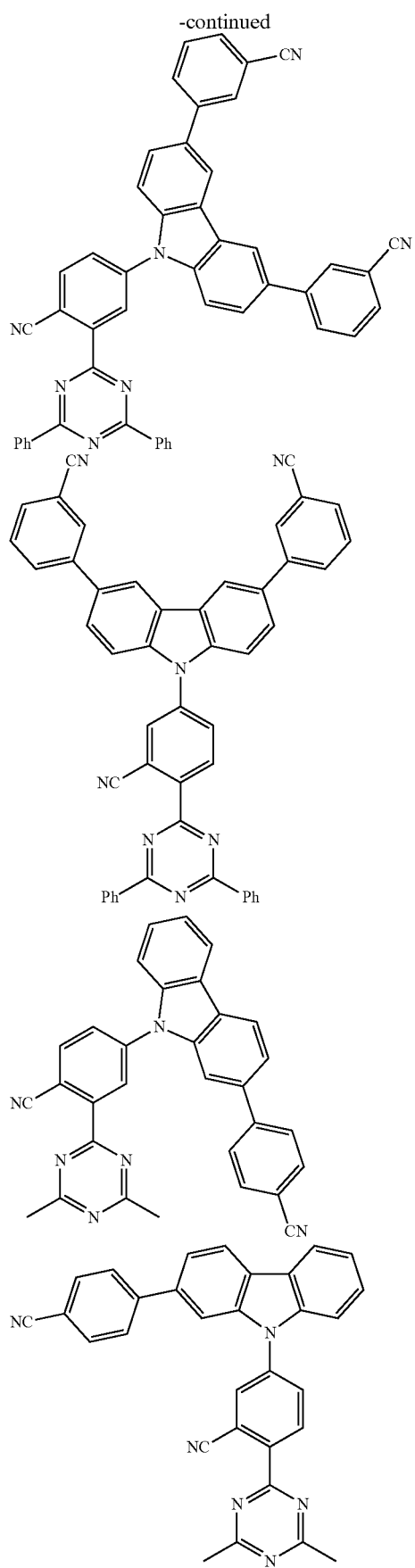
-continued
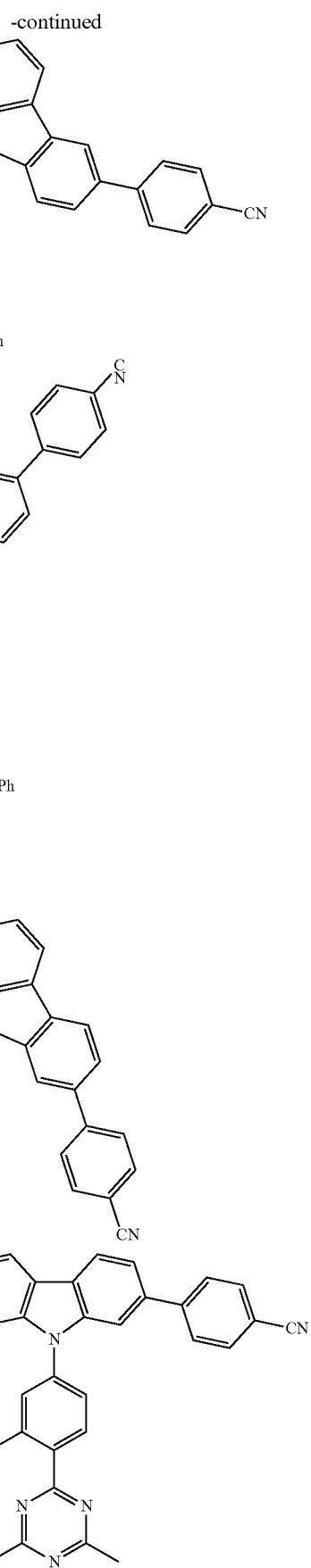

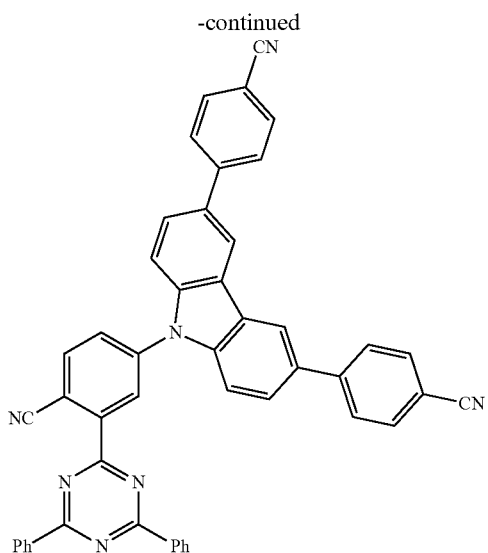
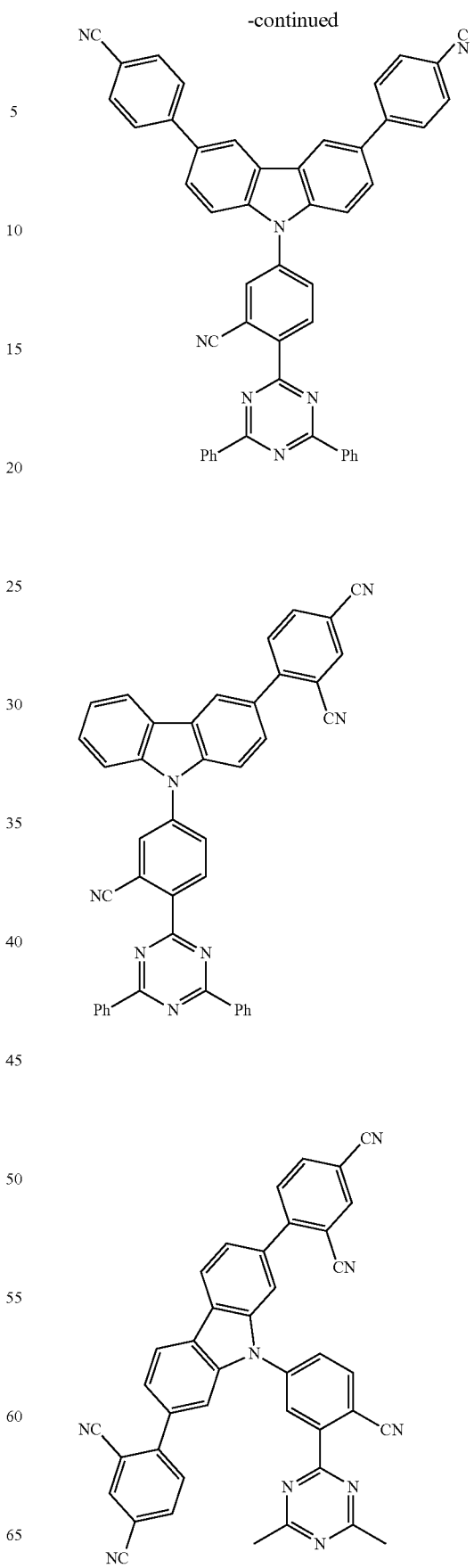

167
-continued
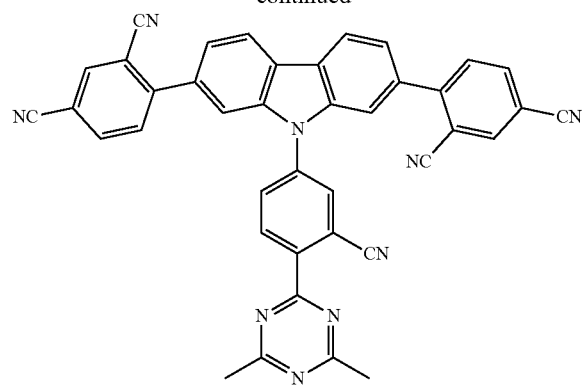
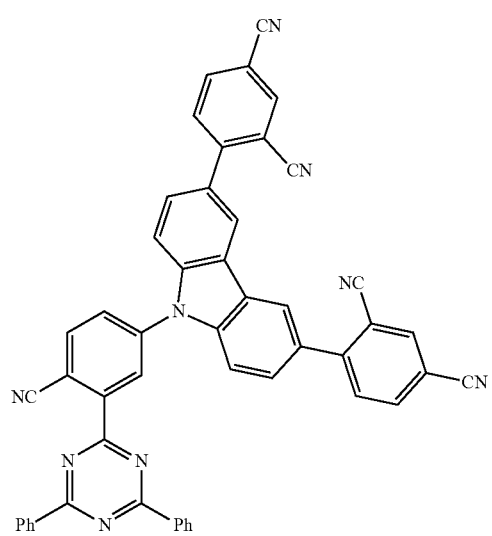
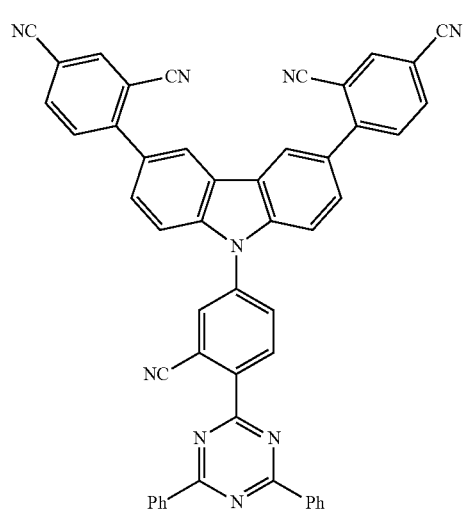
168
-continued
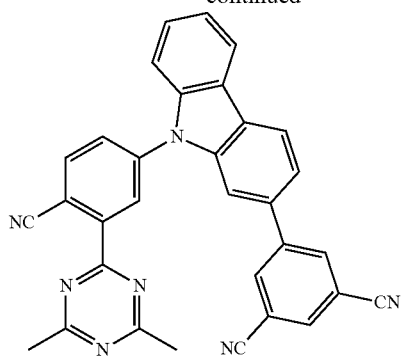
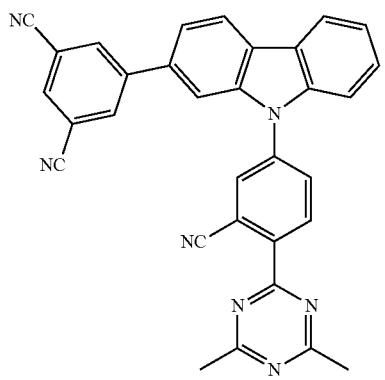
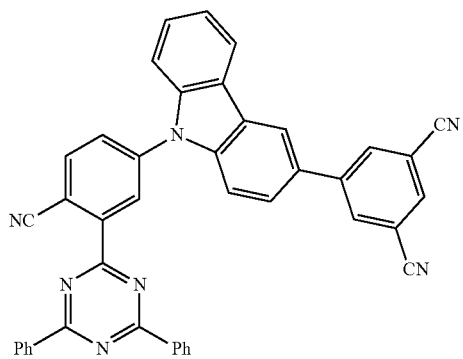
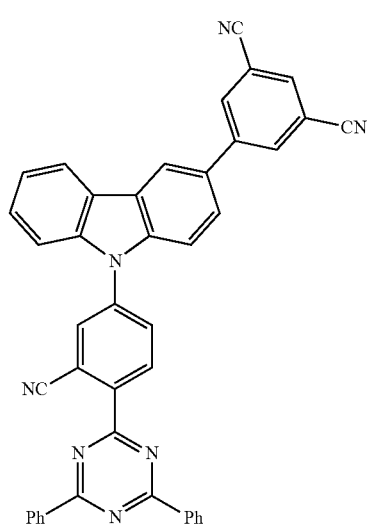

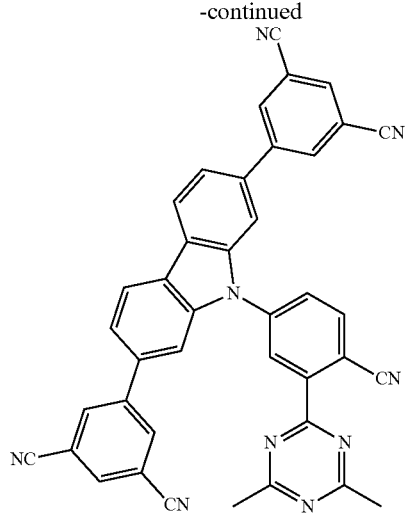
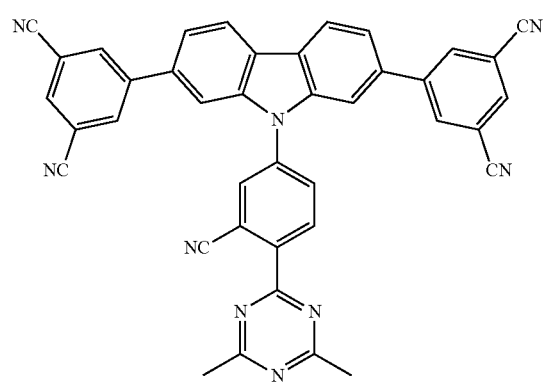
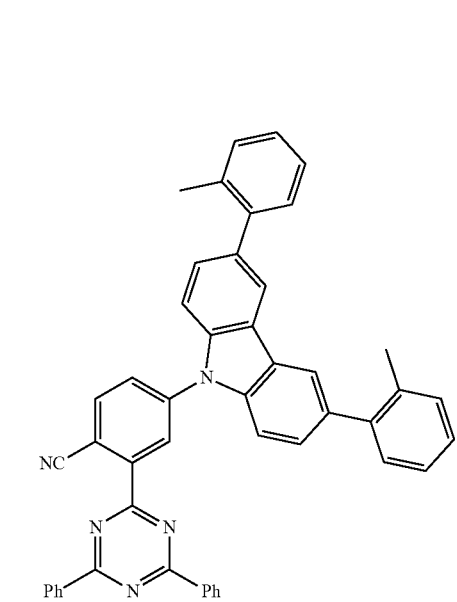
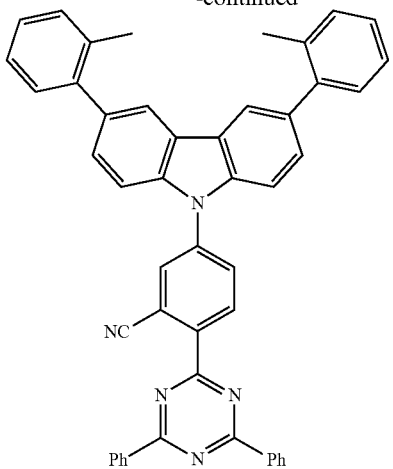
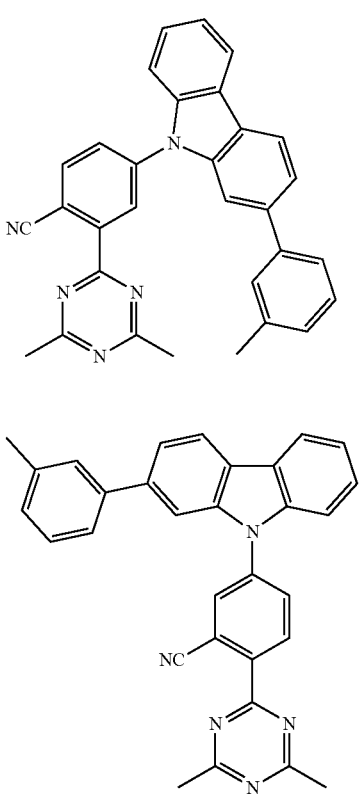
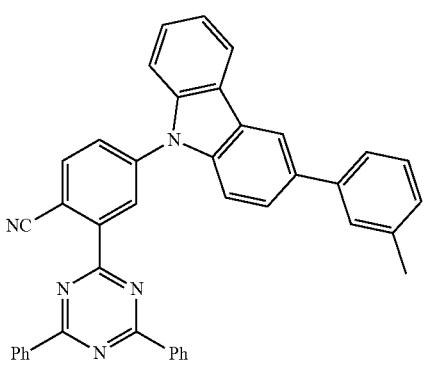

171
-continued
172
-continued
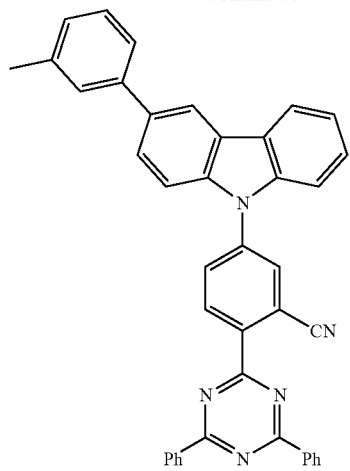 [SMILES: Cc1cccc(-c2ccc3c(c2)c2ccccc2n3-c2ccc(-c3nc(-c4ccccc4)nc(-c4ccccc4)n3)c(C#N)c2)c1]
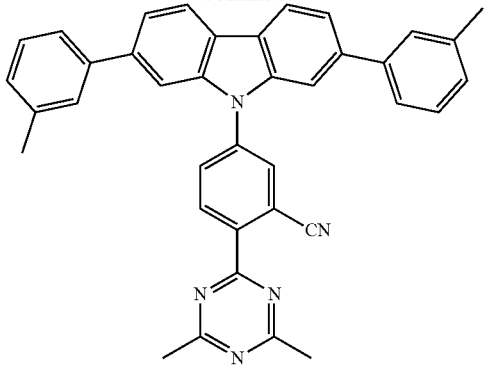
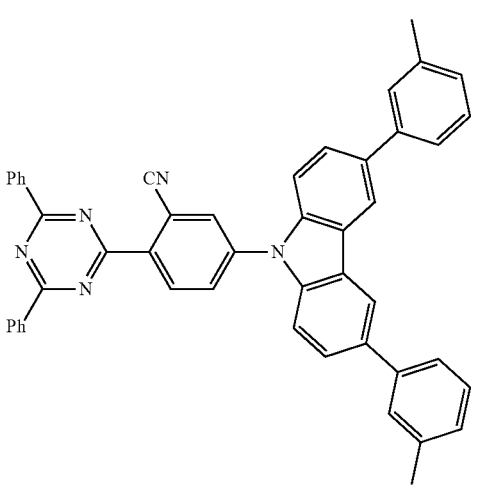
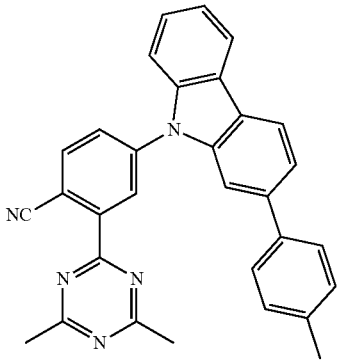
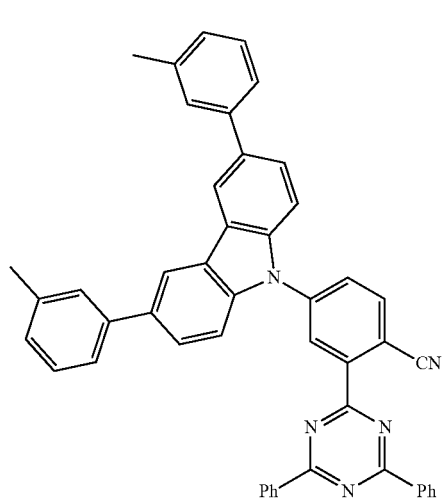
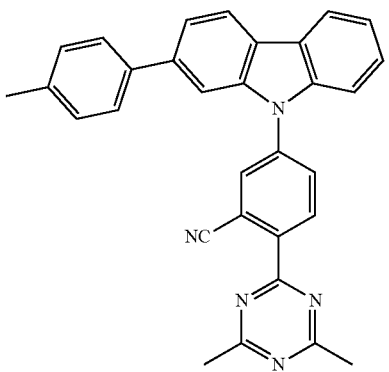

173
-continued
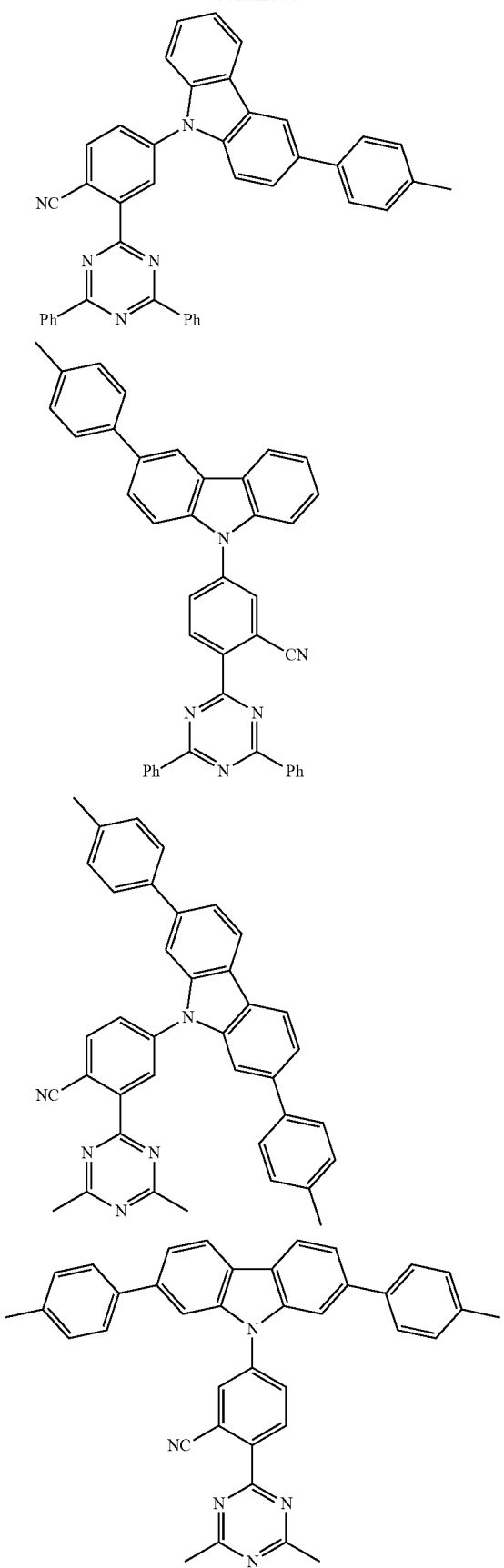
174
-continued
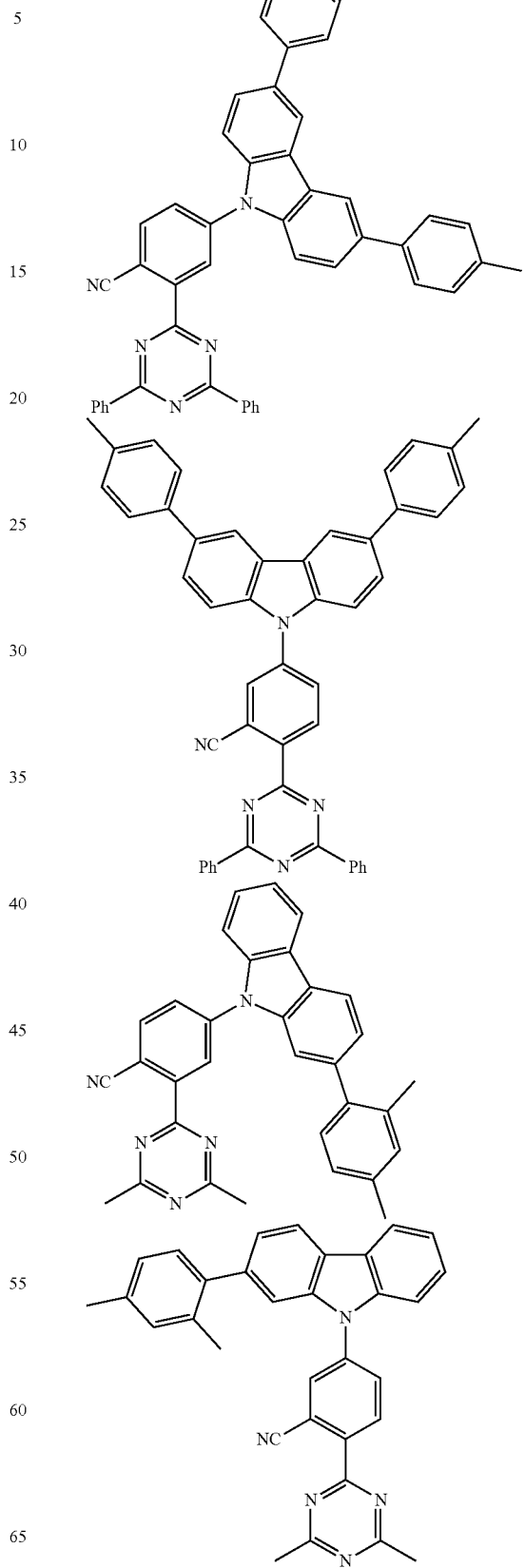

175
-continued
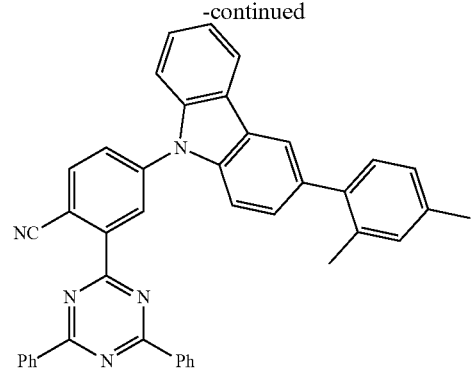
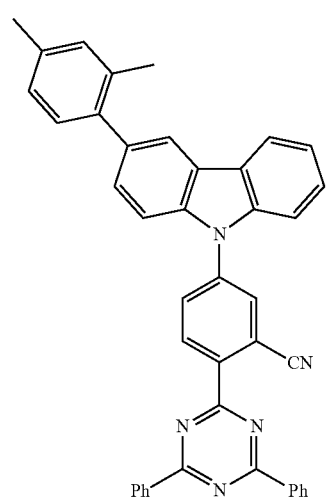
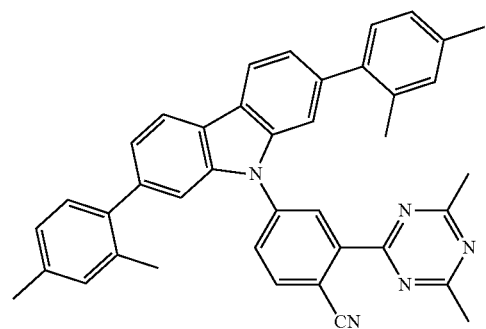
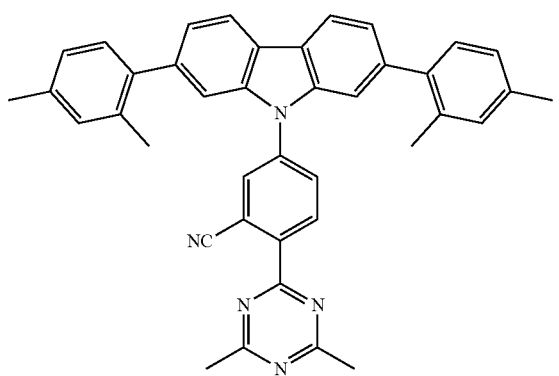
176
-continued
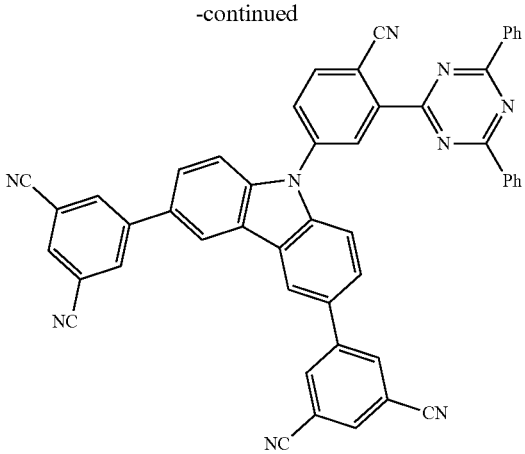
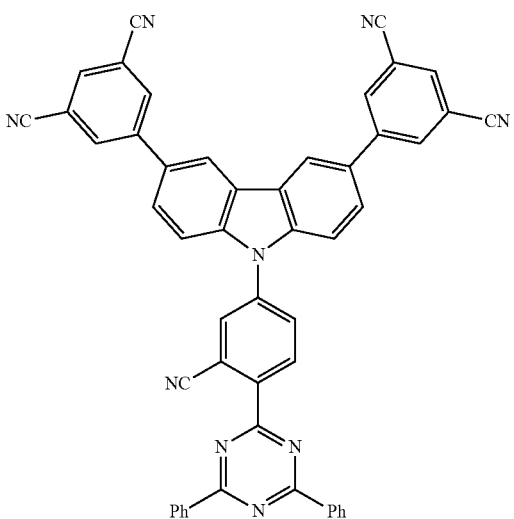
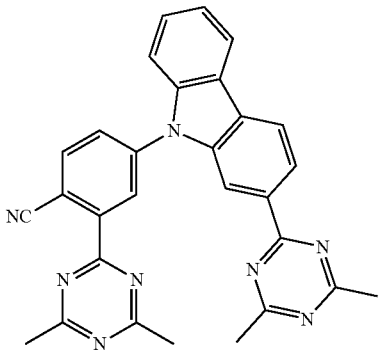
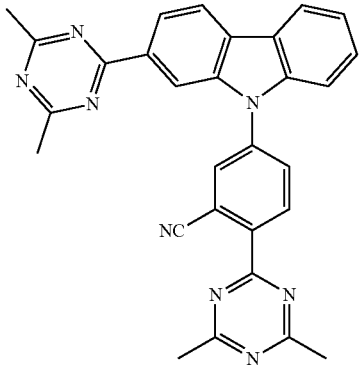

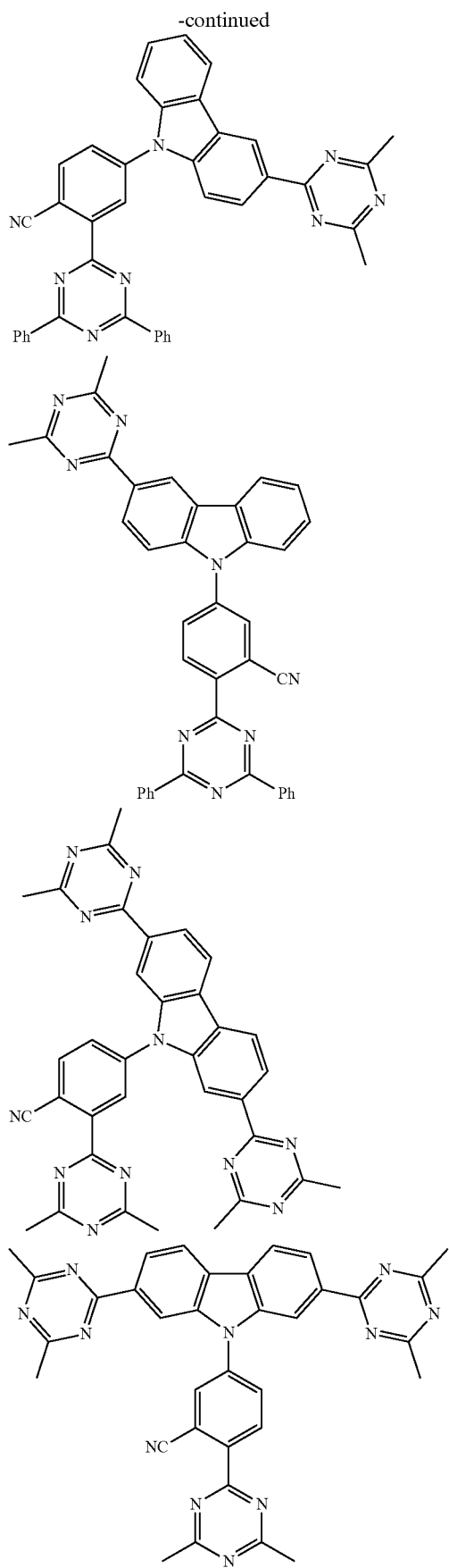
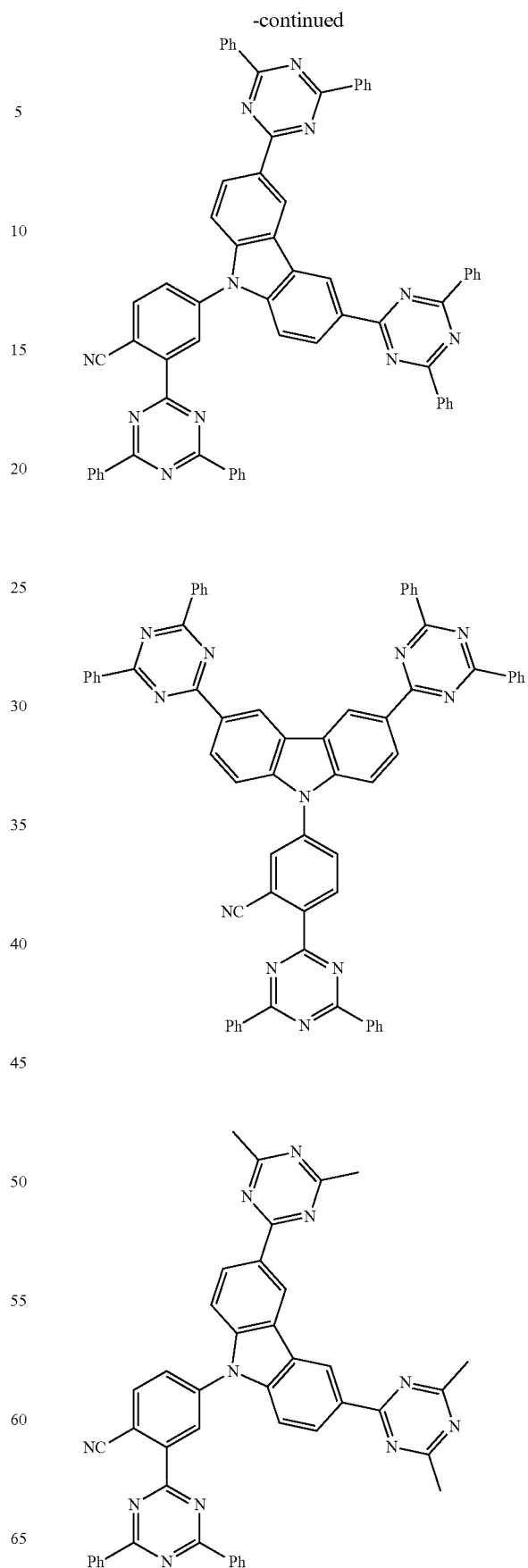

179
-continued
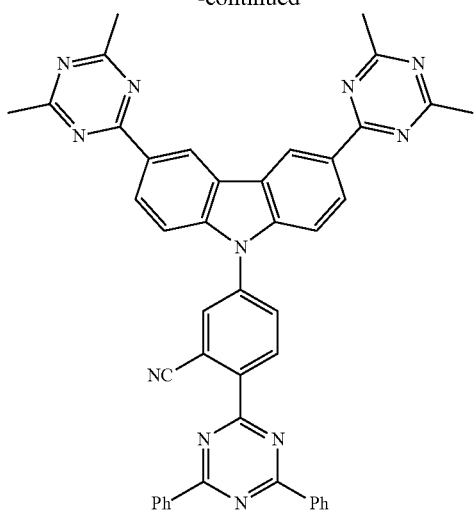
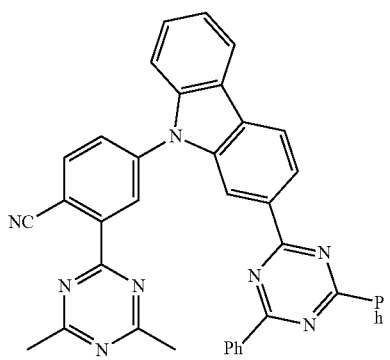
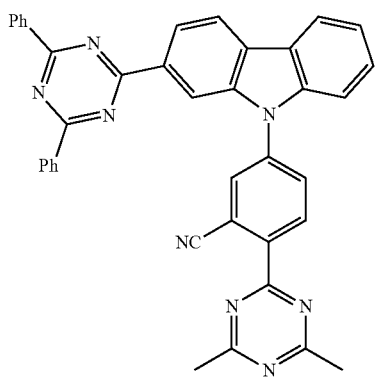
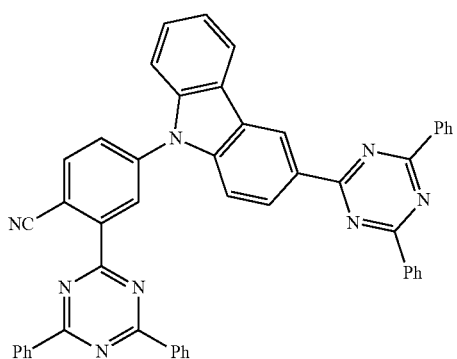
180
-continued
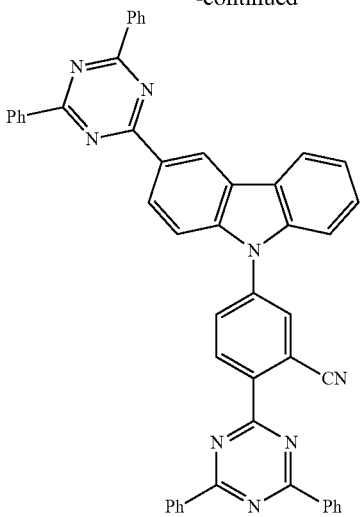
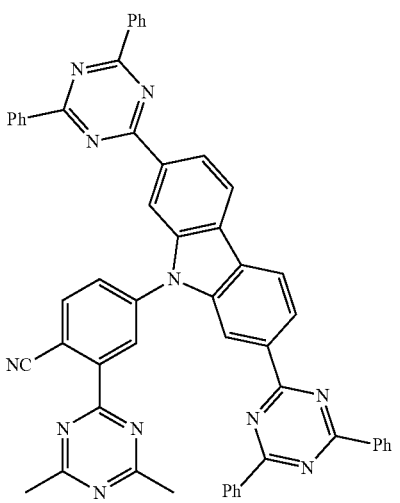
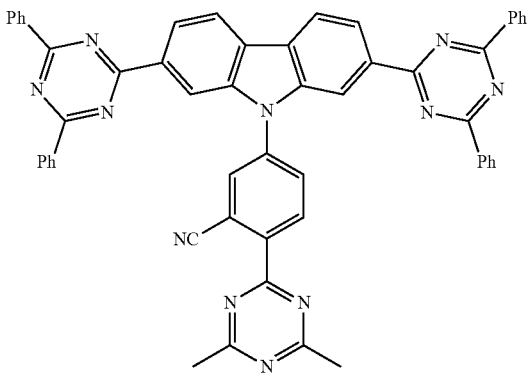

The invention claimed is:
1. An organic molecule comprising or consisting of a structure of formula V

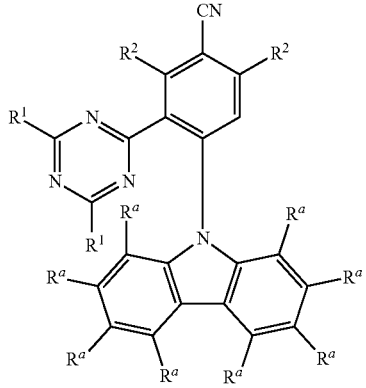

Formula V $R^1$ is the same or different at each instance and is selected from the group consisting of:
  H, deuterium,
  a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms in the aforementioned groups may be replaced by deuterium; and
  an aromatic or heteroaromatic ring system which has 5 to 15 aromatic ring atoms and may be substituted in each case by one or more $R^6$ radicals;
$R^2$ is the same or different at each instance and is selected from the group consisting of:
  H, deuterium,
  a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms in the aforementioned groups may be replaced by deuterium; and
  an aromatic or heteroaromatic ring system which has 5 to 15 aromatic ring atoms and may be substituted in each case by one or more $R^6$ radicals;
$R^a$ are the same or different at each instance and are selected from the group consisting of:
  H, deuterium, $N(R^5)_2$, OH, $Si(R^5)_3$, $B(OR^5)_2$, $OSO_2R^5$, $CF_3$, CN, F, Br, I;
  a linear alkyl, alkoxy or thioalkoxy group which has 1 to 40 carbon atoms and may be substituted in each case by one or more $R^5$ radicals, where one or more nonadjacent $CH_2$ groups may be replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and where one or more hydrogen atoms may be replaced by deuterium, CN, $CF_3$ or $NO_2$;
  a linear alkenyl or alkynyl group which has 2 to 40 carbon atoms and may be substituted in each case by one or more $R^5$ radicals, where one or more nonadjacent $CH_2$ groups may be replaced by $R^5C=CR^5$, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and where one or more hydrogen atoms may be replaced by deuterium, CN, $CF_3$ or $NO_2$;
  a branched or cyclic alkyl, alkenyl, alkynyl, alkoxy or thioalkoxy group which has 3 to 40 carbon atoms and may be substituted in each case by one or more $R^5$ radicals, where one or more nonadjacent $CH_2$ groups may be replaced by $R^5C=CR^5$, C≡C, $Si(R^5)_2$, $Ge(R^5)_2$, $Sn(R^5)_2$, C=O, C=S, C=Se, C=$NR^5$, P(=O)($R^5$), SO, $SO_2$, $NR^5$, O, S or $CONR^5$ and where one or more hydrogen atoms may be replaced by deuterium, CN, $CF_3$ or $NO_2$;
  an aromatic or heteroaromatic ring system which has 5 to 60 aromatic ring atoms and may be substituted in each case by one or more $R^5$ radicals;
  an aryloxy or heteroaryloxy group which has 5 to 60 aromatic ring atoms and may be substituted in each case by one or more $R^5$ radicals; and
  a diarylamino group, diheteroarylamino group or arylheteroarylamino group which has 10 to 40 aromatic ring atoms and may be substituted in each case by one or more $R^5$ radicals;
$R^5$ is the same or different at each instance and is selected from the group consisting of:
  H, deuterium, $N(R^6)_2$, OH, $Si(R^6)_3$, $B(OR^6)_2$, $OSO_2R^6$, $CF_3$, CN, F, Br, I;
  a linear alkyl, alkoxy or thioalkoxy group which has 1 to 40 carbon atoms and may be substituted in each case by one or more $R^6$ radicals, where one or more nonadjacent $CH_2$ groups may be replaced by $R^6C=CR^6$, C≡C, $Si(R^6)_2$, $Ge(R^6)_2$, $Sn(R^6)_2$, C=O, C=S, C=Se, C=$NR^6$, P(=O)($R^6$), SO, $SO_2$, $NR^6$, O, S or $CONR^6$ and where one or more hydrogen atoms may be replaced by deuterium, CN, $CF_3$ or $NO_2$;
  a linear alkenyl or alkynyl group which has 2 to 40 carbon atoms and may be substituted in each case by one or more $R^6$ radicals, where one or more nonadjacent $CH_2$ groups may be replaced by $R^6C=CR^6$, $Si(R^6)_2$, $Ge(R^6)_2$, $Sn(R^6)_2$, C=O, C=S, C=Se, C=$NR^6$, P(=O)($R^6$), SO, $SO_2$, $NR^6$, O, S or $CONR^6$ and where one or more hydrogen atoms may be replaced by deuterium, CN, $CF_3$ or $NO_2$;
  a branched or cyclic alkyl, alkenyl, alkynyl, alkoxy or thioalkoxy group which has 3 to 40 carbon atoms and may be substituted in each case by one or more $R^6$ radicals, where one or more nonadjacent $CH_2$ groups may be replaced by $R^6C=CR^6$, C≡C, $Si(R^6)_2$, $Ge(R^6)_2$, $Sn(R^6)_2$, C=O, C=S, C=Se, C=$NR^6$, P(=O)($R^6$), SO, $SO_2$, $NR^6$, O, S or $CONR^6$ and where one or more hydrogen atoms may be replaced by deuterium, CN, $CF_3$ or $NO_2$;
  an aromatic or heteroaromatic ring system which has 5 to 60 aromatic ring atoms and may be substituted in each case by one or more $R^6$ radicals;
  an aryloxy or heteroaryloxy group which has 5 to 60 aromatic ring atoms and may be substituted in each case by one or more $R^6$ radicals; and
  a diarylamino group, diheteroarylamino group or arylheteroarylamino group which has 10 to 40 aromatic ring atoms and may be substituted in each case by one or more $R^6$ radicals;
$R^6$ is the same or different at each instance and is selected from the group consisting of:
  H, deuterium, OH, $CF_3$, CN, F;
  a linear alkyl, alkoxy or thioalkoxy group having 1 to 5 carbon atoms, where one or more hydrogen atoms may be replaced by deuterium, CN, $CF_3$ or $NO_2$;

a linear alkenyl or alkynyl group having 2 to 5 carbon atoms, where one or more hydrogen atoms may be replaced by deuterium, CN, $CF_3$ or $NO_2$;

a branched or cyclic alkyl, alkenyl, alkynyl, alkoxy or thioalkoxy group having 3 to 5 carbon atoms, where one or more hydrogen atoms may be replaced by deuterium, CN, $CF_3$ or $NO_2$;

an aromatic or heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms;

wherein each of the $R^a$ or $R^5$ radicals together with one or more further $R^a$ or $R^5$ radicals may form a mono- or polycyclic, aliphatic, aromatic and/or benzo fused ring system.

2. The organic molecule according to claim 1, wherein $R^1$ is methyl or phenyl.

3. The organic molecule according to claim 1, wherein $R^2$ is H, methyl or phenyl.

4. The organic molecule according to claim 1, wherein the structure is of formula Va:

Formula Va

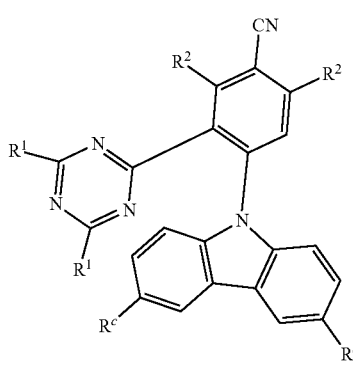

wherein $R^c$ is the same or different at each instance and is selected from the group consisting of:

Me, $^iPr$, $^tBu$, CN, $CF_3$, Ph, pyridinyl, pyrimidinyl, carbazolyl, triazinyl which may be substituted in each case by one or more radicals selected from Me, $^iPr$, $^tBu$, CN, $CF_3$ and Ph.

5. The organic molecule according to claim 1, where the structure of formula Vb:

Formula Vb

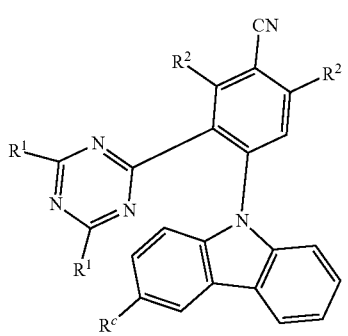

wherein $R^c$ is the same or different at each instance and is selected from the group consisting of:

Me, $^iPr$, $^tBu$, CN, $CF_3$, Ph, pyridinyl, pyrimidinyl, carbazolyl, triazinyl which may be substituted in each case by one or more radicals selected from Me, $^iPr$, $^tBu$, CN, $CF_3$ and Ph.

6. The organic molecule according to claim 4, wherein $R^c$ is Me, $^iPr$, $^tBu$, CN, $CF_3$, Ph, pyridinyl, pyrimidinyl or triazinyl, which may be substituted in each case by one or more radicals selected from Me, $^iPr$, $^tBu$, CN, $CF_3$ and Ph.

7. The organic molecule according to claim 5, wherein $R^c$ is Me, $^iPr$, $^tBu$, CN, $CF_3$, Ph, pyridinyl, pyrimidinyl or triazinyl, which may be substituted in each case by one or more radicals selected from Me, $^iPr$, $^tBu$, CN, $CF_3$ and Ph.

8. A process for preparing an organic molecule according to claim 1, wherein a 4- and 6-$R^1$-substituted 2-halo-1,3,5-triazine is used as reactant.

9. An organic optoelectronic device comprising at least one of a luminescent emitter, a host material, electron transport material, hole injection material, and hole blocker material, wherein the luminescent emitter, the host material, the electron transport material, the hole injection material, and the hole blocker material comprise the organic molecule according to claim 1.

10. The organic optoelectronic device according to claim 9, wherein the organic optoelectronic device is selected from the group consisting of an organic light-emitting diode (OLED), a light-emitting electrochemical cell, an OLED sensor, an organic diode, an organic solar cell, an organic transistor, an organic field-effect transistor, an organic laser and a down-conversion element.

11. A composition comprising:
at least one organic molecule according to claim 1;
at least one of an emitter and a host material not comprising the organic molecule according to claim 1; and
at least one of a dye and a solvent.

12. An organic optoelectronic device comprising a composition according to claim 11, wherein the organic optoelectronic device is selected from the group consisting of organic light-emitting diode (OLED), a light-emitting electrochemical cell, an OLED sensor, an organic diode, an organic solar cell, an organic transistor, an organic field effect transistor, an organic laser and a down-conversion element.

13. The organic optoelectronic device according to claim 12, comprising:
a substrate;
an anode;
a cathode, wherein the anode or cathode has been applied to the substrate; and
at least one light-emitting layer arranged between anode and cathode, wherein at least one light-emitting layer comprises the composition according to claim 11.

14. A method for manufacturing an optoelectronic component, comprising performing processing of the organic molecule according to claim 1 from a solution or by using a vacuum evaporation process.

* * * * *